United States Patent
Takino et al.

(10) Patent No.: US 9,308,157 B2
(45) Date of Patent: Apr. 12, 2016

(54) WHITENING COSMETIC

(71) Applicant: AJINOMOTO CO., INC., Tokyo (JP)

(72) Inventors: Yoshinobu Takino, Kawasaki (JP); Fumie Okura, Kawasaki (JP); Shinji Kuroda, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/288,791

(22) Filed: May 28, 2014

(65) Prior Publication Data

US 2014/0271510 A1 Sep. 18, 2014

Related U.S. Application Data

(63) Continuation of application No. PCT/JP2012/081192, filed on Nov. 30, 2012.

(30) Foreign Application Priority Data

Nov. 30, 2011 (JP) .................. 2011-262164

(51) Int. Cl.

| A61K 8/49 | (2006.01) |
|---|---|
| A61K 8/36 | (2006.01) |
| A61K 8/368 | (2006.01) |
| A61K 8/44 | (2006.01) |
| A61K 8/60 | (2006.01) |
| A61K 8/64 | (2006.01) |
| A61K 8/97 | (2006.01) |
| A61Q 19/02 | (2006.01) |
| A61K 31/426 | (2006.01) |

(52) U.S. Cl.
CPC . *A61K 8/49* (2013.01); *A61K 8/361* (2013.01); *A61K 8/368* (2013.01); *A61K 8/44* (2013.01); *A61K 8/498* (2013.01); *A61K 8/4973* (2013.01); *A61K 8/602* (2013.01); *A61K 8/64* (2013.01); *A61K 8/97* (2013.01); *A61K 31/426* (2013.01); *A61Q 19/02* (2013.01); *A61K 8/445* (2013.01)

(58) Field of Classification Search
None
See application file for complete search history.

(56) References Cited

U.S. PATENT DOCUMENTS

2013/0095048 A1 4/2013 Amino et al.

FOREIGN PATENT DOCUMENTS

| CN | 102917685 A | 2/2013 |
|---|---|---|
| EP | 2 578 203 A1 | 4/2013 |
| JP | 2009-227660 A | 10/2009 |
| JP | 2010-001239 A | 1/2010 |
| WO | WO 2011/149093 A1 | 12/2011 |

OTHER PUBLICATIONS

Maxwell P. Schubert, "Reactions of semimercaptals with amino compounds", Journal of Biological Chemistry, vol. 121, 1937, pp. 539-548.

Giuseppe Cremonesi, et al., "Asymmetric synthesis of 1,3-thiazolidine-derived spiro-β-lactams via a Staudinger reaction between chiral ketenes and imines", Tetrahedron: Asymmetry, vol. 16, 2005, pp. 3371-3379.

Jean Pierre Nallet, et al., "Synthesis of a series of hexitol and aminodeoxyhexitol mononitrate derivatives containing a sulfur group and pharmacological evaluation on isolated rat aortas", European Journal of Organic Chemistry, vol. 1998. No. 5, May 1998, pp. 933-943.

Extended European Search Report issued Oct. 6, 2015 in Patent Application No. 12853735.4.

Extended European Search Report issued Jul. 24, 2015 in Patent Application No. 12853735.4.

Marta I. Rendon, et al., "Review of Skin-Lightening Agents" Dermatologic Surgery, vol. 31, No. 7, XP055198249, Jul. 2005, pp. 886-889.

J. M. Gillbro, et al., "The melanogenesis and mechanisms of skin-lightening agents—existing and new approaches" International Journal of Cosmetic Science, vol. 33, XP055000016, 2011, pp. 210-221.

*Primary Examiner* — Bethany Barham
*Assistant Examiner* — Barbara Frazier
(74) *Attorney, Agent, or Firm* — Oblon, McClelland, Maier & Neustadt, L.L.P.

(57) ABSTRACT

Compositions, comprising
 (A) a cysteine derivative represented by the formula (I) or a salt thereof:

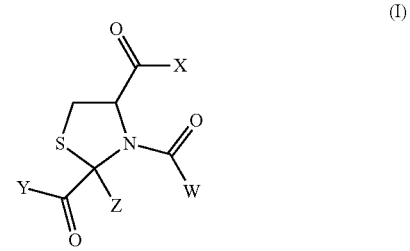

wherein
 X and Y are each independently $OR^1$ or $NHR^2$ wherein $R^1$ and $R^2$ are each independently a hydrogen atom or a $C_{1-22}$ alkyl group;
 Z is a hydrogen atom or a $C_{1-22}$ alkyl group; and
 W is a $C_{1-22}$ alkyl group, a $C_{1-22}$ alkoxy group or a $C_{1-22}$ alkylamino group, and
 (B) a whitening agent,
are useful for whitening skin and reducing melanin production.

22 Claims, No Drawings

WHITENING COSMETIC

CROSS REFERENCES TO RELATED APPLICATIONS

This application is a continuation of International Patent Application No. PCT/JP2012/081192, filed on Nov. 30, 2012, and claims priority to Japanese Patent Application No. 2011-262164, filed on Nov. 30, 2011, both of which are incorporated herein by reference in their entireties.

BACKGROUND OF THE INVENTION

1. Field of the Invention

The present invention relates to a cosmetic agent containing (A) a particular cysteine derivative or a salt thereof and (B) a particular whitening agent.

2. Discussion of the Background

Conventionally, to prevent suntan, pigmented spot, freckle of the skin and maintain the inherent fair skin, whitening cosmetic agents containing various whitening agents such as kojic acid, arbutin, rcinol, ellagic acid and the like have been proposed. However, when these substances are blended in large amounts, problems in the sense of use and safety may occur, which prevents use thereof at a concentration expected to provide a sufficient effect.

On the other hand, patent document 1 describes that a cysteine derivative obtained by esterification of L-2-methylthiazolidine-2,4-dicarboxylic acid or a salt thereof is useful as a whitening agent etc. Furthermore, patent document 2 describes that 2-methylthiazolidine-2,4-dicarboxylic acid or a derivative thereof has a whitening action. However, since these derivatives are easily decomposed and insufficient in the stability, practicalization thereof has not been achieved. The particular cysteine derivative of the present invention is not described.

DOCUMENT LIST

Patent Documents patent document 1: JP-A-2009-227660
patent document 2: JP-A-2010-1239

SUMMARY OF THE INVENTION

Problems to be Solved by the Invention

The problem of the present invention is to provide a cosmetic agent superior in the whitening effect.

In addition, the problem of the present invention is to provide a composition for suppressing melanin production (melanin production suppressive agent) which has high stability and high safety.

Means of Solving the Problems

As a result of the intensive studies, it was found that a combined use of a particular cysteine derivative having high stability and high safety and a whitening agent is particularly superior in the whitening effect, and that a combined use of a particular cysteine derivative and a whitening agent synergistically improves a melanin production suppressive effect, and surprisingly, can also improve the cell viability rate, which resulted in the completion of the present invention.

Accordingly, the present invention provides the following.

[1] A cosmetic agent comprising (A) a cysteine derivative represented by the formula (I) or a salt thereof:

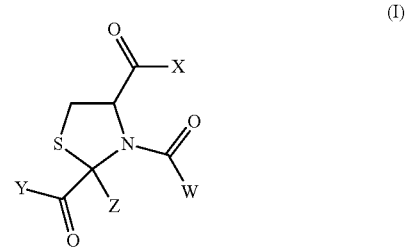

wherein
X and Y are each independently $OR^1$ or $NHR^2$ wherein $R^1$ and $R^2$ are each independently a hydrogen atom or a $C_{1-22}$ alkyl group;
Z is a hydrogen atom or a $C_{1-22}$ alkyl group; and
W is a $C_{1-22}$ alkyl group, a $C_{1-22}$ alkoxy group or a $C_{1-22}$ alkylamino group, and
(B) a whitening agent.

[2] The cosmetic agent of the above-mentioned [1], wherein (A) the cysteine derivative or a salt thereof is one or more kinds selected from N-acetyl-2-methylthiazolidine-2,4-dicarboxylic acid, and N-acetyl-2-methylthiazolidine-2,4-dicarboxylic acid 2-ethyl ester, and a salt thereof.

[3] The cosmetic agent of the above-mentioned [1] or [2], wherein (B) the whitening agent is one or more kinds selected from hydroquinone and a derivative thereof, ascorbic acid and a derivative thereof, kojic acid and a derivative thereof, a nicotinic acid derivative, a serotonin derivative, a salicylic acid derivative, astaxanthin, α-lipoic acid, calcium panthetheine sulfonate, an extract having a whitening effect, a plant extract having a whitening effect, polyphenol having a whitening effect, unsaturated fatty acid having a whitening effect, peptide having a whitening effect, amino acid having a whitening effect, a nucleic acid derivative having a whitening effect, and alkylphenol having a whitening effect.

[4] The cosmetic agent of the above-mentioned [1] or [2], wherein (B) the whitening agent is one or more kinds selected from arbutin, cetyl ascorbyl ether, kojic acid, 4-methoxy salicylic acid, chamomilla recutita extract, ellagic acid, linoleic acid, glutathione, tranexamic acid, and retinol.

[5] The cosmetic agent of the above-mentioned [1], wherein (A) the cysteine derivative or a salt thereof is N-acetyl-2-methylthiazolidine-2,4-dicarboxylic acid 2-ethyl ester or a salt thereof, and (B) the whitening agent is kojic acid.

[6] The cosmetic agent of the above-mentioned [1], wherein (A) the cysteine derivative or a salt thereof is N-acetyl-2-methylthiazolidine-2,4-dicarboxylic acid 2-ethyl ester or a salt thereof, and (B) the whitening agent is tranexamic acid.

[7] The cosmetic agent of the above-mentioned [1], wherein (A) the cysteine derivative or a salt thereof is N-acetyl-2-methylthiazolidine-2,4-dicarboxylic acid 2-ethyl ester or a salt thereof, and (B) the whitening agent is a chamomilla recutita extract.

[8] The cosmetic agent of the above-mentioned [1], wherein (A) the cysteine derivative or a salt thereof is N-acetyl-2-methylthiazolidine-2,4-dicarboxylic acid 2-ethyl ester or a salt thereof, and (B) the whitening agent is arbutin.

[9] The cosmetic agent of any of the above-mentioned [1]-[8], wherein a mixing ratio of (A) the cysteine derivative or a salt thereof and (B) the whitening agent is (A)/(B)=1/20-5000/1 (g/g).

[10] The cosmetic agent of any of the above-mentioned [1]-[9], wherein (A) the cysteine derivative represented by the formula (I) is one or more kinds selected from a (2R,4S)-form, a (2S,4R)-form, and a mixture thereof.

[11] The cosmetic agent of any of the above-mentioned [1]-[9], wherein (A) the cysteine derivative represented by the formula (I) is a (2S,4R)-form.

[12] A melanin production suppressive agent comprising (A) a cysteine derivative represented by the formula (I) or a salt thereof:

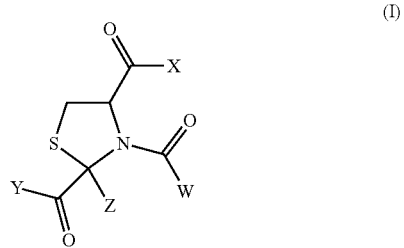

(I)

wherein

X and Y are each independently $OR^1$ or $NHR^2$ wherein $R^1$ and $R^2$ are each independently a hydrogen atom or a $C_{1-22}$ alkyl group;

Z is a hydrogen atom or a $C_{1-22}$ alkyl group; and

W is a $C_{1-22}$ alkyl group, a $C_{1-22}$ alkoxy group or a $C_{1-22}$ alkylamino group, and (B) a whitening agent.

[13] The melanin production suppressive agent of the above-mentioned [12], wherein (A) the cysteine derivative or a salt thereof is one or more kinds selected from N-acetyl-2-methylthiazolidine-2,4-dicarboxylic acid, and N-acetyl-2-methylthiazolidine-2,4-dicarboxylic acid 2-ethyl ester, and a salt thereof.

[14] The melanin production suppressive agent of the above-mentioned [12] or [13], wherein (B) the whitening agent is one or more kinds selected from hydroquinone and a derivative thereof, ascorbic acid and a derivative thereof, kojic acid and a derivative thereof, a nicotinic acid derivative, a serotonin derivative, a salicylic acid derivative, astaxanthin, α-lipoic acid, calcium panteteheine sulfonate, an extract having a whitening effect, a plant extract having a whitening effect, polyphenol having a whitening effect, unsaturated fatty acid having a whitening effect, peptide having a whitening effect, amino acid having a whitening effect, a nucleic acid derivative having a whitening effect, and alkylphenol having a whitening effect.

[15] The melanin production suppressive agent of any of the above-mentioned [12]-[14], wherein (B) the whitening agent is one or more kinds selected from arbutin, cetyl ascorbyl ether, kojic acid, 4-methoxy salicylic acid, chamomilla recutita extract, ellagic acid, linoleic acid, glutathione, tranexamic acid, and rcinol.

[16] The melanin production suppressive agent of the above-mentioned [12], wherein (A) the cysteine derivative or a salt thereof is N-acetyl-2-methylthiazolidine-2,4-dicarboxylic acid 2-ethyl ester or a salt thereof, and (B) the whitening agent is kojic acid.

[17] The melanin production suppressive agent of the above-mentioned [12], wherein (A) the cysteine derivative or a salt thereof is N-acetyl-2-methylthiazolidine-2,4-dicarboxylic acid 2-ethyl ester or a salt thereof, and (B) the whitening agent is tranexamic acid.

[18] The melanin production suppressive agent of the above-mentioned [12], wherein (A) the cysteine derivative or a salt thereof is N-acetyl-2-methylthiazolidine-2,4-dicarboxylic acid 2-ethyl ester or a salt thereof, and (B) the whitening agent is a chamomilla recutita extract.

[19] The melanin production suppressive agent of the above-mentioned [12], wherein, (A) the cysteine derivative or a salt thereof is N-acetyl-2-methylthiazolidine-2,4-dicarboxylic acid 2-ethyl ester or a salt thereof, and (B) the whitening agent is arbutin.

[20] The melanin production suppressive agent of any of the above-mentioned [12]-[19], wherein a mixing ratio of (A) the cysteine derivative or a salt thereof and (B) the whitening agent is (A)/(B)=1/20-5000/1 (g/g).

[21] The melanin production suppressive agent of any of the above-mentioned [12]-[20], wherein (A) the cysteine derivative represented by the formula (I) is one or more kinds selected from a (2R,4S)-form, a (2S,4R)-form, and a mixture thereof.

[22] The melanin production suppressive agent of any of the above-mentioned [12]-[20], wherein (A) the cysteine derivative represented by the formula (I) is a (2S,4R)-form.

[23] A pharmaceutical external preparation comprising (A) a cysteine derivative represented by the formula (I) or a salt thereof:

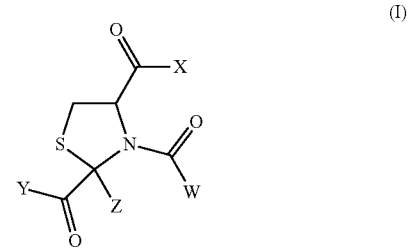

(I)

wherein

X and Y are each independently $OR^1$ or $NHR^2$ wherein $R^1$ and $R^2$ are each independently a hydrogen atom or a $C_{1-22}$ alkyl group;

Z is a hydrogen atom or a $C_{1-22}$ alkyl group; and

W is a $C_{1-22}$ alkyl group, a $C_{1-22}$ alkoxy group or a $C_{1-22}$ alkylamino group, and (B) a whitening agent.

Effect of the Invention

According to the present invention, a melanin production suppressive agent having high stability and high safety is provided, and further, a cosmetic agent superior in a whitening effect and the like and having high safety can be provided.

DETAILED DESCRIPTION OF THE PREFERRED EMBODIMENTS

The present invention is a cosmetic agent containing (A) a particular cysteine derivative or a salt thereof and (B) a particular whitening agent. In addition, the present invention is a melanin production suppressive agent containing (A) and (B), which is applicable as a cosmetic agent (including quasi-drug), a pharmaceutical external preparation and the like.

[(A) The Cysteine Derivative]

The cysteine derivative of the present invention is a cysteine derivative represented by the formula (I) or a salt thereof.

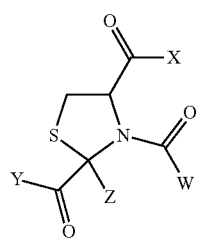

(I)

wherein
X and Y are each independently $OR^1$, $NHR^2$ wherein $R^1$ and $R^2$ are each independently a hydrogen atom or a $C_{1-22}$ alkyl group;
Z is a hydrogen atom or a $C_{1-22}$ alkyl group; and
W is a $C_{1-22}$ alkyl group, a $C_{1-22}$ alkoxy group or a $C_{1-22}$ alkylamino group.

The terms to be used in the present specification are defined in the following.

The "$C_{1-22}$ alkyl group" means a straight chain or branched acyclic hydrocarbon group having 1 to 22 carbon atoms, and examples thereof include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group, a heptyl group, an octyl group, a 2-ethylhexyl group, a tert-octyl group, a nonyl group, an isononyl group, a decyl group, an isodecyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, an isooctadecyl group, a behenyl group and the like.

Examples of the "$C_{1-16}$ alkyl group" include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group, a heptyl group, an octyl group, a 2-ethylhexyl group, a tert-octyl group, a nonyl group, an isononyl group, a decyl group, an isodecyl group, an undecyl group, a dodecyl group, a tridecyl group, an isotridecyl group, a tetradecyl group, a pentadecyl group, a hexadecyl group, an isohexadecyl group and the like.

Examples of the "$C_{1-6}$ alkyl group" include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group and the like.

The "$C_{1-22}$ alkoxy group" means a hydroxyl group substituted by the above-mentioned "$C_{1-22}$ alkyl group", and examples thereof include a methoxy group, an ethoxy group, a propoxy group, an isopropoxy group, a butoxy group, an isobutoxy group, a tert-butoxy group, a pentyloxy group, a hexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, an eicosyloxy group, a heneicosyloxy group, a docosyloxy group and the like.

Examples of the "$C_{1-6}$ alkoxy group" include a methoxy group, an ethoxy group, a propoxy group, an isopropoxy group, a butoxy group, an isobutoxy group, a tert-butoxy group, a pentyloxy group, a hexyloxy group and the like.

The "$C_{1-22}$ alkylamino group" means an amino group substituted by the above-mentioned "$C_{1-22}$ alkyl group", and examples thereof include a methylamino group, an ethylamino group, a propylamino group, an isopropylamino group, a butylamino group, an isobutylamino group, a tert-butylamino group, a pentylamino group, a hexylamino group, a heptylamino group, an octylamino group, a nonylamino group, a decylamino group, an undecylamino group, a dodecylamino group, a tridecylamino group, a tetradecylamino group, a pentadecylamino group, a hexadecylamino group, a heptadecylamino group, an octadecylamino group, a nonadecylamino group, an eicosylamino group, a heneicosylamino group, a docosylamino group and the like.

Examples of the "$C_{1-6}$ alkylamino group" include a methylamino group, an ethylamino group, a propylamino group, an isopropylamino group, a butylamino group, an isobutylamino group, a tert-butylamino group, a pentylamino group and a hexylamino group.

Examples of the "halogen atom" include a chlorine atom, a bromine atom, a fluorine atom and an iodine atom.

Each substituent in the above-mentioned formula (I) is explained in the following.

X and Y are each independently $OR^1$ or $NHR^2$ wherein $R^1$ and $R^2$ are each independently a hydrogen atom or a $C_{1-22}$ alkyl group.

The "$C_{1-22}$ alkyl group" for $R^1$ or $R^2$ is preferably a $C_{1-6}$ alkyl group, more preferably a methyl group, an ethyl group or an isopropyl group, still more preferably an ethyl group.

X is preferably $OR^1$ wherein $R^1$ is as defined above; more preferably $OR^{1'}$ wherein $R^{1'}$ is a hydrogen atom or a $C_{1-6}$ alkyl group (preferably, methyl group, ethyl group, isopropyl group); more preferably a hydroxyl group, a methoxy group, an ethoxy group or an isopropoxy group, more preferably a hydroxyl group or a methoxy group.

Y is preferably $OR^1$ wherein $R^1$ is as defined above, more preferably $OR^{1'}$ wherein $R^{1'}$ is as defined above, further more preferably a hydroxyl group, a methoxy group, an ethoxy group or an isopropoxy group, still more preferably a hydroxyl group or a methoxy group.

Z is a hydrogen atom or a $C_{1-22}$ alkyl group.

The "$C_{1-22}$ alkyl group" for Z is preferably a $C_{1-6}$ alkyl group, more preferably a methyl group. Z is preferably a hydrogen atom or a $C_{1-6}$ alkyl group, more preferably a hydrogen atom or a methyl group.

W is a $C_{1-22}$ alkyl group, a $C_{1-22}$ alkoxy group or a $C_{1-22}$ alkylamino group.

The "$C_{1-22}$ alkyl group" for W is preferably a $C_{1-16}$ alkyl group, more preferably a methyl group, a nonyl group or a pentadecyl group, still more preferably a methyl group.

The "$C_{1-22}$ alkoxy group" for W is preferably a $C_{1-6}$ alkoxy group, more preferably a tert-butoxy group.

The "$C_{1-22}$ alkylamino group" for W is preferably a $C_{1-6}$ alkylamino group.

W is preferably a $C_{1-22}$ alkyl group or a $C_{1-22}$ alkoxy group, more preferably a $C_{1-16}$ alkyl group or a $C_{1-6}$ alkoxy group, still more preferably a methyl group, a nonyl group, a pentadecyl group or a tert-butoxy group, particularly preferably a methyl group or a tert-butoxy group.

As the cysteine derivative represented by the formula (I), specifically, N-acetyl-2-methylthiazolidine-2,4-dicarboxylic acid, and N-acetyl-2-methylthiazolidine-2,4-dicarboxylic acid 2-ethyl ester are preferable, and N-acetyl-2-methylthiazolidine-2,4-dicarboxylic acid 2-ethyl ester is more preferable.

While the cysteine derivative of the present invention contains (2R,4R)-form, (2S,4S)-form, (2R,4S)-form and (2S,4R)-form based on the asymmetric carbon atoms at the 2-position and 4-position of the thiazolidine ring, all such isomers and mixtures thereof are encompassed in the cysteine derivative of the present invention. In the present specification, (2R,4R)-form, (2S,4S)-form and a mixture thereof are referred to as the cis form, and (2R,4S)-form, (2S,4R)-form and a mixture thereof are sometimes referred to as the trans form.

The cysteine derivative of the present invention is preferably a trans form from the aspect of stability. Particularly, the trans form of the cysteine derivative of the present invention is superior in the preservation stability under acidic conditions (e.g., pH 5 or below (preferably pH 4 or below)), and therefore, is highly useful when added to cosmetic agents such as a whitening agent and the like having such pH.

The cysteine derivative of the present invention is preferably a (2R,4S)-form, a (2S,4R)-form, or a mixture thereof, more preferably a (2S,4R)-form.

Examples of the salt of the cysteine derivative include salts with an inorganic base and salts with an organic base.

Examples of the salt with an inorganic base include sodium salt, potassium salt, calcium salt, magnesium salt, zinc salt, silver salt, ammonium salt and the like.

Examples of the salt with an organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine, amino acid (arginine, lysine etc.) and the like.

Each salt can be obtained by reacting the cysteine derivative of the present invention with an inorganic base or an organic base according to a method known per se.

Since the cysteine derivative of the present invention and a salt thereof have an eumelanin production suppressing effect, they themselves have a whitening effect, and can be used as an eumelanin production suppressive agent, a whitening agent, or a pigmented spot-preventing or therapeutic agent. The whitening agent in the present invention is a concept including a pigmented spot prophylactive or therapeutic agent. These applications utilize properties of the cysteine derivative of the present invention, where it maintains a stable dosage form but is decomposed into cysteine comparatively rapidly due to an enzyme such as acylase and the like at an action site via skin absorption. In the human pigment cell (melanocyte) present in the skin, L-cysteine and L-tyrosine are utilized to produce melanin. When L-tyrosine which is a raw material of eumelanin is utilized in a larger amount during melanin synthesis, production of eumelanin is promoted to make the skin darker. On the other hand, when L-cysteine is utilized in a larger amount during melanin synthesis, production of eumelanin is suppressed, and the skin becomes closer to yellow. Therefore, supply of L-cysteine during melanin synthesis suppresses production of eumelanin.

In the present invention, while the lower limit of the aforementioned cysteine derivative or a salt thereof when added to a cosmetic agent is not particularly limited as long as the effect thereof is exerted, it is preferably 0.0001 wt %. For a sufficient effect to be exhibited, it is more preferably 0.001 wt %, further more preferably 0.01 wt %, still more preferably 0.1 wt %, especially preferably 0.5 wt %, particularly preferably 1.0 wt %. When a salt of the cysteine derivative is used, the weight of the cysteine derivative moiety (free form) is set to fall within the above-mentioned range.

In the present invention, while the upper limit of the aforementioned cysteine derivative or a salt thereof when added to a cosmetic agent is not particularly limited as long as the effect thereof is exerted, it is preferably 20 wt %. It is more preferably 18 wt %, further preferably 16 wt %, still more preferably 12 wt %, especially preferably 10 wt %, particularly preferably 5 wt %. When a salt of the cysteine derivative is used, the weight of the cysteine derivative moiety (free form) is set to fall within the above-mentioned range.

The production method of the cysteine derivative represented by the above-mentioned formula (I) (hereinafter sometimes to be abbreviated as cysteine derivative (I)) is not particularly limited and known methods can be combined for the production. Specifically, the synthesis is carried out by the following method, but the method is not limited thereto.

Compound (IV) which is a precursor of cysteine derivative (I) can be synthesized according to the following Step 1, and then cysteine derivative (I) can be synthesized by Step 2. Compound (IV) may or may not be purified as necessary.

Step 1

Method of obtaining compound (IV) by reacting cysteine, or a compound represented by the formula (II) (hereinafter to be abbreviated as compound (II), the same for compounds represented by other formulas), which is obtained by subjecting cysteine to esterification or amidation in advance, with compound (III) and forming a ring

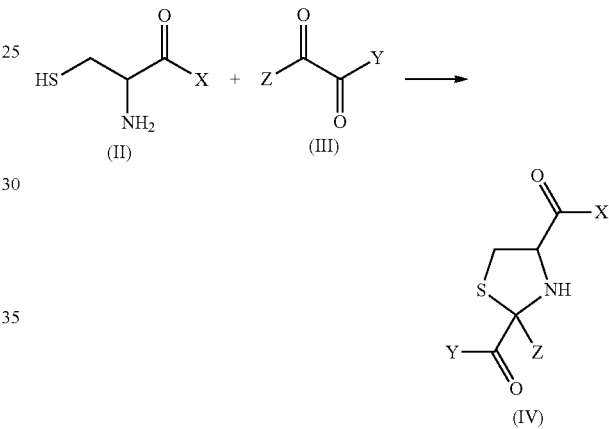

wherein each symbol is as defined above.

Compound (IV) is obtained by reacting compound (II) with compound (III) in water or an alcohol such as methanol, ethanol and the like for 5-24 hr. Of compound (II), cysteine ethyl ester can be obtained, for example, by reacting cysteine in the presence of hydrochloric acid or thionyl chloride, in ethyl alcohol, at room temperature for about 5-24 hr. Of compound (II), cysteinamide is obtained by reacting a protected cysteine with an amine in the presence of a dehydrating condensing agent such as EDCI HCl (1-ethyl-3-(3-dimethylaminopropyl)-carbodiimide hydrochloride), in a solvent such as methylene chloride and N,N-dimethylformamide (DMF), at room temperature for 5-24 hr, and then deprotecting the obtained compound.

Step 2

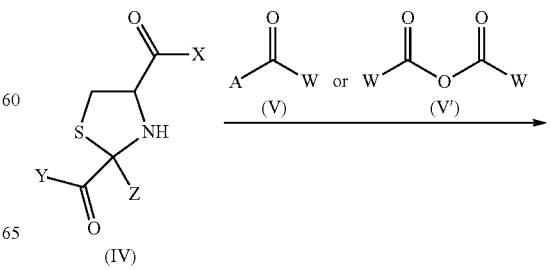

-continued

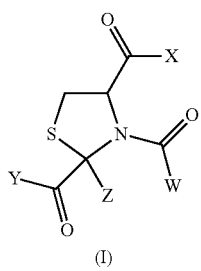

(I)

wherein A is a halogen atom, and other symbols are as defined above.

Cysteine derivative (I) can be synthesized by reacting compound (IV) with compound (V) or compound (V') in the presence or absence of a solvent, in the presence or absence of a base. Examples of the solvent include THF (tetrahydrofuran), ethyl acetate, isopropyl acetate, acetonitrile, acetone, ethanol, methanol, dichloromethane, water, a mixture thereof, and the like, and THF, ethyl acetate, isopropyl acetate, acetonitrile, acetone, dichloromethane, water, and a mixture thereof are preferable. Examples of the base include organic bases such as triethylamine, diisopropylethylamine, pyridine, N-methylmorpholine and the like, inorganic bases such as lithium hydroxide, sodium hydroxide, potassium hydroxide, sodium carbonate, potassium carbonate, sodium acetate, potassium acetate and the like, and triethylamine, diisopropylethylamine, pyridine, N-methylmorpholine, potassium carbonate, sodium carbonate are preferable.

The amount of compound (V) or compound (V') to be used is 1.0-5.0 mol, preferably 1.2-3.0 mol, per 1 mol of compound (IV). When a base is used, the amount of the base to be used is 1.0-5.0 mol, preferably 1.2-4.0 mol, per 1 mol of compound (IV). The reaction temperature is −10-100° C., preferably 0-90° C. The reaction time is 1 hr-48 hr, preferably 3 hr-20 hr.

Cysteine derivative (I) may be converted to other cysteine derivative (I) by esterification, amidation, hydrolysis or acid anhydride formation or the like.

[(B) A Whitening Agent]

Examples of the whitening agent as component (B) in the present invention include one or more kinds selected from hydroquinone and a derivative thereof, ascorbic acid and a derivative thereof, kojic acid and a derivative thereof, nicotinic acid derivative, serotonin derivative, salicylic acid derivative, astaxanthin, α-lipoic acid, calcium pantetheine sulfonate, an extract having a whitening effect, a plant extract having a whitening effect, polyphenol having a whitening effect, unsaturated fatty acid having a whitening effect, peptide having a whitening effect, amino acid having a whitening effect, a nucleic acid derivative having a whitening effect, and alkylphenol having a whitening effect.

As hydroquinone and a derivative thereof, hydroquinone, arbutin, hydroquinone glycoside are preferably used and examples thereof include hexose glycosides such as hydroquinone-α-D-glucose, hydroquinone-β-D-glucose, hydroquinone-α-L-glucose, hydroquinone-β-L-glucose, hydroquinone-α-D-galactose, hydroquinone-β-D-galactose, hydroquinone-α-L-galactose, hydroquinone-β-L-galactose and the like; pentose glycoside such as hydroquinone-α-D-ribose, hydroquinone-β-D-ribose, hydroquinone-α-L-ribose, hydroquinone-β-L-ribose, hydroquinone-α-D-arabinose, hydroquinone-β-D-arabinose, hydroquinone-α-L-arabinose, hydroquinone-β-L-arabinose and the like; aminoglycosides such as hydroquinone-α-D-glucosamine, hydroquinone-β-D-glucosamine, hydroquinone-α-L-glucosamine, hydroquinone-β-L-glucosamine, hydroquinone-α-D-galactosamine, hydroquinone-β-D-galactosamine, hydroquinone-α-L-galactosamine, hydroquinone-β-L-galactosamine and the like; uronic acid glycosides such as hydroquinone-α-D-glucuronic acid, hydroquinone-β-D-glucuronic acid, hydroquinone-α-L-glucuronic acid, hydroquinone-β-L-glucuronic acid, hydroquinone-α-D-galacturonic acid, hydroquinone-β-D-galacturonic acid, hydroquinone-α-L-galacturonic acid, hydroquinone-β-L-galacturonic acid and the like, and the like.

Examples of ascorbic acid and a derivative thereof include ascorbic acid, L-ascorbic acid esters such as L-ascorbic acid 2-phosphate, L-ascorbic acid 2-sulfate and the like; L-ascorbic acid glucosides such as L-ascorbic acid 2-glucoside, L-ascorbic acid 5-glucoside and the like; L-ascorbic acid ethers such as 3-o-ethyl ascorbyl ether, 3-o-cetyl ascorbyl ether and the like; and the like. These may be in the form of a salt. Examples of the salt include alkali metal salts such as lithium salt, sodium salt, potassium salt and the like; alkaline earth metal salts such as calcium salt, magnesium salt and the like; ammonium salts such as methylamine salt, diethylamine salt, trimethylamine salt, triethylamine salt, ethanolamine salt, diethanolamine salt, triethanolamine salt, ethylenediamine salt, tris(hydroxymethyl)methylamine salt, dicyclohexylamine salt, N,N'-dibenzylethylenediamine salt, alkanolamine salt and the like; basic organic salts and the like. Preferred are, for example, sodium salt, potassium salt, magnesium salt, triethanolamine salt and the like.

Examples of kojic acid and a derivative thereof include kojic acid and kojic acid dipalmitate and the like.

Examples of the nicotinic acid derivative include nicotinic acid amide and the like.

Examples of the serotonin derivative include coumaroylserotonin and feruloylserotonin and the like.

Examples of the salicylic acid derivative include 3-methoxysalicylic acid, 4-methoxysalicylic acid, 5-methoxysalicylic acid and a salt thereof and the like.

Examples of the extract having a whitening effect include apricot extract, wheat germ extract, acerola extract, gentian extract, bergenia crassifolia (linne) fritsch extract, oil-soluble glycyrrhiza extract, asiasarum root extract, linseed extract, watercress extract, peony root extract, (Japanese) angelica root extract, burnet extract, *aesculus hippocastanum* (horse chestnut) bark extract, *polygonum* bistorta extract, sophora angustifolia extract, *scutellaria baicalensis extract, polygonum* cuspidatum extract, raspberry extract (raspberry ketone glucoside), (white) birch extract, platycodon grandiflorum root extract and chamomilla recutita extract, yeast extract, placental extract and the like.

Examples of the plant extract having a whitening effect include plant extracts such as safflower extract, safflower seed extract, elder extract, magnolia extract, daisy extract, brown algae extract, rose fruit extract, pyracantha fortuneana (fruit) extract, persimmon tannin extract, *ginkgo biloba* leaf extract, black currant extract, black tea extract, green tea extract, oolong tea extract, tamarindus indica extract, aspalathus linearis extract, mulberry bark extract, magnolia bark extract, dioscorea composita extract, rice bran extract, persicae semen extract and saxifraga sarmentosa extract and the like.

Examples of polyphenol having a whitening effect include polyphenol such as ellagic acid, gallic acid, pentagalloylglucose, resveratrol, glabridin, glabrene, resorcin and a derivative thereof and the like.

Examples of unsaturated fatty acid having a whitening effect include linolenic acid and linoleic acid and the like.

Examples of peptide having a whitening effect include glutathione (GSH), collagen peptide and the like.

Examples of amino acid having a whitening effect include tyrosine derivatives such as N-acetyl L-tyrosine and the like, amino acids such as N-acetyl L-cysteine, ergothioneine and tranexamic acid (t-AMCHA) and the like, and the like.

Examples of alkylphenol having a whitening effect include retinol (4-n-butylresorcinol), magnolignan, biphenyl compound, rhododenol, and a derivative thereof and the like.

Examples of the nucleic acid derivative having a whitening effect include adenosine monophosphate and the like.

As preferable component (B), one or more kinds selected from hydroquinone and a derivative thereof, ascorbic acid and a derivative thereof, kojic acid and a derivative thereof, salicylic acid derivative, an extract having a whitening effect, a plant extract having a whitening effect, polyphenol having a whitening effect, unsaturated fatty acid having a whitening effect, peptide having a whitening effect, amino acid having a whitening effect, and alkylphenol having a whitening effect can be mentioned since they show a particularly superior whitening effect or superior safety. Among these, arbutin, cetyl ascorbyl ether, kojic acid, 4-methoxy salicylic acid, chamomilla recutita extract, ellagic acid, linoleic acid, glutathione, tranexamic acid or rcinol is more preferable.

The whitening agent for component (B) may be used alone or two or more kinds thereof may be mixed and used.

While the lower limit of component (B) when added to a cosmetic agent is not particularly limited as long as the effect thereof is exerted, it is preferably 0.0001 wt %. It is more preferably 0.001 wt %, further preferably 0.01 wt %, still more preferably 0.1 wt %, especially preferably 0.5 wt %, particularly preferably 1 wt %, since an advantageous effect can be exerted.

While the upper limit of component (B) when added to a cosmetic agent is not particularly limited as long as the effect thereof is exerted, it is preferably 20 wt %. It is more preferably 18 wt %, further preferably 16 wt %, still more preferably 12 wt %, especially preferably 10 wt %, particularly preferably 5 wt %.

While the mixing ratio of (A) the cysteine derivative or a salt thereof and (B) the whitening agent is not particularly limited as long as the effect thereof is exerted, it is (A)/(B) =1/20-5000/1 (g/g), preferably 1/10-2500/1 (g/g), more preferably 1/2-2500/1 (g/g), still more preferably 3/1-2500/1 (g/g). When a salt of cysteine derivative is used, the above-mentioned ratio is calculated based on the weight of the cysteine derivative moiety (free form).

In the present invention, a cosmetic agent is a concept also including quasi-drugs. While the form thereof is not particularly limited, it can take any form such as liquid, paste, gel, solid, powder, foam, jelly and the like. Specifically, for example, skin toner, lotion, cream, milky lotion, essence, shampoo, hair rinse, hair conditioner, hair mousse, hair gel, hair wax, foundation, eyeliner, eyebrow pencil, mascara, eyeshadow, blush, chapstick, lipstick, face powder, powder, facial pack, facial mask, perfume, cologne, cleansing foam, facial cleanser, cleansing foam, cleansing oil, cleansing gel, cleansing milk, dentifrice, soap, aerosol, bath preparation, hair tonic, sun protectant (sunscreen cosmetic) and the like can be mentioned.

The cosmetic agent of the present invention may contain, in addition to the above-mentioned (A) and (B), various components generally usable for cosmetic agents (including pharmaceutical external preparation, quasi-drug), within the range not inhibiting the effect of the invention. For example, oily component, surfactant, amino acids, amino acid derivatives, lower alcohol, higher alcohol, polyvalent alcohol, sugar alcohol and, alkylene oxide adduct thereof, water-soluble polymer, gelling agent, humectant, disinfectant and antimicrobial agent, anti-inflammatory agent, analgesic, antifungal agent, stratum corneum softening and peeling agent, skin colorant, hormone, ultraviolet ray absorbent, hair growth promoting product, antiperspirant and astringent active ingredient, perspiration deodorant, vitamin, blood flow enhancing agent (vasodilator, blood circulation promoter), crude drug, pH adjuster, sequestrant, viscosity modifier, pearlescent agent, natural perfume, synthetic perfume, dye, pigment, antioxidant, preservative, emulsifier, fat and wax, silicone compound, balm and the like can be mentioned.

Examples of the oily component include saturated or unsaturated fatty acids such as heptanoic acid, octanoic acid, nonanoic acid, decanoic acid, pentadecanoic acid, heptadecanoic acid, nonadecanoic acid, lauric acid, myristic acid, palmitic acid, stearic acid, arachidonic acid, behenic acid and the like; higher alcohols obtained from said saturated or unsaturated fatty acids; esters of straight chain or branched chain fatty alcohols such as octyldodecyl lactate, octyldodecyl ricinoleate, myristyl myristate, myristyl palmitate, myristyl stearate, myristyl isostearate, myristyl oleate, myristyl behenate, myristyl eruciate, cetyl ethylhexanoate, cetyl capriate, cetyl myristate, cetyl palmitate, cetyl stearate, cetyl isostearate, cetyl oleate, cetyl behenate, cetyl eruciate, stearyl myristate, stearyl palmitate, stearyl stearate, stearyl hydroxystearate, stearyl isostearate, stearyl oleate, stearyl behenate, stearyl erucate, isostearyl myristate, isostearyl palmitate, isostearyl stearate, isostearyl hydroxystearate, isostearyl isostearate, isostearyl oleate, isostearyl behenate, isostearyl eruciate, behenyl myristate, behenyl palmitate, behenyl stearate, behenyl isostearate, behenyl oleate, behenyl behenate, behenyl eruciate, erucyl myristate, erucyl palmitate, erucyl stearate, erucyl isostearate, erucyl oleate, erucyl behenate, erucyl erucate, cholesteryl nonanoate, cetearyl nonanoate and the like; esters of amino acids such as di(cholesteryl/behenyl/octyldodecyl)lauroyl glutamate, di(cholesteryl/octyldodecyl)lauroyl glutamate, di(phytosteryl/octyldodecyl)lauroyl glutamate, di(octyldodecyl/phytosteryl/behenyl)lauroyl glutamate, isopropyl lauroyl sarcocinate, (phytosteryl/decyltetradecyl)myristoyl methyl β alaninate and the like (e.g., "ELDEW" PS-203, PS-304, PS-306, APS-307, SL-205 manufactured by Ajinomoto Co., Inc.); esters of dimer acids such as (phytosteryl/isostearyl/cetyl/stearyl/behenyl)dimer dilinoleate, bis(behenyl/isostearyl/phytosteryl)dimer dilinoleyl dimer dilinoleate, dimer dilinoleyl hydrogenated rosinate, dimer dilinoleyl diisostearate, bis(lauroyl glutamate/lauroyl sarcosinate)dimer dilinoleyl and the like; squalane, squalene, castor oil and/or hydrogenated castor oil and a derivative thereof; glycerides such as hydroxystearic acid monoglyceride, hydroxystearic acid diglycerides, isostearic acid monoglyceride, isostearic acid diglycerides, oleic acid monoglyceride, oleic acid diglycerides, ricinoleic acid monoglyceride, ricinoleic acid diglycerides, linoleic acid monoglyceride, linoleic acid diglycerides, linolenic acid monoglyceride, linolenic acid diglycerides, tartaric acid monoglyceride, tartaric acid diglycerides, citric acid monoglyceride, citric acid diglycerides, malic acid monoglyceride, malic acid diglycerides and ethylene oxide 1-30 molar adducts of these glycerides and the like; lanolins including beeswax, liquid and purified lanolin, and a derivative thereof; oily raw materials derived from animals and plants such as shea butter, flaxseed oil, camellia oil, almond oil, avocado oil, olive oil, rape seed oil, safflower oil, soybean oil, peanut oil, coconut oil, *macadamia* nut oil, jojoba oil, cinnamon oil, grape oil, corn oil, sunflower oil, sasanqua oil, rice bran oil, rice germ oil, wheat germ oil, apricot kernel oil, tea oil, carnauba wax, sesame oil, cottonseed oil, cacao oil, rape seed oil, evening primrose oil, palm oil, palm oil, palm kernel oil, hydrogenated palm oil, mink oil, beef tallow, lard, Japan wax, candelilla wax, spermaceti wax and the like; oily raw materials derived from petroleum and mineral such as paraffin, isoparaffin, octane, decane, dodecane, isododecane, hexadecane, isohexadecane, microcrystalline wax, liquid paraffin, petrolatum, ceresin and the like; silicones such as silicone polymers such as methylpolysiloxane, dimethylpolysiloxane, cyclomethicone, polyoxyethylene-methyl polysiloxane, polyoxypropylene-methyl polyoxysiloxane, poly (oxyethylene, oxypropylene)-methyl polysiloxane, methyl phenyl polysiloxane, fatty acid-denatured polysiloxane, aliphatic alcohol-denatured polysiloxane, amino acid-denatured polysiloxane and the like, and the like; resin acid, fatty acid ester, ketones and the like.

Examples of the surfactant include anionic surfactant, non-ionic surfactant, cationic surfactant and amphoteric surfactant and the like. Examples of the anionic surfactant include N-long chain acyl amino acid salts such as N-long chain acyl acidic amino acid salt (e.g., N-long chain acyl glutamic acid salt, N-long chain acyl aspartic acid salt and the like), N-long chain acyl neutral amino acid salt (e.g., N-long chain acyl glycine salt, N-long chain acyl alaninine salt, N-long chain acyl threonine salt and N-long chain acyl sarcosine salt and the like) and the like (e.g., "AMISOFT" CT-12, LT-12, CK-22, CS-22, CS-11, CK-11, LS-11, LK-11, MS-11, MK-11, GS-11, HS-11, CA, LA-D, "AMINOSOAP" AR-12, "AMILITE" GCK-12, GCK-11, GCS-11, ACT-12 manufactured by Ajinomoto Co., Inc.), N-long chain fatty acid acyl-N-methyl taurine salts, alkyl sulfate and alkylene oxide adduct thereof, fatty acid amide ether sulfate, fatty acid metal salt, weak base and amino acid salt, sulfosuccinic acid type surfactant, alkyl phosphate and alkylene oxide adduct thereof, higher alkyl sulfate salt, alkyl ether sulfate salt, hydroxy alkyl ether carboxylate, alkyl ether carboxylate and the like; examples of the non-ionic surfactant include ether-type surfactant (e.g., glycerol ether and alkylene oxide adduct thereof and the like), ester-type surfactant (e.g., glycerol ester and alkylene oxide adduct thereof and the like), ether ester-type surfactant (e.g., sorbitan ester and alkylene oxide adduct thereof and the like), fatty acid alkylolamide (e.g., fatty acid monoethanolamide, fatty acid diethanolamide and the like), ester-type surfactant (e.g., polyoxyalkylene fatty acid ester, polyoxyalkylene polyvalent alcohol fatty acid ester, polyoxyalkylene sorbitan fatty acid ester, polyoxyalkylene hydrogenated castor oil, glycerol monostearate, glycerol ester, fatty acid polyglycerol ester, acyl amino acid polyglycerol ester, sorbitan ester, sucrose fatty acid ester and the like), nitrogen-containing type non-ionic surfactant (e.g., alkyl glucosides, hydrogenated castor oil pyroglutamic acid diester and ethylene oxide adduct thereof, and fatty acid alkanolamide and the like) and the like; examples of the cationic surfactant include aliphatic amine salt (e.g., alkyl ammonium chloride, dialkyl ammonium chloride, alkyl trimethyl ammonium chloride (C16-C22), dialkyl dimethyl ammonium methosulfate salt and the like), aromatic quaternary ammonium salt (e.g., quaternary ammonium salt, benzalkonium salt and the like of the aforementioned aliphatic amine salt), fatty acid acyl arginine ester, N-long chain acyl arginine ethyl pyrrolidone carboxylic acid salt, amideamines, stearamidepropyl dimethylamine glutamic acid salt, stearamidepropyl dimethylamine lactic acid salt, stearamidopropyl dimethylamine pyrrolidone carboxylic acid salt, behenamidopropyl dimethylamine glutamic acid salt, behenamidopropyl dimethylamine lactic acid salt, behenamidopropyl dimethylamine pyrrolidone carboxylic acid salt and the like; and examples of the amphoteric surfactant include betaine type surfactant (e.g., alkyl betaine, alkylamide betaine, sulfobetaine, imidazolium betaine, aminopropionate, carboxybetaine and the like), N-long chain acyl arginine, N-(3-alkyl(12,14)oxy-2-hydroxypropyl)arginine hydrochloride, aminocarboxylic acid type surfactant, imidazoline type surfactant and the like.

Examples of the amino acids include arginine, lysine, glutamic acid, aspartic acid, valine, leucine, isoleucine, serine, glycine, alanine, proline, hydroxyproline, threonine, histidine, phenylalanine, tryptophan, tyrosine, glutamine, asparagine, cysteine, cystine, pyrrolidone carboxylic acid, methionine and salts thereof.

Examples of the amino acid derivative include pyrrolidone carboxylic acid and a salt thereof, trimethylglycine, lauroyllysine and the like.

Examples of the lower alcohol include ethanol, propanol, isopropanol, butanol and the like.

Examples of the higher alcohol include cetyl alcohol, lauryl alcohol, isostearyl alcohol, stearyl alcohol, oleyl alcohol, myristyl alcohol, octyldodecanol, behenyl alcohol, lanolin alcohol, cetostearyl alcohol, decyltetradecanol, hexyldecanol, cholesterol, phytosterol and the like.

Examples of the polyvalent alcohol include glycerol, diglycerol, ethylene glycol, 1,3-butylene glycol, propylene glycol, dipropylene glycol, isoprene glycol and the like.

Examples of the sugar alcohol and alkylene oxide adduct thereof include mannitol, erythritol and the like.

Examples of the water-soluble polymer include polyamino acid comprising polyglutamic acid, polyaspartic acid and a salt thereof, polyethylene glycol, high polymerized polyethylene glycol, gum arabics, alginates, xanthan gum, hyaluronic acid, hyaluronic acid salt, chitin, chitosan, water-soluble chitin, pectin, mannan, carrageenan, gellan gum, quince seed, guar gum, carboxy vinyl polymer, carboxymethylcellulose, hydroxymethyl cellulose, hydroxyethyl cellulose, hydroxypropylcellulose, hydroxypropyl methylcellulose, hydroxypropyl starch phosphericacid, polyacrylamide, polyvinyl alcohol, polyvinylpyrrolidone, hydroxypropyl trimethyl ammonium chloride, polydimethylmethylenepiperidium chloride, polyvinylpyrrolidone derivative quaternary ammonium, acrylic acid copolymer, cationated protein, collagen decomposition product and a derivative thereof, acylated protein, dextrin palmitic acid ester, aluminum stearate, polyglycerol, dibenzylidenesorbitol, 12-hydroxy stearic acid and the like.

Examples of the gelling agent include N-2-ethylhexanoyl-L-glutamic acid dibutylamide, N-lauroyl-L-glutamic acid dibutylamide (for example, GP-1, EB-21 manufactured by Ajinomoto Co., Inc.) and the like.

Examples of the humectant include glycerol, diglycerol, dipropyleneglycol, 1,3-butyleneglycol, polyethylene glycol, hyaluronic acid, hyaluronic acid salt, chondroitin sulfate, chondroitin sulfate salt, honey, collagen, urea, sodium DL-pyrrolidonecarboxylate/L-pyrrolidone carboxylic acid mixed solution (AJIDEW NL-50), di(phytosteryl/2-octyldodecyl) N-lauroyl-L-glutamate, 1,3-pentanediol, 1,3-propanediol and the like.

Examples of the disinfectant and antimicrobial agent include 4-hydroxybenzoic acid and a salt thereof and ester thereof, triclosan, chlorhexidine, phenoxyethanol, menthol, mint oil, glyceryl caprate, glyceryl caprylate, salicylic acid-N-alkyl amide, DL-pyrrolidone carboxylic acid ethyl N-cocoyl L-arginate, benzalkonium chloride, isopropyl methyl phenol and the like.

Examples of the anti-inflammatory agent, analgesic, antifungal agent, stratum corneum softening and peeling agent, skin colorant and hormone include aloe extract, lily extract, hinokitiol, hydrocortisone(V), ε-aminocarboxylic acid, azulene, allantoin, glycyrrhizic acids, glycyrrhizic acid derivative, β-glycyrrhetinic acid and the like.

The ultraviolet ray absorbent is, for example, an organic substance (photoprotective filter) which is liquid or crystal at room temperature, and can absorb ultraviolet rays and release the absorbed energy as radiation having a longer wavelength (e.g., heat). Examples thereof include UV-B filter and UV-A filter. The UV-B filter can be oil-soluble or water-soluble. Examples of the oil-soluble substance include 3-benzylidene camphor or 3-benzylidene norcamphor and a to derivative thereof (e.g., 3-(4-methyl benzylidene)-camphor); 4-aminobenzoic acid derivative (preferably 4-(dimethylamino)-benzoic acid-2-ethylhexyl ester, 4-(dimethylamino)-benzoic acid-2-octyl ester, 4-(dimethylamino)-benzoic acid pentyl ester); cinnamic acid ester (preferably 4-methoxy cinnamic acid-2-ethylhexyl ester, 4-methoxy cinnamic acid propyl ester, 4-methoxy cinnamic acid isopropyl ester, 4-methoxy cinnamic acid isopentyl ester, 2-cyano-3,3-phenyl cinnamic acid-2-ethylhexyl ester (Octocrylene)); salicylic acid ester (preferably salicylic acid-2-ethylhexyl ester, salicylic acid-4-isopropylbenzyl ester, salicylic acid homomethyl ester); benzophenone derivative (preferably 2-hydroxy-4-methoxy benzophenone, 2-hydroxy-4-methoxy-4'-methyl benzophenone, 2,2'-dihydroxy-4-methoxy benzophenone); benzalmalonic acid ester (preferably 4-methoxy benzalmalonic acid di-2-ethylhexyl ester); triazine derivative (e.g., 2,4,6-trianilino-(p-carbo-2'-ethyl-1'-hexyloxy)-1,3,5-triazine, octyl triazone, dioctyl butamido triazone [Uvasorb (registered trade mark) HEB]); propane-1,3-dione (e.g., 1-(4-t-butylphenyl)-3-(4'-methoxyphenyl)-propane-1,3-dione); ketotricyclo(5.2.1.0) decane derivative and the like. Examples of the water-soluble substance include 2-phenyl benzimidazole-5-sulfonic acid and alkali metal salt, alkaline earth metal salt, ammonium salt, alkylammonium salt, alkanol ammonium salt and glucammonium salt thereof; sulfonic acid derivative of benzophenone (preferably 2-hydroxy-4-methoxy benzophenone-5-sulfonic acid and a salt thereof); sulfonic acid derivative of 3-benzylidene camphor (e.g., 4-(2-oxo-3-bornylidenemethyl)-benzene sulfonic acid and 2-methyl-5-(2-oxo-3-bornylidene)-sulfonic acid and a salt thereof and the like. As the UV-A filter, a benzoyl methane derivative is particularly used and, for example, 1-(4'-t-butylphenyl)-3-(4'-methoxyphenyl)-propane-1,3-dione, 4-t-butyl-4'-methoxydibenzoylmethane (Parsol (registered trade mark) 1789), 1-phenyl-3-(4'-isopropylphenyl)-propane-1,3-dione, enamine compound, 4-methoxydibenzoylmethane, 4-t-butyl-4'-methoxydibenzoylmethane can be mentioned. In addition, titanium oxide, zinc oxide, octyl methoxycinnamate, 2-ethylhexyl dimethoxybenzylidene dioxoimidazolidine propionate and the like can be mentioned.

Examples of the hair growth promoting product include pantothenic acid and a derivative thereof, allantoin, biotin, mononitro guaiacol, adenosine, pentadecanoic acid glyceride, dialkyl monoamine derivative, coleus extract, chlorophyll, photosensitizer, estradiol, ethynylestradiol, pyridoxine hydrochloride, thioxolone, sulfur, organic sulfur substance and the like.

Examples of the antiperspirant and astringent active ingredient, and perspiration deodorant include salts of aluminum, zirconium and zinc such as aluminum chloride, aluminum chlorohydrate, aluminum zirconium trichlorohydrate, aluminum zirconium tetrachlorohydrate, zinc pyrrolidone carboxylate and the like.

Examples of the vitamin include vitamins A, $B_1$, $B_2$, $B_6$, E and derivatives thereof and the like.

Examples of the blood flow enhancing agent include *swertia* herba extract, cepharanthine, vitamin E and a derivative thereof and a salt thereof, garlic extract, ginseng extract, aloe extract, gentiana extract, carpronium chloride, minoxidil, citrus junos extract, althea extract, γ-oryzanol, zinc L-pyrrolidone carboxylate, DL-pyrrolidone carboxylic acid, sodium DL-pyrrolidone carboxylate solution, sodium DL-pyrrolidone carboxylate/L-pyrrolidone carboxylic acid mixed solution (AJIDEW NL-50), capsaicinoid (e.g., capsaicin etc.), capsinoid (e.g., dihydrocapsiate etc.) and the like.

Examples of the pH adjuster include citric acid, adipic acid, phosphoric acid, glutamic acid, lactic acid, sulfuric acid, hydrochloric acid, ammonium, sodium hydroxide, potassium hydroxide, arginine, γ-oryzanol and the like.

Examples of the sequestrant include edetic acid and a salt thereof, diethylenetriamine pentaacetic acid and a salt thereof, hydroxyethyl ethylenediamine triacetic acid and a salt thereof, hydroxyethane diphosphonic acid and a salt thereof, phosphoric acid, citric acid, succinic acid, gluconic acid, sodium polyphosphate, sodium metaphosphate, sodium hexametaphosphate, phytic acid, sodium pentetate and the like.

Examples of the viscosity modifier include agar, organically modified clay mineral and the like.

Examples of the pearlescent agent include alkylene glycol ester, fatty acid alkanolamide, fatty acid monoglyceride, fatty ether and the like.

Examples of the synthetic perfume include ester, ether, aldehyde, ketone, alcohol and hydrocarbon type flavor and the like.

Examples of the dye include cochineal red A (C.I.16255), patent blue (C.I.42051), chlorophyllin (C.I.75810) and the like.

Examples of the pigment include titanium oxide, mica, sericite, Nε-lauroyl-L-lysine and the like.

Examples of the antioxidant include vitamin E, vitamin E derivative and a salt thereof, sodium sulfite and the like.

Examples of the preservative include phenoxyethanol, paraben, sorbic acid, isopropyl methylphenol, benzalkonium chloride, benzoic acid, dehydroacetic acid, hexanediol, pentanediol, chlorhexidine sulfate, DL-pyrrolidone carboxylic acid ethyl N-cocoyl L-arginate and the like.

The emulsifier is, for example, a nonionic surfactant, and examples thereof include an addition resultant product of 2-30 mol of ethylene oxide and/or 0-5 mol of propylene oxide to straight chain fatty alcohol having 8 to 22 carbon atoms, fatty acid having 12 to 22 carbon atoms, alkylphenol wherein alkyl group has 8 to 15 carbon atoms, or alkylamine wherein alkyl group has 8 to 22 carbon atoms; alkyl and/or alkenyl oligoglycoside wherein alkyl(alkenyl) group has 8 to 22 carbon atoms, and an ethoxylated product thereof; ethylene oxide (1-15 mol) adduct of castor oil and/or hydrogenated castor oil; ethylene oxide (15-60 mol) adduct of castor oil and/or hydrogenated castor oil; partial ester of unsaturated straight chain or saturated branched fatty acid having 12 to 22 carbon atoms and/or hydroxycarboxylic acid having 3 to 18 carbon atoms and glycerol and/or sorbitan, and adduct thereof with 1-30 mol of ethylene oxide; partial ester of polyglycerol (2-8 average degree of self-condensation), polyethylene glycol (molecular weight 400-5000), trimethylolpropane, pentaerythritol, sugar alcohol (e.g., sorbitol), alkyl glucoside (e.g., methyl glucoside, butyl glucoside, lauryl glucoside, and C16-C18 alkylglucoside) and polyglucoside (e.g., cellulose), and saturated and/or unsaturated straight chain or branched fatty acid having 12 to 22 carbon atoms and/or hydroxycarboxylic acid having 3 to 18 carbon atoms, and adduct thereof with 1-30 mol of ethylene oxide; mixed ester of pentaerythritol, fatty acid, citric acid and fatty alcohol, and/or mixed ester of fatty acid having 6 to 22 carbon atoms, methyl glucose and polyol (preferably glycerol or polyglycerol); mono-, di-, trialkylphosphate and mono-, di- and/or tri-PEG-alkylphosphate and a salt thereof; wool wax alcohol; polysiloxane/polyalkyl/polyether copolymer and the corresponding derivative; block copolymer (e.g., polyethylene glycol-30 dipolyhydroxystearate); polymer emulsifier (e.g., Goodrich Pemulen type (TR-1, TR-2)); polyalkylene glycol, and glycerol carbonate and the like. Examples of ethylene oxide adduct include ethylene oxide of fatty alcohol, fatty acid, alkylphenol or castor oil, and examples of propylene oxide adduct include known, commercially available products. Examples of partial glyceride include hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and the like. Moreover, ethylene oxide 1-30 mol (preferably 5-10 mol) adduct of the above-mentioned partial glyceride is also suitable. Examples of sorbitan ester include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinolate, sorbitan sesquiricinolate, sorbitan diricinolate, sorbitan triricinolate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and industrial mixtures thereof. In addition, ethylene oxide 1-30 mol (preferably 5-10 mol) adduct of the above-mentioned sorbitan ester is also suitable. Examples of polyglycerol ester include polyglyceryl-2 dipolyhydroxystearate (Dehymuls (registered trade mark) PGPH), polyglyceryl-3 diisostearate (Lameform (registered trade mark) TGI), polyglyceryl-4 isostearate (Isolan (registered trade mark) GI 34), polyglyceryl-3 oleate, diisostearoyl polyglyceryl-3 diisostearate (Isolan (registered trade mark) PDI), polyglyceryl-3 methylglucose distearate (Tego Care (registered trade mark) 450), polyglyceryl-3 beeswax (Cera Bellina (registered trade mark)), polyglyceryl-4 caprate (Polyglycerol Caprate T2010/90), polyglyceryl-3 cetyl ether (Chimexane (registered trade mark) NL), polyglyceryl-3 distearate (Cremophor (registered trade mark) GS 32) and polyglyceryl polyricinolate (Admul (registered trade mark) WOL 1403), polyglyceryl dimerate isostearate, mixtures thereof and the like. Examples of polyol ester include mono-, di- and tri-ester of trimethylolpropane or pentaerythritol and lauric acid, coconut oil fatty acid, tallow fatty acid, palmitic acid, stearic acid, oleic acid, behenic acid and the like, which may be reacted with ethylene oxide (1-30 mol) where necessary, stearic acid salt, POE glycerin fatty acid ester, POE hydrogenated castor oil ester, POE sorbitan fatty acid ester, sodium N-stearoyl-L-glutamate, PEG-40 hydrogenated castor oil pyroglutamate isostearate, PEG-30 hydrogenated castor oil pyroglutamate isostearate, PEG-60 hydrogenated castor oil pyroglutamate isostearate, glycereth-25 pyroglutamate isostearate and the like.

Examples of the fat and wax include 12-hydroxystearic acid, lanolin, beeswax, candelilla wax, carnauba wax, petrolatum, solid paraffin, lanolin derivative, microcrystalline wax, ceresin, synthetic triglyceride, beeswax, Japan wax and the like.

Examples of the silicone compound include chain silicone such as dimethylpolysiloxane, methylphenylpolysiloxane, methylhydrogenpolysiloxane and the like; cyclic silicone such as octamethylcyclotetrasiloxane, decamethylcyclopentasiloxane, dodecamethylcyclohexasiloxane and the like; as well as amino-modified silicone compound, fatty acid-modified silicone compound, alcohol-modified silicone compound, polyether-modified silicone compound, epoxy-modified silicone compound, fluorine-modified silicone compound, glycoside-modified silicone compound and/or alkyl-modified silicone compound (which can be liquid or resin-like at room temperature), simethicone which is a mixture of dimethicone having an average chain length of dimethyl siloxane unit number of 200-300 and silicate hydride, and the like.

Examples of the balm include a mixture of natural and synthetic perfume. Examples of the natural perfume include plant-derived raw materials such as flower (e.g., lily, lavender, rose, jasmine, neroli, ylang-ylang, etc.), stem and leaf (e.g., geranium, patchouli, petitgrain, etc.), fruit (e.g., anise, cilantro, caraway, juniper, etc.), fruit skin (e.g., bergamot, lemon, orange, etc.), root (e.g., nutmeg, angelica, celery, cardamom, *costus*, irid, calamus, etc.), tree (e.g., pine, sandalwood, guaiac, cedar, red sandalwood, etc.), herb and grass (e.g., tarragon, lemongrass, sage, thyme, etc.), acerose leaf and branch (e.g., spruce, fir, pine, scrub pine, etc.), resin and balsam (e.g., galbanum, elemi, benzoin, myrrh, frankincense, opopanax, etc.) and the like, and animal-derived raw materials such as civet, beaver and the like. Examples of the comparatively low volatile essential oil often used as an aromatic component include sage oil, chamomile oil, clove oil, *Melissa officinalis* oil, mint oil, cinnamon leaf oil, lime flower oil, juniper berry oil, vetiver oil, frankincense oil, galbanum oil, labdanum oil and lavandin oil, bergamot oil, dihydromyrcenol, lilial, lyral, citronellol, phenylethyl alcohol, α-hexylcinnam aldehyde, geraniol, benzylacetone, cyclamenaldehyde, linalool, Boisambrene Forte, Ambroxan, indole, Hedione, Sandelice, citrus oil, mandarin oil, orange oil, allylpentyl glycholate, Cyclovertal, lavandin oil, clary oil, β-damascone, geranium oil bourbon, cyclohexyl salicylate, Vertofix Coeur, Iso-E-Super, Fixolide NP, evernyl, Iraldein gamma, phenylacetic acid, geranyl acetate, benzyl acetate, rose oxide, Romilat, Irotyl and Floramat, peppermint oil, spearmint oil, anise oil, illicium verum oil, caraway oil, eucalyptus oil, fennel oil, citrus oil, wintergreen oil, menthol and the like.

The cosmetic agent of the present invention may be used to suppress melanin production and/or whiten skin. In either method, the cosmetic agent is preferably topically applied to the skin in an amount sufficient that (A) the cysteine compound or salt thereof is applied in an amount of 0.00001 to 0.6 mg/cm$^2$ of skin, preferably 0.0001 to 0.3 mg/cm$^2$ of skin, more preferably 0.001 to 0.03 mg/cm$^2$ of skin, and (B) the whitening agent is applied in an amount of 0.00001 to 0.6 mg/cm² of skin, preferably 0.0001 to 0.3 mg/cm² of skin, more preferably 0.001 to 0.03 mg/cm² of skin.

EXAMPLES

The present invention is explained in more detail in the following by referring to Examples, which are not to be construed as limitative.

Synthesis of component A

Synthetic Example 1

N-acetyl-2-methylthiazolidine-2,4-dicarboxylic acid 2-ethyl ester (Hereinafter Sometimes to be Abbreviated as N-Ac-CP2Et in the Present Specification)

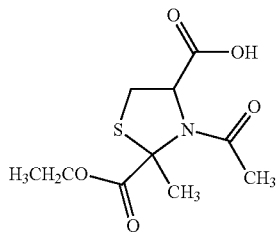

L-Cysteine hydrochloride monohydrate (100 g, 569 mmol) was dissolved in water (200 ml), and the pH of the solution was adjusted to 5.03 with 6N aqueous sodium hydroxide. The reaction mixture was heated to 40° C., ethyl pyruvate (76 ml, 684 mmol) was gradually added thereto, and the mixture was stirred at 40° C. for 3.5 hr to give 2-methylthiazolidine-2,4-dicarboxylic acid 2-ethyl ester (the ratio of trans form:cis form of the resultant product in the reaction mixture was confirmed by the area ratio of an HPLC chart to find about 55:45). After completion of the reaction, the reaction mixture was extracted with ethyl acetate. The extract was washed with saturated brine, and dried over anhydrous magnesium sulfate. To the obtained ethyl acetate solution was added triethylamine (159 ml, 1141 mmol) under argon, and acetyl chloride (61 ml, 858 mmol) was slowly added dropwise thereto. The reaction mixture was heated under reflux for 4 hr to give N-acetyl-2-methylthiazolidine-2,4-dicarboxylic acid 2-ethyl ester (the ratio of trans form:cis form of the resultant product in the reaction mixture was confirmed by the area ratio of an HPLC chart to find about 95:5). After completion of the reaction, water (300 ml) was added thereto, and the pH of the mixture was adjusted to 1.0 with HCl. The aqueous layer was separated, and the organic layer was washed with water (300 ml), washed with saturated brine, and dried over anhydrous magnesium sulfate. The obtained ethyl acetate solution was concentrated until a weight of 500 g, to the residue was added heptane to allow recrystallization of the residue, and the crystals were washed with heptane/ethyl acetate=2/1, and dried at 50° C. under reduced pressure to give the trans form (mixture of (2R,4S)-form, (2S,4R)-form) of N-acetyl-2-methylthiazolidine-2,4-dicarboxylic acid 2-ethyl ester as crystals (81 g, yield 55%).
¹H-NMR (CDCl₃): δ; 1.27 (3H, t, J=7.12 Hz), 1.94 (3H, s), 2.18 (3H, s), 3.40 (1H, d, J=11.6 Hz), 3.56 (1H, dd, J=5.5, 11.0 Hz), 4.20 (2H, t, J=7.08 Hz), 5.00 (1H, d, J=5.9 Hz), 9.10 (1H, brs).

(HPLC analysis conditions in Synthetic Example 1 and the following Synthetic Example 3)
detector; ultraviolet absorption spectrophotometer (measurement wavelength; 210 nm)
column; YMC-Pack ODS-A (particle size 5 pm, fine pore size 12 mm, inner diameter 6.0 mm, length 150 mm)
eluent; 50 mM NaH₂PO₄ (adjusted to pH2 with 85% H₃PO₄):MeOH=60:40
flow rate; 1.0 mL/min
column temperature; 40° C.
injection volume; 10 µL
retention time (min); 2-methylthiazolidine-2,4-dicarboxylic acid 2-ethyl ester (cis form): 9.0, (trans form): 8.6, N-Ac-CP2Et (cis form): 7.5, (trans form): 9.2

Synthetic Example 2

N-acetyl-2-methylthiazolidine-2,4-dicarboxylic acid (N-acetyl-cysteinylpyruvic acid; hereinafter sometimes to be abbreviated as N-Ac-CP)

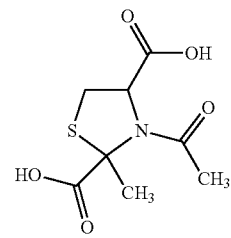

N-acetyl-2-methylthiazolidine-2,4-dicarboxylic acid 2-ethyl ester obtained by an operation similar to that in Synthetic Example 1 was dissolved in a mixed solvent of methanol (120 ml) and water (120 ml), and 2N NaOH (182.4 ml) was added thereto. The reaction mixture was heated with stirring under an argon atmosphere at 100° C. for 4 hr, and then at 80° C. overnight. The reaction mixture was allowed to cool to room temperature, and the pH was adjusted to 1-2 with AMBERLITE IR120B H AG (about 250 g). The AMBERLITE was filtered off, and the filtrate was concentrated under reduced pressure. To the residue was ethyl acetate (200 ml), the mixture was stirred for 1 hr, and the resulting white crystals were collected by filtration to give N-acetyl-2-methylthiazolidine-2,4-dicarboxylic acid (15.99 g, 75%).
¹H-NMR (DMSO-d₆): δ; 1.73 (3H, s), 2.01 (3H, s), 3.36 (2H, d, J=3.6 Hz), 5.26 (1H, t, J=3.6 Hz).
MS spectrum m/z; [M+H]⁺=234.0, [M−H]⁻=232.0.

Synthetic Example 3

(2S,4R)-N-acetyl-2-methylthiazolidine-2,4-dicarboxylic acid 2-ethyl ester (hereinafter sometimes to be abbreviated as (2S,4R)-N-Ac-CP2Et)

L-cysteine hydrochloride monohydrate (50 g, 285 mmol) was dissolved in water (100 ml), and the pH of the solution was adjusted to 5.15 with 6N aqueous sodium hydroxide. The reaction mixture was heated to 40° C., ethyl pyruvate (38 ml, 342 mmol) was gradually added thereto, and the mixture was stirred at 40° C. for 4 hr. Water was added, and the mixture was cooled to room temperature to precipitate the crystals and the crystals were collected by filtration. The obtained crystals were washed with water, and dried under reduced pressure at 50° C. to give 2-methylthiazolidine-2,4-dicarboxylic acid 2-ethyl ester (trans form:cis form=88:12, 12.1 g, yield 19%). The synthesized 2-methylthiazolidine-2,4-dicarboxylic acid 2-ethyl ester (5 g, 22.8 mmol) was dissolved in ethyl acetate (40 ml), and triethylamine (6.4 ml, 45.9 mmol) was added under argon. Acetyl chloride (2.4 ml, 33.8 mmol) was slowly added dropwise, and the mixture was stirred at room temperature overnight. After completion of the reaction, water (15 ml) was added thereto, and the pH of the mixture was adjusted to 1.0 with HCl. The aqueous layer was separated, and the organic layer was washed with water (10 ml), washed with saturated brine, and dried over anhydrous magnesium sulfate. The obtained ethyl acetate solution was concentrated to precipitate crystals. The crystals were collected by filtration, washed with heptane/ethyl acetate=1/1 (10 ml), and dried under reduced pressure at 50° C. to give (2S,4R)-N-acetyl-2-methylthiazolidine-2,4-dicarboxylic acid 2-ethyl ester as crystals (3.3 g, yield 55%).
(HPLC Analysis Conditions)
    detector; ultraviolet absorption spectrophotometer (measurement wavelength; 250 nm)
    column; CHIRALPACK QN-AX (0.46 cm*15 cm)
    eluent; MeOH:AcOH:AcONH$_4$=98:2:0.5 (V/V/W)
    flow rate; 1.0 mL/min
    column temperature; 30° C.
    injection volume; 10 μL
    retention time (min); (2S,4R)-form: 4.5, (2R,4S)-form: 5.0

Experimental Example 1

Melanin Production Rate Measurement

B16 melanoma was cultured in DMEM (Dulbecco's Modified Eagle Medium) (high glucose, containing 10% serum). After confluence, the cells were seeded on a 6 well plate. The next day, each well medium was exchanged with DMEM (300 μM tyrosine added) added with each evaluation sample at a given evaluation concentration (Table 1), and the cells were cultured for 3 days. The evaluation samples that did not dissolve in the medium were dissolved in dimethyl sulfoxide, and added to the medium (0.1% dimethyl sulfoxide was in the medium). The medium was recovered, and centrifuged at 10000 rpm for 10 min. The absorbance of the supernatant at 450 nm was measured by spectrophotometer. The medium was recovered, and the cells were rinsed once with PBS (phosphate-buffered saline). A blending solution of 4% aqueous sodium hydroxide solution and dimethyl sulfoxide (9:1) was added to the well, and the mixture was stood at room temperature for 10 min. The cells were dissolved and recovered, and centrifuged at 3500 rpm for 10 min. The absorbance (450 nm) of the supernatant was measured by spectrophotometer. The total of the melanin amount in the medium and in the cell was calculated from the analytical curve drawn using synthetic melanin. By setting the calculated value 3 days after addition of each sample at a given concentration as a relative percentage to the calculated value of the control (no sample addition) defined as 100%, the melanin production rate of each sample to the melanin amount in the control as 100% was calculated. When a sample was dissolved dimethyl sulfoxide and then added, a sample containing 0.1% dimethyl sulfoxide was used as a control (no sample addition). The melanin production rate was standardized from the amount of cell protein obtained in Experimental Example 2.

The spectrophotometer used in this melanin production suppression test was DU800, manufactured by BECKMAN COULTER.

Experimental Example 2

Cell Viability Rate Measurement

B16 melanoma was cultured in DMEM (Dulbecco's Modified Eagle Medium) (high glucose, containing 10% serum). After confluence, the cells were seeded on a 6 well plate. The next day, each well medium was exchanged with DMEM (300 μM tyrosine added) added with each evaluation sample at a given evaluation concentration (Table 1), and the cells were cultured for 3 days. The medium was recovered, and the cells were rinsed once with PBS (phosphate-buffered saline). A blending solution of 4% aqueous sodium hydroxide solution and dimethyl sulfoxide (9:1) was added to the well, and the mixture was stood at room temperature for 10 min. The cells were dissolved and recovered, and centrifuged at 3500 rpm for 10 min, and the supernatant was diluted 3-fold with milli-Q water. Solution A (DC Protein Assay; BIO RAD, 100 μl) was added to the diluted solution (20 μl) and the mixture was admixed in a vortex. Solution B (DC Protein Assay; BIO RAD, 800 μl) was added and mixed therewith, and the mixture was stood at room temperature for 15 min. After standing, the absorbance (750 nm) was measured by a spectrophotometer. In addition, the analytical curve of albumin was determined, the protein amount of the above-mentioned solution was calculated, and the relative rate was taken as a viability rate.

The spectrophotometer used in this melanin production suppression test was DU800, manufactured by BECKMAN COULTER.

The evaluated samples were obtained as follows.
    kojic acid: manufactured by SIGMA, K3125-5G
    arbutin: manufactured by SIGMA, A4256-10G
    rcinol: manufactured by Tokyo Chemical Industry Co., Ltd., 4-hexylresorcinol, H0139
    GSH: manufactured by Nacalai Tesque, glutathione (reduced type), 08786-32
    tranexamic acid: manufactured by SIGMA, trans-4-(aminomethyl)-cyclohexanecarboxylic acid, 857653-10G
    4-MS: manufactured by Tokyo Chemical Industry Co., Ltd., 4-methoxy salicylic acid, M1795
    chamomilla recutita extract: manufactured by Ichimaru Pharcos Co., Ltd., Biocellact CHAMOMILLA B
    ellagic acid: manufactured by Fulka, 45140
    cetyl ascorbyl ether: manufactured by Nikko Chemicals, VC cetyl ether (3-o-cetyl ascorbyl ether)
    linoleic acid: manufactured by Wako Pure Chemical Industries, Ltd., linoleic acid, plant-derived, 125-05821
[Evaluation]
<Melanin Production Rate: Combined Use Effect on Whitening, Pigmented Spot Improvement>

The melanin production rate of each sample was measured for a single use and combined use, and the effect of the combined use was evaluated by the following criteria using the theoretical value.

The theoretical value was melanin production rate (%) by single use of component (A)×melanin production rate (%) by single use of component (B)/100.

OOO: theoretical value—measured value is not less than 30%.

OO: theoretical value—measured value is not less than 10% and less than 30%.

O: theoretical value—measured value is not less than −10% and less than 10%.

Δ: theoretical value—measured value is less than −10% but combined use is superior to single use of each of them x: theoretical value—measured value is less than −10% and combined use is inferior to single use thereof.

<Safety>

The cell viability rate of each sample was measured for a single use and combined use, and the effect of the combined use was evaluated by the following criteria using the degree of toxic mitigation.

The degree of toxic mitigation was cell viability rate (%) by combined use of component (A) and component (B)−cell viability rate (%) by single use of component (B).

◯◯◯: degree of toxic mitigation of not less than 9.

◯◯: degree of toxic mitigation of not less than 6 and less than 9.

◯: degree of toxic mitigation of not less than 3 and less than 6.

Δ: degree of toxic mitigation of not less than 0 and less than 3.

x: degree of toxic mitigation of less than 0.

these, kojic acid, arbutin, tranexamic acid, 4-methoxy salicylic acid or chamomilla recutita extract was combined as component (B), the whitening effect was extremely remarkably improved.

In addition, it was confirmed when (A) N-Ac-CP and arbutin, glutathione, chamomilla recutita extract or cetyl ascorbyl ether as component (B) were combined, melanin production suppressing effect was improved. Particularly, when glutathione or cetyl ascorbyl ether was combined as component (B), the whitening effect was remarkably improved and when, among these, glutathione was combined as component (B), the whitening effect was extremely remarkably improved.

From Table 1, it was further confirmed that the safety was improved by combining (A) N-Ac-CP2Et with kojic acid, arbutin, rcinol, glutathione, tranexamic acid, chamomilla recutita extract, ellagic acid or linoleic acid as component (B). Particularly, kojic acid, rcinol, glutathione, tranexamic acid,

TABLE 1

| | | sample name | concentration | | combined use effect on whitening | | | | | safety combined use effect | | | |
|---|---|---|---|---|---|---|---|---|---|---|---|---|---|
| | | | | | Melanin production rate (single) | Melanin production rate (combined use) | theoretical value by combined use | theoretical value − measured value | combined use effect | cell viability rate (single) | cell viability rate (combined use) | degree of toxic mitigation | combined use effect |
| Ex. 1 | (A) | N—Ac-CP2Et | 20 mM | 0.5226% | 62.0 | 8.4 | 40.9 | 32.5 | ◯◯◯ | 101.5 | 111.1 | 12.0 | ◯◯◯ |
| | (B) | kojic acid | 0.25 mM | 0.0036% | 66.0 | | | | | 99.1 | | | |
| Ex. 2 | (A) | N—Ac-CP2Et | 15 mM | 0.3920% | 92.2 | 39.2 | 78.8 | 39.6 | ◯◯◯ | 105.7 | 89.5 | 4.0 | ◯ |
| | (B) | arbutin | 0.5 mM | 0.0136% | 85.5 | | | | | 85.5 | | | |
| Ex. 3 | (A) | N—Ac-CP2Et | 20 mM | 0.5226% | 62.0 | 37.3 | 41.0 | 3.7 | ◯ | 101.5 | 100.7 | 6.4 | ◯◯ |
| | (B) | rcinol | 12.5 μM | 0.0002% | 66.2 | | | | | 94.3 | | | |
| Ex. 4 | (A) | N—Ac-CP2Et | 22.5 mM | 0.5879% | 48.6 | 46.0 | 48.6 | 2.6 | ◯ | 98.6 | 101.0 | 6.6 | ◯◯ |
| | (B) | GSH | 0.5 mM | 0.0306% | 100.0 | | | | | 94.4 | | | |
| Ex. 5 | (A) | N—Ac-CP2Et | 20 mM | 0.5226% | 62.0 | 31.6 | 62.0 | 30.4 | ◯◯◯ | 101.5 | 99.7 | 6.6 | ◯◯ |
| | (B) | tranexamic acid | 10 mM | 0.1572% | 100.0 | | | | | 93.1 | | | |
| Ex. 6 | (A) | N—Ac-CP2Et | 20 mM | 0.5226% | 62.0 | 7.5 | 62.0 | 54.5 | ◯◯◯ | 101.5 | 82.6 | −4.4 | X |
| | (B) | 4-MS | 5 mM | 0.0084% | 100.0 | | | | | 87.0 | | | |
| Ex. 7 | (A) | N—Ac-CP2Et | 22.5 mM | 0.5879% | 48.6 | 6.3 | 43.6 | 37.3 | ◯◯◯ | 98.6 | 66.0 | 10.8 | ◯◯◯ |
| | (B) | chamomilla recutita extract | 1% | 1.0000% | 89.8 | | | | | 55.2 | | | |
| Ex. 8 | (A) | N—Ac-CP2Et | 22.5 mM | 0.5879% | 48.6 | 21.5 | 35.4 | 13.9 | ◯◯ | 98.6 | 65.0 | −10.8 | X |
| | (B) | cetyl ascorbyl ether | 30 μM | 0.0012% | 72.8 | | | | | 75.8 | | | |
| Ex. 9 | (A) | N—Ac-CP2Et | 22.5 mM | 0.5879% | 48.6 | 45.6 | 48.6 | 3.0 | ◯ | 98.6 | 113.8 | 17.7 | ◯◯◯ |
| | (B) | ellagic acid | 6 μM | 0.0002% | 100.0 | | | | | 96.1 | | | |
| Ex. 10 | (A) | N—Ac-CP2Et | 20 mM | 0.5226% | 62.0 | 51.5 | 44.2 | −7.3 | ◯ | 101.5 | 113.0 | 7.8 | ◯◯ |
| | (B) | linoleic acid | 75 μM | 0.0021% | 71.3 | | | | | 105.2 | | | |
| Ex. 11 | (A) | N—Ac-CP | 25 mM | 0.5831% | 35.3 | 11.1 | 16.0 | 4.9 | ◯ | 97.8 | 104.0 | 7.5 | ◯◯ |
| | (B) | arbutin | 0.5 mM | 0.0136% | 45.2 | | | | | 96.5 | | | |
| Ex. 12 | (A) | N—Ac-CP | 22.5 mM | 0.5248% | 45.1 | 0.9 | 45.1 | 44.2 | ◯◯◯ | 100.6 | 99.0 | 31.2 | ◯◯◯ |
| | (B) | GSH | 2 mM | 0.0615% | 100.0 | | | | | 67.8 | | | |
| Ex. 13 | (A) | N—Ac-CP | 20 mM | 0.4665% | 59.4 | 56.2 | 59.4 | 3.2 | ◯ | 95.6 | 58.5 | 26.2 | ◯◯◯ |
| | (B) | chamomilla recutita extract | 2% | 2.0000% | 100.0 | | | | | 32.3 | | | |
| Ex. 14 | (A) | N—Ac-CP | 22.5 mM | 0.5248% | 45.1 | 19.9 | 30.5 | 10.6 | ◯◯ | 100.6 | 65.0 | −10.8 | X |
| | (B) | cetyl ascorbyl ether | 30 μM | 0.0012% | 67.6 | | | | | 75.8 | | | |

From Table 1, it was confirmed that a melanin production suppressive effect was improved by combining (A) N-Ac-CP2Et and kojic acid, arbutin, rcinol, glutathione, tranexamic acid, 4-methoxy salicylic acid, chamomilla recutita extract, cetyl ascorbyl ether, ellagic acid or linoleic acid as component (B). Particularly, when kojic acid, arbutin, tranexamic acid, 4-methoxy salicylic acid, chamomilla recutita extract, or cetyl ascorbyl ether was combined as component (B), the whitening effect was remarkably improved and when, among chamomilla recutita extract, ellagic acid and linoleic acid showed remarkably improved safety and, among these, kojic acid, chamomilla recutita extract and ellagic acid showed extremely remarkably improved safety.

In addition, it was confirmed when (A) N-Ac-CP is combined with arbutin, glutathione or chamomilla recutita extract as component (B), the safety was improved. Particularly, glutathione and chamomilla recutita extract showed remarkably improved safety.

Experimental Example 3

Melanin Production Rate Measurement

The cysteine derivatives of Synthetic Example 1 and Synthetic Example 3 were measured for a melanin production rate for comparison of a whitening effect. B16 melanoma was cultured in DMEM (Dulbecco's Modified Eagle Medium) (containing high glucose, serum 10%). After confluence, it was seeded in a 96 well plate. The next day, each well medium was exchanged with DMEM added with each evaluation sample adjusted to 5-25 mM, and the cells were cultured for 3 days. The absorbance at 450 nm was measured by a microplatereader. By setting the measurement value 3 days after addition of each sample at a given concentration as a relative percentage to the measurement value of the control (no sample addition) defined as 100%, the melanin production rate of each sample to the melanin amount in the control as 100% was calculated.

The calculated concentrations of the cysteine derivatives of Synthetic Example 1 and Synthetic Example 3 necessary for suppressing the melanin production rate by 50% are shown in Table 2.

The microplatereader used in this melanin production suppressing test was MULTISKAN FC manufactured by Thermo Fisher Scientific Inc.

TABLE 2

|  | concentration suppressing melanin production by 50% |
|---|---|
| Synthetic Example 1 | 18.9 mM |
| Synthetic Example 3 | 16.6 mM |

From the results of Table 2, it was found that the cysteine derivative of Synthetic Example 3 shows a stronger melanin production suppressing effect than the cysteine derivative of Synthetic Example 1.

Examples of the cosmetic agent of the present invention are shown below. All of them are cosmetic agents having a superior whitening effect and superior in safety.

TABLE 3 essence (in wt %, total amount 100)

| component | Form. Ex. 1 | Form. Ex. 2 | Form. Ex. 3 | Form. Ex. 4 | Form. Ex. 5 | Form. Ex. 6 | Form. Ex. 7 | Form. Ex. 8 | Form. Ex. 9 | Form. Ex. 10 | Form. Ex. 11 | Form. Ex. 12 |
|---|---|---|---|---|---|---|---|---|---|---|---|---|
| lysolecitine | 0.50 | 0.50 | 0.50 | 0.50 | 0.50 | 0.50 | 0.50 | 0.50 | 0.50 | 0.50 | 0.50 | 0.50 |
| sorbitan polyoxyethylene monooleate (2 E.O.) | 0.30 | 0.30 | 0.30 | 0.30 | 0.30 | 0.30 | 0.30 | 0.30 | 0.30 | 0.30 | 0.30 | 0.30 |
| polyoxyethylene hydrogenated castor oil (40 E.O.) | 0.50 | 0.50 | 0.50 | 0.50 | 0.50 | 0.50 | 0.50 | 0.50 | 0.50 | 0.50 | 0.50 | 0.50 |
| ethanol | 7.00 | 7.00 | 7.00 | 7.00 | 7.00 | 7.00 | 7.00 | 7.00 | 7.00 | 7.00 | 7.00 | 7.00 |
| methylphenylpolysiloxane | 3.00 | 3.00 | 3.00 | 3.00 | 3.00 | 3.00 | 3.00 | 3.00 | 3.00 | 3.00 | 3.00 | 3.00 |
| flavor | 0.01 | 0.01 | 0.01 | 0.01 | 0.01 | 0.01 | 0.01 | 0.01 | 0.01 | 0.01 | 0.01 | 0.01 |
| N-acetyl-2-methylthiazolidine-2,4-dicarboxylic acid 2-ethyl ester |  |  | 1.00 | 1.00 | 1.50 | 1.50 |  |  |  |  |  |  |
| N-acetyl-2-methylthiazolidine-2,4-dicarboxylic acid |  |  |  |  |  |  | 1.00 | 1.00 | 1.00 | 1.00 | 1.50 | 1.50 |
| sodium N-acetyl-2-methylthiazolidine-2,4-dicarboxylic acid 2-ethyl ester | 1.00 |  |  |  |  |  |  |  |  |  |  |  |
| disodium N-acetyl-2-methylthiazolidine-2,4-dicarboxylic acid |  | 1.00 |  |  |  |  |  |  |  |  |  |  |
| *chamomilla recutita* extract | 0.10 |  | 0.10 |  |  |  |  |  |  |  |  |  |
| rcinol |  | 0.50 |  | 0.50 |  |  |  |  |  |  |  |  |
| GSH |  |  |  |  | 0.50 |  |  |  |  |  |  |  |
| tranexamic acid |  |  |  |  |  | 0.50 |  |  |  |  |  |  |
| 4-methoxy salicylic acid |  |  |  |  |  |  | 1.00 |  |  |  |  |  |
| safflower seed extract |  |  |  |  |  |  |  | 1.00 |  |  |  |  |
| magnesium ascorbic acid phosphate |  |  |  |  |  |  |  |  | 0.10 |  |  |  |
| oligosaccharide |  |  |  |  |  |  |  |  |  | 2.00 |  |  |
| ellagic acid |  |  |  |  |  |  |  |  |  |  | 0.10 |  |
| hydroquinone |  |  |  |  |  |  |  |  |  |  |  | 0.50 |
| coumaroylserotonin | 0.01 |  |  |  |  |  | 0.01 |  |  |  |  |  |
| feruloylserotonin |  | 0.01 |  |  |  |  |  |  | 0.01 |  |  |  |
| serotonin derivative |  |  |  |  | 0.01 |  |  |  |  |  | 0.01 |  |
| trioleyl phosphate | 7.00 | 7.00 | 7.00 | 7.00 | 7.00 | 7.00 | 7.00 | 7.00 | 7.00 | 7.00 | 7.00 | 7.00 |
| 1,3-butyleneglycol | 3.00 | 3.00 | 3.00 | 3.00 | 3.00 | 3.00 | 3.00 | 3.00 | 3.00 | 3.00 | 3.00 | 3.00 |
| polyethylene glycol 1000 | 1.00 | 1.00 | 1.00 | 1.00 | 1.00 | 1.00 | 1.00 | 1.00 | 1.00 | 1.00 | 1.00 | 1.00 |
| ascorbic acid 2-glucoside | 2.00 | 2.00 | 2.00 | 2.00 | 2.00 | 2.00 | 2.00 | 2.00 | 2.00 | 2.00 | 2.00 | 2.00 |
| dipotassium glycyrrhizinate | 0.20 | 0.20 | 0.20 | 0.20 | 0.20 | 0.20 | 0.20 | 0.20 | 0.20 | 0.20 | 0.20 | 0.20 |
| nicotinic acid amide | 1.00 | 1.00 | 1.00 | 1.00 | 1.00 | 1.00 | 1.00 | 1.00 | 1.00 | 1.00 | 1.00 | 1.00 |
| N-methyl-L-serine | 0.10 | 0.10 | 0.10 | 0.10 | 0.10 | 0.10 | 0.10 | 0.10 | 0.10 | 0.10 | 0.10 | 0.10 |
| potassium hydroxide | 0.15 | 0.15 | 0.15 | 0.15 | 0.15 | 0.15 | 0.15 | 0.15 | 0.15 | 0.15 | 0.15 | 0.15 |
| lactic acid bacteria fermented solution | 0.10 | 0.10 | 0.10 | 0.10 | 0.10 | 0.10 | 0.10 | 0.10 | 0.10 | 0.10 | 0.10 | 0.10 |
| γ-aminobutyric acid | 0.02 | 0.02 | 0.02 | 0.02 | 0.02 | 0.02 | 0.02 | 0.02 | 0.02 | 0.02 | 0.02 | 0.02 |
| lavender extract | 0.01 | 0.01 | 0.01 | 0.01 | 0.01 | 0.01 | 0.01 | 0.01 | 0.01 | 0.01 | 0.01 | 0.01 |
| peppermint extract | 0.01 | 0.01 | 0.01 | 0.01 | 0.01 | 0.01 | 0.01 | 0.01 | 0.01 | 0.01 | 0.01 | 0.01 |
| *salvia officinalis* (sage) extract | 0.01 | 0.01 | 0.01 | 0.01 | 0.01 | 0.01 | 0.01 | 0.01 | 0.01 | 0.01 | 0.01 | 0.01 |

TABLE 3-continued essence (in wt %, total amount 100)

| component | Form. Ex. 1 | Form. Ex. 2 | Form. Ex. 3 | Form. Ex. 4 | Form. Ex. 5 | Form. Ex. 6 | Form. Ex. 7 | Form. Ex. 8 | Form. Ex. 9 | Form. Ex. 10 | Form. Ex. 11 | Form. Ex. 12 |
|---|---|---|---|---|---|---|---|---|---|---|---|---|
| anise extract | 0.01 | 0.01 | 0.01 | 0.01 | 0.01 | 0.01 | 0.01 | 0.01 | 0.01 | 0.01 | 0.01 | 0.01 |
| rose extract | 0.01 | 0.01 | 0.01 | 0.01 | 0.01 | 0.01 | 0.01 | 0.01 | 0.01 | 0.01 | 0.01 | 0.01 |
| *chamaecyparis obtusa* water | 0.01 | 0.01 | 0.01 | 0.01 | 0.01 | 0.01 | 0.01 | 0.01 | 0.01 | 0.01 | 0.01 | 0.01 |
| *aspalathus linearis* extract | 0.01 | 0.01 | 0.01 | 0.01 | 0.01 | 0.01 | 0.01 | 0.01 | 0.01 | 0.01 | 0.01 | 0.01 |
| extract *1 | 0.10 | 0.10 | 0.10 | 0.10 | 0.10 | 0.10 | 0.10 | 0.10 | 0.10 | 0.10 | 0.10 | 0.10 |
| 10% arginine aqueous solution | q.s. | q.s. | q.s. | q.s. | q.s. | q.s. | q.s. | q.s. | q.s. | q.s. | q.s. | q.s. |
| purified water | balance | balance | balance | balance | balance | balance | balance | balance | balance | balance | balance | balance |

TABLE 4 cream (in wt %, total amount 100)

| component | Form. Ex. 13 | Form. Ex. 14 | Form. Ex. 15 | Form. Ex. 16 | Form. Ex. 17 | Form. Ex. 18 | Form. Ex. 19 |
|---|---|---|---|---|---|---|---|
| squalane | 8.00 | 8.00 | 8.00 | 8.00 | 8.00 | 8.00 | 8.00 |
| cetyl ethylhexanoate | 3.00 | 3.00 | 3.00 | 3.00 | 3.00 | 3.00 | 3.00 |
| cetanol | 2.80 | 2.80 | 2.80 | 2.80 | 2.80 | 2.80 | 2.80 |
| stearic acid | 2.40 | 2.40 | 2.40 | 2.40 | 2.40 | 2.40 | 2.40 |
| stearic acid PG | 1.20 | 1.20 | 1.20 | 1.20 | 1.20 | 1.20 | 1.20 |
| glyceryl stearate (SE) | 3.30 | 3.30 | 3.30 | 3.30 | 3.30 | 3.30 | 3.30 |
| Polysorbate 60 | 0.50 | 0.50 | 0.50 | 0.50 | 0.50 | 0.50 | 0.50 |
| stearic acid PEG-40 | 1.50 | 1.50 | 1.50 | 1.50 | 1.50 | 1.50 | 1.50 |
| tocopherol | 0.05 | 0.05 | 0.05 | 0.05 | 0.05 | 0.05 | 0.05 |
| (phytosteryl/decyltetradecyl)- myristoyl methyl β alaninate | 1.00 | 1.00 | 1.00 | 1.00 | 1.00 | 1.00 | 1.00 |
| methylparaben | 0.20 | 0.20 | 0.20 | 0.20 | 0.20 | 0.20 | 0.20 |
| BG | 5.00 | 5.00 | 5.00 | 5.00 | 5.00 | 5.00 | 5.00 |
| xanthan gum | 0.10 | 0.10 | 0.10 | 0.10 | 0.10 | 0.10 | |
| gellan gum | | | | | | | 0.10 |
| N-acetyl-2-methylthiazolidine-2,4-dicarboxylic acid 2-ethyl ester | | | | | | | |
| N-acetyl-2-methylthiazolidine-2,4-dicarboxylic acid | 1.00 | 1.00 | | | 3.00 | 5.00 | 10.00 |
| kojic acid | 1.00 | | 1.00 | | | | |
| arbutin | | 1.00 | | 1.00 | | | |
| sodium N-acetyl-2-methylthiazolidine-2,4-dicarboxylic acid 2-ethyl ester | | | 1.00 | | | | |
| disodium N-acetyl-2-methylthiazolidine-2,4-dicarboxylic acid | | | | 3.00 | | | |
| GSH | | | | | 0.50 | | |
| tranexamic acid | | | | | | 0.50 | |
| 4-methoxy salicylic acid | | | | | | | 1.00 |
| safflower seed extract | | | | | | | |
| ascorbic acid 2-glucoside | | | | | | | |
| oligosaccharide | | | | | | | |
| ellagic acid | | | | | | | |
| hydroquinone | | | | | | | |
| linoleic acid | | | | | | | |
| cetyl ascorbyl ether | | | | | | | |
| arginine | 0.70 | 0.70 | 0.70 | 0.70 | 0.70 | 0.70 | 0.70 |
| extract *1 | 0.10 | 0.10 | 0.10 | 0.10 | 0.10 | 0.10 | 0.10 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

| component | Form. Ex. 20 | Form. Ex. 21 | Form. Ex. 22 | Form. Ex. 23 | Form. Ex. 24 | Form. Ex. 25 | Form. Ex. 26 |
|---|---|---|---|---|---|---|---|
| squalane | 8.00 | 8.00 | 8.00 | 8.00 | 8.00 | 8.00 | 8.00 |
| cetyl ethylhexanoate | 3.00 | 3.00 | 3.00 | 3.00 | 3.00 | 3.00 | 3.00 |
| cetanol | 2.80 | 2.80 | 2.80 | 2.80 | 2.80 | 2.80 | 2.80 |
| stearic acid | 2.40 | 2.40 | 2.40 | 2.40 | 2.40 | 2.40 | 2.40 |
| stearic acid PG | 1.20 | 1.20 | 1.20 | 1.20 | 1.20 | 1.20 | 1.20 |
| glyceryl stearate (SE) | 3.30 | 3.30 | 3.30 | 3.30 | 3.30 | 3.30 | 3.30 |
| Polysorbate 60 | 0.50 | 0.50 | 0.50 | 0.50 | 0.50 | 0.50 | 0.50 |
| stearic acid PEG-40 | 1.50 | 1.50 | 1.50 | 1.50 | 1.50 | 1.50 | 1.50 |
| tocopherol | 0.05 | 0.05 | 0.05 | 0.05 | 0.05 | 0.05 | 0.05 |
| (phytosteryl/decyltetradecyl)- myristoyl methyl β alaninate | 1.00 | 1.00 | 1.00 | 1.00 | 1.00 | 1.00 | 1.00 |

TABLE 4-continued cream (in wt %, total amount 100)

| component | | | | | | | |
|---|---|---|---|---|---|---|---|
| methylparaben | 0.20 | 0.20 | 0.20 | 0.20 | 0.20 | 0.20 | 0.20 |
| BG | 5.00 | 5.00 | 5.00 | 5.00 | 5.00 | 5.00 | 5.00 |
| xanthan gum | 0.10 | 0.10 | 0.10 | 0.10 | 0.10 | 0.10 | |
| gellan gum | | | | | | | 0.10 |
| N-acetyl-2-methylthiazolidine-2,4-dicarboxylic acid 2-ethyl ester | 1.00 | 1.00 | 1.00 | 3.00 | 3.00 | 5.00 | 10.00 |
| N-acetyl-2-methylthiazolidine-2,4-dicarboxylic acid | | | | | | | |
| kojic acid | | | | | | | |
| arbutin | | | | | | | |
| sodium N-acetyl-2-methylthiazolidine-2,4-dicarboxylic acid 2-ethyl ester | | | | | | | |
| disodium N-acetyl-2-methylthiazolidine-2,4-dicarboxylic acid | | | | | | | |
| GSH | | | | | | | |
| tranexamic acid | | | | | | | |
| 4-methoxy salicylic acid | | | | | | | |
| safflower seed extract | 1.00 | | | | | | |
| ascorbic acid 2-glucoside | | 0.10 | | | | | |
| oligosaccharide | | | 2.00 | | | | |
| ellagic acid | | | | 0.10 | | | |
| hydroquinone | | | | | 0.50 | | |
| linoleic acid | | | | | | 2.00 | |
| cetyl ascorbyl ether | | | | | | | 0.50 |
| arginine | 0.70 | 0.70 | 0.70 | 0.70 | 0.70 | 0.70 | 0.70 |
| extract *1 | 0.10 | 0.10 | 0.10 | 0.10 | 0.10 | 0.10 | 0.10 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

TABLE 5 cream (in wt %, total amount 100)

| component | Form. Ex. 27 | Form. Ex. 28 | Form. Ex. 29 | Form. Ex. 30 | Form. Ex. 31 | Form. Ex. 32 | Form. Ex. 33 |
|---|---|---|---|---|---|---|---|
| 2,2'-dihydroxy-5,5'-di-n-propylbiphenyl | 0.50 | 0.50 | 0.50 | 0.50 | 0.50 | 0.50 | 0.50 |
| macadamia nut oil fatty acid phytosteryl | 0.50 | 0.50 | 0.50 | 0.50 | 0.50 | 0.50 | 0.50 |
| long chain branched fatty acid cholesteryl | 2.00 | 2.00 | 2.00 | 2.00 | 2.00 | 2.00 | 2.00 |
| hydrogenated soybean phospholipid | 0.50 | 0.50 | 0.50 | 0.50 | 0.50 | 0.50 | 0.50 |
| DPG | 5.00 | 5.00 | 5.00 | 5.00 | 5.00 | 5.00 | 5.00 |
| behenyl alcohol | 2.00 | 2.00 | 2.00 | 2.00 | 2.00 | 2.00 | 2.00 |
| microcrystalline wax | 1.00 | 1.00 | 1.00 | 1.00 | 1.00 | 1.00 | 1.00 |
| glycerol | 5.00 | 5.00 | 5.00 | 5.00 | 5.00 | 5.00 | 5.00 |
| sebacic acid diisopropyl ester | 4.00 | 4.00 | 4.00 | 4.00 | 4.00 | 4.00 | 4.00 |
| palmitic acid | 0.10 | 0.10 | 0.10 | 0.10 | 0.10 | 0.10 | 0.10 |
| liquid paraffin | 8.00 | 8.00 | 8.00 | 8.00 | 8.00 | 8.00 | 8.00 |
| methyl phenyl polysiloxane | 2.00 | 2.00 | 2.00 | 2.00 | 2.00 | 2.00 | 2.00 |
| dimethylpolysiloxane (0.1 m2/s; 25° C.) | 1.00 | 1.00 | 1.00 | 1.00 | 1.00 | 1.00 | 1.00 |
| oleth-2 | 0.50 | 0.50 | 0.50 | 0.50 | 0.50 | 0.50 | 0.50 |
| N-acetyl-2-methylthiazolidine-2,4-dicarboxylic acid 2-ethyl ester | 1.00 | 1.00 | 1.00 | 3.00 | | | 10.00 |
| N-acetyl-2-methylthiazolidine-2,4-dicarboxylic acid | | | | | | | |
| kojic acid | 2.00 | | | | | | |
| arbutin | | 2.00 | | | 5.00 | | |
| chamomilla recutita extract | | | 0.20 | | | 2.00 | |
| rcinol | | | | 1.00 | | | |
| potassium N-acetyl-2-methylthiazolidine-2,4-dicarboxylic acid 2-ethyl ester | | | | | 1.00 | | |
| dipotassium N-acetyl-2-methylthiazolidine-2,4-dicarboxylic acid | | | | | | 1.00 | |
| 4-methoxy salicylic acid | | | | | | | 2.00 |
| safflower seed extract | | | | | | | |
| ascorbic acid 2-glucoside | | | | | | | |
| oligosaccharide | | | | | | | |
| ellagic acid | | | | | | | |
| hydroquinone | | | | | | | |
| linoleic acid | | | | | | | |
| cetyl ascorbyl ether | | | | | | | |
| coumaroylserotonin | 0.01 | 0.01 | | | | | |

TABLE 5-continued

| cream (in wt %, total amount 100) | | | | | | | |
|---|---|---|---|---|---|---|---|
| feruloylserotonin | | | 0.01 | 0.01 | | | |
| serotonin derivative | | | | | 0.01 | 0.01 | |
| birch extract | 0.10 | 0.10 | 0.10 | 0.10 | 0.10 | 0.10 | 0.10 |
| common sorrel extract | 0.10 | 0.10 | 0.10 | 0.10 | 0.10 | 0.10 | 0.10 |
| *sophora angustifolia* extract | 0.10 | 0.10 | 0.10 | 0.10 | 0.10 | 0.10 | 0.10 |
| peony root extract | 0.10 | 0.10 | 0.10 | 0.10 | 0.10 | 0.10 | 0.10 |
| *asiasarum* root extract | 0.10 | 0.10 | 0.10 | 0.10 | 0.10 | 0.10 | 0.10 |
| *pyracantha fortuneana* extract | 0.10 | 0.10 | 0.10 | 0.10 | 0.10 | 0.10 | 0.10 |
| *swertia herba* extract | 0.10 | 0.10 | 0.10 | 0.10 | 0.10 | 0.10 | 0.10 |
| extract *1 | 0.10 | 0.10 | 0.10 | 0.10 | 0.10 | 0.10 | 0.10 |
| Glycyrrhizic acid 2K | 0.10 | 0.10 | 0.10 | 0.10 | 0.10 | 0.10 | 0.10 |
| EDTA-2Na | 0.05 | 0.05 | 0.05 | 0.05 | 0.05 | 0.05 | 0.05 |
| phenoxyethanol | 0.40 | 0.40 | 0.40 | 0.40 | 0.40 | 0.40 | 0.40 |
| chlorphenesin | 0.10 | 0.10 | 0.10 | 0.10 | 0.10 | 0.10 | 0.10 |
| xanthan gum | 0.15 | 0.15 | 0.15 | 0.15 | 0.15 | 0.15 | 0.15 |
| flavor | 0.10 | 0.10 | 0.10 | 0.10 | 0.10 | 0.10 | 0.10 |
| sodium hydroxide | q.s. | q.s. | q.s. | q.s. | q.s. | q.s. | q.s. |
| purified water | balance | balance | balance | balance | balance | balance | balance |

| component | Form. Ex. 34 | Form. Ex. 35 | Form. Ex. 36 | Form. Ex. 37 | Form. Ex. 38 | Form. Ex. 39 | Form. Ex. 40 |
|---|---|---|---|---|---|---|---|
| 2,2'-dihydroxy-5,5'-di-n-propylbiphenyl | 0.50 | 0.50 | 0.50 | 0.50 | 0.50 | 0.50 | 0.50 |
| macadamia nut oil fatty acid phytosteryl | 0.50 | 0.50 | 0.50 | 0.50 | 0.50 | 0.50 | 0.50 |
| long chain branched fatty acid cholesteryl | 2.00 | 2.00 | 2.00 | 2.00 | 2.00 | 2.00 | 2.00 |
| hydrogenated soybean phospholipid | 0.50 | 0.50 | 0.50 | 0.50 | 0.50 | 0.50 | 0.50 |
| DPG | 5.00 | 5.00 | 5.00 | 5.00 | 5.00 | 5.00 | 5.00 |
| behenyl alcohol | 2.00 | 2.00 | 2.00 | 2.00 | 2.00 | 2.00 | 2.00 |
| microcrystalline wax | 1.00 | 1.00 | 1.00 | 1.00 | 1.00 | 1.00 | 1.00 |
| glycerol | 5.00 | 5.00 | 5.00 | 5.00 | 5.00 | 5.00 | 5.00 |
| sebacic acid diisopropyl ester | 4.00 | 4.00 | 4.00 | 4.00 | 4.00 | 4.00 | 4.00 |
| palmitic acid | 0.10 | 0.10 | 0.10 | 0.10 | 0.10 | 0.10 | 0.10 |
| liquid paraffin | 8.00 | 8.00 | 8.00 | 8.00 | 8.00 | 8.00 | 8.00 |
| methyl phenyl polysiloxane | 2.00 | 2.00 | 2.00 | 2.00 | 2.00 | 2.00 | 2.00 |
| dimethylpolysiloxane (0.1 m2/s; 25° C.) | 1.00 | 1.00 | 1.00 | 1.00 | 1.00 | 1.00 | 1.00 |
| oleth-2 | 0.50 | 0.50 | 0.50 | 0.50 | 0.50 | 0.50 | 0.50 |
| N-acetyl-2-methylthiazolidine-2,4-dicarboxylic acid 2-ethyl ester | | | | | | | |
| N-acetyl-2-methylthiazolidine-2,4-dicarboxylic acid | 1.00 | 1.00 | 1.00 | 3.00 | 3.00 | 5.00 | 10.00 |
| kojic acid | | | | | | | |
| arbutin | | | | | | | |
| *chamomilla recutita* extract | | | | | | | |
| rcinol | | | | | | | |
| potassium N-acetyl-2-methylthiazolidine-2,4-dicarboxylic acid 2-ethyl ester | | | | | | | |
| dipotassium N-acetyl-2-methylthiazolidine-2,4-dicarboxylic acid | | | | | | | |
| 4-methoxy salicylic acid | | | | | | | |
| safflower seed extract | 2.00 | | | | | | |
| ascorbic acid 2-glucoside | | 0.20 | | | | | |
| oligosaccharide | | | 4.00 | | | | |
| ellagic acid | | | | 0.20 | | | |
| hydroquinone | | | | | 1.00 | | |
| linoleic acid | | | | | | 2.00 | |
| cetyl ascorbyl ether | | | | | | | 1.00 |
| coumaroylserotonin | | 0.01 | 0.01 | | | | |
| feruloylserotonin | | | | 0.01 | 0.01 | | |
| serotonin derivative | | | | | | 0.01 | 0.01 |
| birch extract | 0.10 | 0.10 | 0.10 | 0.10 | 0.10 | 0.10 | 0.10 |
| common sorrel extract | 0.10 | 0.10 | 0.10 | 0.10 | 0.10 | 0.10 | 0.10 |
| *sophora angustifolia* extract | 0.10 | 0.10 | 0.10 | 0.10 | 0.10 | 0.10 | 0.10 |
| peony root extract | 0.10 | 0.10 | 0.10 | 0.10 | 0.10 | 0.10 | 0.10 |
| *asiasarum* root extract | 0.10 | 0.10 | 0.10 | 0.10 | 0.10 | 0.10 | 0.10 |
| *pyracantha fortuneana* extract | 0.10 | 0.10 | 0.10 | 0.10 | 0.10 | 0.10 | 0.10 |
| *swertia herba* extract | 0.10 | 0.10 | 0.10 | 0.10 | 0.10 | 0.10 | 0.10 |
| extract *1 | 0.10 | 0.10 | 0.10 | 0.10 | 0.10 | 0.10 | 0.10 |
| Glycyrrhizic acid 2K | 0.10 | 0.10 | 0.10 | 0.10 | 0.10 | 0.10 | 0.10 |
| EDTA-2Na | 0.05 | 0.05 | 0.05 | 0.05 | 0.05 | 0.05 | 0.05 |
| phenoxyethanol | 0.40 | 0.40 | 0.40 | 0.40 | 0.40 | 0.40 | 0.40 |
| chlorphenesin | 0.10 | 0.10 | 0.10 | 0.10 | 0.10 | 0.10 | 0.10 |
| xanthan gum | 0.15 | 0.15 | 0.15 | 0.15 | 0.15 | 0.15 | 0.15 |
| flavor | 0.10 | 0.10 | 0.10 | 0.10 | 0.10 | 0.10 | 0.10 |
| sodium hydroxide | q.s. | q.s. | q.s. | q.s. | q.s. | q.s. | q.s. |
| purified water | balance | balance | balance | balance | balance | balance | balance |

TABLE 6 milky lotion (in wt %, total amount 100)

| component | Form. Ex. 41 | Form. Ex. 42 | Form. Ex. 43 | Form. Ex. 44 | Form. Ex. 45 | Form. Ex. 46 | Form. Ex. 47 | Form. Ex. 48 | Form. Ex. 49 | Form. Ex. 50 | Form. Ex. 51 | Form. Ex. 52 |
|---|---|---|---|---|---|---|---|---|---|---|---|---|
| stearic acid | 2.00 | 2.00 | 2.00 | 2.00 | 2.00 | 2.00 | 2.00 | 2.00 | 2.00 | 2.00 | 2.00 | 2.00 |
| cetanol | 1.00 | 1.00 | 1.00 | 1.00 | 1.00 | 1.00 | 1.00 | 1.00 | 1.00 | 1.00 | 1.00 | 1.00 |
| petrolatum | 2.00 | 2.00 | 2.00 | 2.00 | 2.00 | 2.00 | 2.00 | 2.00 | 2.00 | 2.00 | 2.00 | 2.00 |
| liquid paraffin | 9.00 | 9.00 | 9.00 | 9.00 | 9.00 | 9.00 | 9.00 | 9.00 | 9.00 | 9.00 | 9.00 | 9.00 |
| cetyl ethylhexanoate | 1.00 | 1.00 | 1.00 | 1.00 | 1.00 | 1.00 | 1.00 | 1.00 | 1.00 | 1.00 | 1.00 | 1.00 |
| di(octyldodecyl/phytosteryl/behenyl)-lauroyl glutamate | 0.10 | 0.10 | 0.10 | 0.10 | 0.10 | 0.10 | 0.10 | 0.10 | 0.10 | 0.10 | 0.10 | 0.10 |
| di(cholesteryl/behenyl/octyldodecyl)-lauroyl glutamate | 0.10 | 0.10 | 0.10 | 0.10 | 0.10 | 0.10 | 0.10 | 0.10 | 0.10 | 0.10 | 0.10 | 0.10 |
| (phytosteryl/isostearyl/cetyl/stearyl/behenyl)dimer dilinoleate | 0.10 | 0.10 | | 0.10 | 0.10 | | 0.10 | 0.10 | | 0.10 | 0.10 | |
| bis(behenyl/isostearyl/phytosteryl)-dimer dilinoleyl dimer dilinoleate | | | 0.10 | | | 0.10 | | | 0.10 | | | 0.10 |
| jojoba oil | 1.00 | 1.00 | 1.00 | 1.00 | 1.00 | 1.00 | 1.00 | 1.00 | 1.00 | 1.00 | 1.00 | 1.00 |
| squalane | 2.00 | 2.00 | 2.00 | 2.00 | 2.00 | 2.00 | 2.00 | 2.00 | 2.00 | 2.00 | 2.00 | 2.00 |
| POE (30) hydrogenated castor oil | 3.00 | 3.00 | 3.00 | 3.00 | 3.00 | 3.00 | 3.00 | 3.00 | 3.00 | 3.00 | 3.00 | 3.00 |
| methyl phenyl polysiloxane | 1.00 | 1.00 | 1.00 | 1.00 | 1.00 | 1.00 | 1.00 | 1.00 | 1.00 | 1.00 | 1.00 | 1.00 |
| tocopherol | 0.30 | 0.30 | 0.30 | 0.30 | 0.30 | 0.30 | 0.30 | 0.30 | 0.30 | 0.30 | 0.30 | 0.30 |
| POE (10) monooleate | 0.10 | 0.10 | 0.10 | 0.10 | 0.10 | 0.10 | 0.10 | 0.10 | 0.10 | 0.10 | 0.10 | 0.10 |
| butylparaben | 0.20 | 0.20 | 0.20 | 0.20 | 0.20 | 0.20 | 0.20 | 0.20 | 0.20 | 0.20 | 0.20 | 0.20 |
| PG | 5.00 | 5.00 | 5.00 | 5.00 | 5.00 | 5.00 | 5.00 | 5.00 | 5.00 | 5.00 | 5.00 | 5.00 |
| BG | 2.00 | 2.00 | 2.00 | 2.00 | 2.00 | 2.00 | 2.00 | 2.00 | 2.00 | 2.00 | 2.00 | 2.00 |
| carboxyvinyl polymer | 0.50 | 0.50 | 0.50 | 0.50 | 0.50 | 0.50 | 0.50 | 0.50 | 0.50 | 0.50 | 0.50 | 0.50 |
| N-acetyl-2-methylthiazolidine-2,4-dicarboxylic acid 2-ethyl ester | 1.00 | 1.00 | 1.00 | 2.00 | 2.00 | 2.00 | | | | | | |
| N-acetyl-2-methylthiazolidine-2,4-dicarboxylic acid | | | | | | | | | | 1.00 | 2.00 | 2.00 | 2.00 |
| glycyrrhizic acid 2K | 0.10 | 0.10 | 0.10 | 0.10 | 0.10 | 0.10 | 0.10 | 0.10 | 0.10 | 0.10 | 0.10 | 0.10 |
| kojic acid | 1.00 | | | | | | | | | | | |
| arbutin | | 1.00 | | | | | | | | | | |
| chamomilla recutita extract | | | 0.10 | | | | | | | | | |
| rcinol | | | | 0.50 | | | | | | | | |
| GSH | | | | | 0.50 | | 0.50 | | | | | |
| tranexamic acid | | | | | | 0.50 | | 0.50 | | | | |
| potassium N-acetyl-2-methylthiazolidine-2,4-dicarboxylic acid 2-ethyl ester | | | | | | | | 1.00 | | | | |
| dipotassium N-acetyl-2-methylthiazolidine-2,4-dicarboxylic acid | | | | | | | | | 1.00 | | | |
| magnesium ascorbic acid phosphate | | | | | | | | | | 0.10 | | |
| oligosaccharide | | | | | | | | | | | 2.00 | |
| ellagic acid | | | | | | | | | | | | 0.10 |
| hydroquinone | | | | | | | | | | | | 0.50 |
| leucine | 0.01 | 0.01 | 0.01 | 0.01 | 0.01 | 0.01 | 0.01 | 0.01 | 0.01 | 0.01 | 0.01 | 0.01 |
| isoleucine | 0.01 | 0.01 | 0.01 | 0.01 | 0.01 | 0.01 | 0.01 | 0.01 | 0.01 | 0.01 | 0.01 | 0.01 |
| valine | 0.01 | 0.01 | 0.01 | 0.01 | 0.01 | 0.01 | 0.01 | 0.01 | 0.01 | 0.01 | 0.01 | 0.01 |
| phenylalanine | 0.01 | 0.01 | 0.01 | 0.01 | 0.01 | 0.01 | 0.01 | 0.01 | 0.01 | 0.01 | 0.01 | 0.01 |
| tryptophan | 0.01 | 0.01 | 0.01 | 0.01 | 0.01 | 0.01 | 0.01 | 0.01 | 0.01 | 0.01 | 0.01 | 0.01 |
| aspartic acid | 0.01 | 0.01 | 0.01 | 0.01 | 0.01 | 0.01 | 0.01 | 0.01 | 0.01 | 0.01 | 0.01 | 0.01 |
| sodium glutamate | 0.01 | 0.01 | 0.01 | 0.01 | 0.01 | 0.01 | 0.01 | 0.01 | 0.01 | 0.01 | 0.01 | 0.01 |
| lysine hydrochloride | 0.01 | 0.01 | 0.01 | 0.01 | 0.01 | 0.01 | 0.01 | 0.01 | 0.01 | 0.01 | 0.01 | 0.01 |
| arginine | 0.01 | 0.01 | 0.01 | 0.01 | 0.01 | 0.01 | 0.01 | 0.01 | 0.01 | 0.01 | 0.01 | 0.01 |
| threonine | 0.01 | 0.01 | 0.01 | 0.01 | 0.01 | 0.01 | 0.01 | 0.01 | 0.01 | 0.01 | 0.01 | 0.01 |
| alanine | 0.01 | 0.01 | 0.01 | 0.01 | 0.01 | 0.01 | 0.01 | 0.01 | 0.01 | 0.01 | 0.01 | 0.01 |
| proline | 0.01 | 0.01 | 0.01 | 0.01 | 0.01 | 0.01 | 0.01 | 0.01 | 0.01 | 0.01 | 0.01 | 0.01 |
| serine | 0.01 | 0.01 | 0.01 | 0.01 | 0.01 | 0.01 | 0.01 | 0.01 | 0.01 | 0.01 | 0.01 | 0.01 |
| glycine | 0.01 | 0.01 | 0.01 | 0.01 | 0.01 | 0.01 | 0.01 | 0.01 | 0.01 | 0.01 | 0.01 | 0.01 |
| acetylglutamine | 0.01 | 0.01 | 0.01 | 0.01 | 0.01 | 0.01 | 0.01 | 0.01 | 0.01 | 0.01 | 0.01 | 0.01 |
| histidine | 0.01 | 0.01 | 0.01 | 0.01 | 0.01 | 0.01 | 0.01 | 0.01 | 0.01 | 0.01 | 0.01 | 0.01 |
| pyridoxylserine | 0.01 | 0.01 | 0.01 | 0.01 | 0.01 | 0.01 | 0.01 | 0.01 | 0.01 | 0.01 | 0.01 | 0.01 |
| carnosine | 0.01 | 0.01 | 0.01 | 0.01 | 0.01 | 0.01 | 0.01 | 0.01 | 0.01 | 0.01 | 0.01 | 0.01 |
| acetylmethionine | 0.01 | 0.01 | 0.01 | 0.01 | 0.01 | 0.01 | 0.01 | 0.01 | 0.01 | 0.01 | 0.01 | 0.01 |
| acetylcysteine | 0.01 | 0.01 | 0.01 | 0.01 | 0.01 | 0.01 | 0.01 | 0.01 | 0.01 | 0.01 | 0.01 | 0.01 |
| extract *1 | 0.10 | 0.10 | 0.10 | 0.10 | 0.10 | 0.10 | 0.10 | 0.10 | 0.10 | 0.10 | 0.10 | 0.10 |
| zinc pyrrolidone carboxylate | 0.01 | 0.01 | 0.01 | 0.01 | 0.01 | 0.01 | 0.01 | 0.01 | 0.01 | 0.01 | 0.01 | 0.01 |
| sodium pyrrolidone carboxylate | 0.00 | 0.00 | 0.00 | 0.00 | 0.00 | 0.00 | 0.00 | 0.00 | 0.00 | 0.00 | 0.00 | 0.00 |
| pyrrolidonecarboxylic acid salt of cocoyl arginine ethyl | 0.01 | 0.01 | 0.01 | 0.01 | 0.01 | 0.01 | 0.01 | 0.01 | 0.01 | 0.01 | 0.01 | 0.01 |
| EDTA-2Na | 0.05 | 0.05 | 0.05 | 0.05 | 0.05 | 0.05 | 0.05 | 0.05 | 0.05 | 0.05 | 0.05 | 0.05 |
| magnesium ascorbyl phosphate | 0.10 | 0.10 | 0.10 | 0.10 | 0.10 | 0.10 | 0.10 | 0.10 | 0.10 | 0.10 | 0.10 | 0.10 |
| etidronic acid | 0.05 | 0.05 | 0.05 | 0.05 | 0.05 | 0.05 | 0.05 | 0.05 | 0.05 | 0.05 | 0.05 | 0.05 |

TABLE 6-continued milky lotion (in wt %, total amount 100)

| component | Form. Ex. 41 | Form. Ex. 42 | Form. Ex. 43 | Form. Ex. 44 | Form. Ex. 45 | Form. Ex. 46 | Form. Ex. 47 | Form. Ex. 48 | Form. Ex. 49 | Form. Ex. 50 | Form. Ex. 51 | Form. Ex. 52 |
|---|---|---|---|---|---|---|---|---|---|---|---|---|
| 10% arginine aqueous solution | q.s. | q.s. | q.s. | q.s. | q.s. | q.s. | q.s. | q.s. | q.s. | q.s. | q.s. | q.s. |
| flavor | q.s. | q.s. | q.s. | q.s. | q.s. | q.s. | q.s. | q.s. | q.s. | q.s. | q.s. | q.s. |
| purified water | balance | balance | balance | balance | balance | balance | balance | balance | balance | balance | balance | balance |

TABLE 7 milky lotion (in wt %, total amount 100)

| component | Form. Ex. 53 | Form. Ex. 54 | Form. Ex. 55 | Form. Ex. 56 | Form. Ex. 57 | Form. Ex. 58 | Form. Ex. 59 |
|---|---|---|---|---|---|---|---|
| liquid paraffin | 5.00 | 5.00 | 5.00 | 5.00 | 5.00 | 5.00 | 5.00 |
| dioctyldodecyl lauroylglutamate | 2.00 | 2.00 | 2.00 | 2.00 | 2.00 | 2.00 | 2.00 |
| dimer dilinoleyl hydrogenated rosinate | 0.50 | 0.50 | 0.50 | 0.50 | 0.50 | 0.50 | 0.50 |
| dimer dilinoleyl diisostearate | 0.50 | 0.50 | 0.50 | 0.50 | 0.50 | 0.50 | 0.50 |
| stearic acid PG | 0.50 | 0.50 | 0.50 | 0.50 | 0.50 | 0.50 | 0.50 |
| PEG-5 hydrogenated castor oil | 1.50 | 1.50 | 1.50 | 1.50 | 1.50 | 1.50 | 1.50 |
| PEG-5 glyceryl Stearate | 2.50 | 2.50 | 2.50 | 2.50 | 2.50 | 2.50 | 2.50 |
| butylparaben | 0.10 | 0.10 | 0.10 | 0.10 | 0.10 | 0.10 | 0.10 |
| lauroyllysine | 3.00 | 3.00 | 3.00 | 3.00 | 3.00 | 3.00 | 3.00 |
| carbomer | 0.20 | 0.20 | 0.20 | 0.20 | 0.20 | 0.20 | 0.20 |
| N-stearoyl-sodium glutamate | 0.30 | 0.30 | 0.30 | 0.30 | 0.30 | 0.30 | 0.30 |
| BG | 5.00 | 5.00 | 5.00 | 5.00 | 5.00 | 5.00 | 5.00 |
| methylparaben | 0.10 | 0.10 | 0.10 | 0.10 | 0.10 | 0.10 | 0.10 |
| N-acetyl-2-methylthiazolidine-2,4-dicarboxylic acid 2-ethyl ester | | | | | | | |
| N-acetyl-2-methylthiazolidine-2,4-dicarboxylic add | 2.00 | 2.00 | 1.50 | 1.50 | 1.00 | 1.00 | 1.00 |
| kojic acid | 1.00 | | | | | | |
| arbutin | | 1.00 | | | | | |
| chamomilla recutita extract | | | 0.10 | | | | |
| rcinol | | | | 0.50 | | | |
| GSH | | | | | 0.50 | | |
| tranexamic acid | | | | | | 0.50 | |
| 4-methoxy salicylic acid | | | | | | | 1.00 |
| safflower seed extract | | | | | | | |
| arginine N-acetyl-2-methylthiazolidine-2,4-dicarboxylic acid 2-ethyl ester | | | | | | | |
| diarginine N-acetyl-2-methylthiazolidine-2,4-dicarboxylic acid | | | | | | | |
| ellagic acid | | | | | | | |
| hydroquinone | | | | | | | |
| linoleic acid | | | | | | | |
| cetyl ascorbyl ether | | | | | | | |
| extract *1 | 0.10 | 0.10 | 0.10 | 0.10 | 0.10 | 0.10 | 0.10 |
| arginine | 0.24 | 0.24 | 0.24 | 0.24 | 0.24 | 0.24 | 0.24 |
| EDTA-2Na | 0.05 | 0.05 | 0.05 | 0.05 | 0.05 | 0.05 | 0.05 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

| component | Form. Ex. 60 | Form. Ex. 61 | Form. Ex. 62 | Form. Ex. 63 | Form. Ex. 64 | Form. Ex. 65 | Form. Ex. 66 |
|---|---|---|---|---|---|---|---|
| liquid paraffin | 5.00 | 5.00 | 5.00 | 5.00 | 5.00 | 5.00 | 5.00 |
| dioctyldodecyl lauroylglutamate | 2.00 | 2.00 | 2.00 | 2.00 | 2.00 | 2.00 | 2.00 |
| dimer dilinoleyl hydrogenated rosinate | 0.50 | 0.50 | 0.50 | 0.50 | 0.50 | 0.50 | 0.50 |
| dimer dilinoleyl diisostearate | 0.50 | 0.50 | 0.50 | 0.50 | 0.50 | 0.50 | 0.50 |
| stearic acid PG | 0.50 | 0.50 | 0.50 | 0.50 | 0.50 | 0.50 | 0.50 |
| PEG-5 hydrogenated castor oil | 1.50 | 1.50 | 1.50 | 1.50 | 1.50 | 1.50 | 1.50 |
| PEG-5 glyceryl Stearate | 2.50 | 2.50 | 2.50 | 2.50 | 2.50 | 2.50 | 2.50 |
| butylparaben | 0.10 | 0.10 | 0.10 | 0.10 | 0.10 | 0.10 | 0.10 |
| lauroyllysine | 3.00 | 3.00 | 3.00 | 3.00 | 3.00 | 3.00 | 3.00 |
| carbomer | 0.20 | 0.20 | 0.20 | 0.20 | 0.20 | 0.20 | 0.20 |
| N-stearoyl-sodium glutamate | 0.30 | 0.30 | 0.30 | 0.30 | 0.30 | 0.30 | 0.30 |
| BG | 5.00 | 5.00 | 5.00 | 5.00 | 5.00 | 5.00 | 5.00 |
| methylparaben | 0.10 | 0.10 | 0.10 | 0.10 | 0.10 | 0.10 | 0.10 |

TABLE 7-continued

| milky lotion (in wt %, total amount 100) | | | | | | | |
|---|---|---|---|---|---|---|---|
| N-acetyl-2-methylthiazolidine-2,4-dicarboxylic acid 2-ethyl ester | 2.00 | | | 1.50 | 1.00 | 1.00 | 1.00 |
| N-acetyl-2-methylthiazolidine-2,4-dicarboxylic add | | | | | | | |
| kojic acid | | | | | | | |
| arbutin | | | | | | | |
| *chamomilla recutita* extract | | | | | | | |
| rcinol | | | | | | | |
| GSH | | | | | | | |
| tranexamic acid | | | | | | | |
| 4-methoxy salicylic acid | | 1.00 | | | | | |
| safflower seed extract | 1.00 | | 1.00 | | | | |
| arginine N-acetyl-2-methylthiazolidine-2,4-dicarboxylic acid 2-ethyl ester | | 2.00 | | | | | |
| diarginine N-acetyl-2-methylthiazolidine-2,4-dicarboxylic acid | | | 1.50 | | | | |
| ellagic acid | | | | 0.10 | | | |
| hydroquinone | | | | | 0.50 | | |
| linoleic acid | | | | | | 2.00 | |
| cetyl ascorbyl ether | | | | | | | 0.50 |
| extract *1 | 0.10 | 0.10 | 0.10 | 0.10 | 0.10 | 0.10 | 0.10 |
| arginine | 0.24 | 0.24 | 0.24 | 0.24 | 0.24 | 0.24 | 0.24 |
| EDTA-2Na | 0.05 | 0.05 | 0.05 | 0.05 | 0.05 | 0.05 | 0.05 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

TABLE 8

| milky lotion (in wt %, total amount 100) | | | | | | | |
|---|---|---|---|---|---|---|---|
| component | Form. Ex. 67 | Form. Ex. 68 | Form. Ex. 69 | Form. Ex. 70 | Form. Ex. 71 | Form. Ex. 72 | Form. Ex. 73 |
| 2-ethylhexyl paradimethylaminobenzoate | 0.10 | 0.10 | 0.10 | 0.10 | 0.10 | 0.10 | 0.10 |
| mono-2-ethylhexyl diparamethoxy cinnamate | 0.20 | 0.20 | 0.20 | 0.20 | 0.20 | | |
| 4-methoxydibenzoylmethane | | | | | | 0.20 | 0.20 |
| stearic acid | 1.50 | 1.50 | 1.50 | 1.50 | 1.50 | 1.50 | 1.50 |
| cetanol | 0.50 | 0.50 | 0.50 | 0.50 | 0.50 | 0.50 | 0.50 |
| beeswax | 2.00 | 2.00 | 2.00 | 2.00 | 2.00 | 2.00 | 2.00 |
| polyoxyethylene (10) monooleic acid ester | 2.00 | 2.00 | 2.00 | 2.00 | 2.00 | 2.00 | 2.00 |
| arginine | 0.30 | 0.30 | 0.30 | 0.30 | 0.30 | 0.30 | 0.30 |
| dried seawater substance | 0.02 | 0.02 | 0.02 | 0.02 | 0.02 | 0.02 | 0.02 |
| sodium pyrrolidone carboxylate | 0.05 | 0.05 | 0.05 | 0.05 | 0.05 | 0.05 | 0.05 |
| N-acetyl-2-methylthiazolidine-2,4-dicarboxylic acid 2-ethyl ester | 0.10 | 0.10 | 0.50 | 0.50 | 2.00 | 2.00 | 5.00 |
| N-acetyl-2-methylthiazolidine-2,4-dicarboxylic acid | | | | | | | |
| kojic acid | 1.00 | | | | | | |
| arbutin | | 1.00 | | | | | |
| *chamomilla recutita* extract | | | 0.10 | | | | |
| rcinol | | | | 0.50 | | | |
| GSH | | | | | 0.50 | | |
| tranexamic acid | | | | | | 0.50 | |
| 4-methoxy salicylic acid | | | | | | | 1.00 |
| safflower seed extract | | | | | | | |
| ascorbic acid 2-glucoside | | | | | | | |
| oligosaccharide | | | | | | | |
| arginine N-acetyl-2-methylthiazolidine-2,4-dicarboxylic acid 2-ethyl ester | | | | | | | |
| diarginine N-acetyl-2-methylthiazolidine-2,4-dicarboxylic acid | | | | | | | |
| linoleic acid | | | | | | | |
| cetyl ascorbyl ether | | | | | | | |
| extract *1 | 0.10 | 0.10 | 0.10 | 0.10 | 0.10 | 0.10 | 0.10 |
| glycerol | 3.00 | 3.00 | 3.00 | 3.00 | 3.00 | 3.00 | 3.00 |
| ethanol | 3.00 | 3.00 | 3.00 | 3.00 | 3.00 | 3.00 | 3.00 |
| ethylparaben | 0.30 | 0.30 | 0.30 | 0.30 | 0.30 | 0.30 | 0.30 |

TABLE 8-continued

| milky lotion (in wt %, total amount 100) | | | | | | | |
|---|---|---|---|---|---|---|---|
| flavor | 0.03 | 0.03 | 0.03 | 0.03 | 0.03 | 0.03 | 0.03 |
| carboxyvinyl polymer | 0.12 | 0.12 | 0.12 | 0.12 | 0.12 | 0.12 | 0.12 |
| sodium hydroxide | q.s. | q.s. | q.s. | q.s. | q.s. | q.s. | q.s. |
| purified water | balance | balance | balance | balance | balance | balance | balance |

| component | Form. Ex. 74 | Form. Ex. 75 | Form. Ex. 76 | Form. Ex. 77 | Form. Ex. 78 | Form. Ex. 79 | Form. Ex. 80 |
|---|---|---|---|---|---|---|---|
| 2-ethylhexyl paradimethylaminobenzoate | 0.10 | 0.10 | 0.10 | 0.10 | 0.10 | 0.10 | 0.10 |
| mono-2-ethylhexyl diparamethoxy cinnamate | 0.20 | 0.20 | 0.20 | 0.20 | 0.20 | | |
| 4-methoxydibenzoylmethane | | | | | | 0.20 | 0.20 |
| stearic acid | 1.50 | 1.50 | 1.50 | 1.50 | 1.50 | 1.50 | 1.50 |
| cetanol | 0.50 | 0.50 | 0.50 | 0.50 | 0.50 | 0.50 | 0.50 |
| beeswax | 2.00 | 2.00 | 2.00 | 2.00 | 2.00 | 2.00 | 2.00 |
| polyoxyethylene (10) monooleic acid ester | 2.00 | 2.00 | 2.00 | 2.00 | 2.00 | 2.00 | 2.00 |
| arginine | 0.30 | 0.30 | 0.30 | 0.30 | 0.30 | 0.30 | 0.30 |
| dried seawater substance | 0.02 | 0.02 | 0.02 | 0.02 | 0.02 | 0.02 | 0.02 |
| sodium pyrrolidone carboxylate | 0.05 | 0.05 | 0.05 | 0.05 | 0.05 | 0.05 | 0.05 |
| N-acetyl-2-methylthiazolidine-2,4-dicarboxylic acid 2-ethyl ester | | | | | | | |
| N-acetyl-2-methylthiazolidine-2,4-dicarboxylic acid | 0.10 | 0.10 | 0.50 | | | 2.00 | 5.00 |
| kojic acid | | | | | | | |
| arbutin | | | | | | | |
| chamomilla recutita extract | | | | | | | |
| rcinol | | | | | | | |
| GSH | | | | | | | |
| tranexamic acid | | | | | | | |
| 4-methoxy salicylic acid | | | | | | | |
| safflower seed extract | 1.00 | | | | | | |
| ascorbic acid 2-glucoside | | 0.10 | | 0.10 | | | |
| oligosaccharide | | | 2.00 | | 2.00 | | |
| arginine N-acetyl-2-methylthiazolidine-2,4-dicarboxylic acid 2-ethyl ester | | | | 0.50 | | | |
| diarginine N-acetyl-2-methylthiazolidine-2,4-dicarboxylic acid | | | | | 2.00 | | |
| linoleic acid | | | | | | 2.00 | |
| cetyl ascorbyl ether | | | | | | | 0.50 |
| extract *1 | 0.10 | 0.10 | 0.10 | 0.10 | 0.10 | 0.10 | 0.10 |
| glycerol | 3.00 | 3.00 | 3.00 | 3.00 | 3.00 | 3.00 | 3.00 |
| ethanol | 3.00 | 3.00 | 3.00 | 3.00 | 3.00 | 3.00 | 3.00 |
| ethylparaben | 0.30 | 0.30 | 0.30 | 0.30 | 0.30 | 0.30 | 0.30 |
| flavor | 0.03 | 0.03 | 0.03 | 0.03 | 0.03 | 0.03 | 0.03 |
| carboxyvinyl polymer | 0.12 | 0.12 | 0.12 | 0.12 | 0.12 | 0.12 | 0.12 |
| sodium hydroxide | q.s. | q.s. | q.s. | q.s. | q.s. | q.s. | q.s. |
| purified water | balance | balance | balance | balance | balance | balance | balance |

TABLE 9

| sunscreen cosmetic (in wt %, total amount 100) | | | | | | | |
|---|---|---|---|---|---|---|---|
| component | Form. Ex. 81 | Form. Ex. 82 | Form. Ex. 83 | Form. Ex. 84 | Form. Ex. 85 | Form. Ex. 86 | Form. Ex. 87 |
| dimethylpolysiloxane | 5.00 | 5.00 | 5.00 | 5.00 | 5.00 | 5.00 | 5.00 |
| decamethylcyclopentasiloxane | 25.00 | 25.00 | 25.00 | 25.00 | 25.00 | 25.00 | 25.00 |
| trimethylsiloxysilicate | 5.00 | 5.00 | 5.00 | 5.00 | 5.00 | 5.00 | 5.00 |
| polyoxyethylene/methyl-polysiloxane copolymer | 2.00 | 2.00 | 2.00 | 2.00 | 2.00 | 2.00 | 2.00 |
| 2-ethylhexyl paramethoxycinnamate | 7.50 | 7.50 | 7.50 | 7.50 | 7.50 | 7.50 | 7.50 |
| spherical alkyl polyacrylate powder | 5.00 | 5.00 | 5.00 | 5.00 | 5.00 | 5.00 | 5.00 |
| zinc oxide fine particles coated dextrin palmitate (60 nm) | 5.00 | 5.00 | 5.00 | 5.00 | 5.00 | 5.00 | 5.00 |
| DPG | 5.00 | 5.00 | 5.00 | 5.00 | 5.00 | 5.00 | 5.00 |
| dimethyl distearylammonium hectorite | 0.50 | 0.50 | 0.50 | 0.50 | 0.50 | 0.50 | 0.50 |

TABLE 9-continued

| sunscreen cosmetic (in wt %, total amount 100) | | | | | | | |
|---|---|---|---|---|---|---|---|
| glycyrrhizic acid 2K | 0.02 | 0.02 | 0.02 | 0.02 | 0.02 | 0.02 | 0.02 |
| thiotaurine | 0.05 | 0.05 | 0.05 | 0.05 | 0.05 | 0.05 | 0.05 |
| N-acetyl-2-methylthiazolidine-2,4-dicarboxylic acid 2-ethyl ester | | | | | | | |
| N-acetyl-2-methylthiazolidine-2,4-dicarboxylic acid | 1.00 | 1.00 | 0.50 | 0.50 | 0.50 | 0.50 | 0.20 |
| kojic add | 0.50 | | | | | | |
| arbutin | | 0.50 | | | | | |
| chamomilla recutita extract | | | 0.10 | | | | |
| rcinol | | | | 0.20 | | | |
| GSH | | | | | 0.50 | | |
| tranexamic acid | | | | | | 1.00 | |
| 4-methoxy salicylic acid | | | | | | | 1.00 |
| safflower seed extract | | | | | | | |
| ascorbic acid 2-glucoside | | | | | | | |
| oligosaccharide | | | | | | | |
| ellagic acid | | | | | | | |
| hydroquinone | | | | | | | |
| ammonium N-acetyl-2-methylthiazolidine-2,4-dicarboxylic acid 2-ethyl ester | | | | | | | |
| diammonium N-acetyl-2-methylthiazolidine-2,4-dicarboxylic acid | | | | | | | |
| extract *1 | 0.10 | 0.10 | 0.10 | 0.10 | 0.10 | 0.10 | 0.10 |
| methylparaben | q.s. | q.s. | q.s. | q.s. | q.s. | q.s. | q.s. |
| phenoxyethanol | q.s. | q.s. | q.s. | q.s. | q.s. | q.s. | q.s. |
| trisodium edetate | q.s. | q.s. | q.s. | q.s. | q.s. | q.s. | q.s. |
| butylethylpropanediol | 0.50 | 0.50 | 0.50 | 0.50 | 0.50 | 0.50 | 0.50 |
| 10% arginine aqueous solution | q.s. | q.s. | q.s. | q.s. | q.s. | q.s. | q.s. |
| purified water | balance | balance | balance | balance | balance | balance | balance |
| flavor | q.s. | q.s. | q.s. | q.s. | q.s. | q.s. | q.s. |

| component | Form. Ex. 88 | Form. Ex. 89 | Form. Ex. 90 | Form. Ex. 91 | Form. Ex. 92 | Form. Ex. 93 | Form. Ex. 94 |
|---|---|---|---|---|---|---|---|
| dimethylpolysiloxane | 5.00 | 5.00 | 5.00 | 5.00 | 5.00 | 5.00 | 5.00 |
| decamethylcyclopentasiloxane | 25.00 | 25.00 | 25.00 | 25.00 | 25.00 | 25.00 | 25.00 |
| trimethylsiloxysilicate | 5.00 | 5.00 | 5.00 | 5.00 | 5.00 | 5.00 | 5.00 |
| polyoxyethylene/methyl-polysiloxane copolymer | 2.00 | 2.00 | 2.00 | 2.00 | 2.00 | 2.00 | 2.00 |
| 2-ethylhexyl paramethoxycinnamate | 7.50 | 7.50 | 7.50 | 7.50 | 7.50 | 7.50 | 7.50 |
| spherical alkyl polyacrylate powder | 5.00 | 5.00 | 5.00 | 5.00 | 5.00 | 5.00 | 5.00 |
| zinc oxide fine particles coated dextrin palmitate (60 nm) | 5.00 | 5.00 | 5.00 | 5.00 | 5.00 | 5.00 | 5.00 |
| DPG | 5.00 | 5.00 | 5.00 | 5.00 | 5.00 | 5.00 | 5.00 |
| dimethyl distearylammonium hectorite | 0.50 | 0.50 | 0.50 | 0.50 | 0.50 | 0.50 | 0.50 |
| glycyrrhizic acid 2K | 0.02 | 0.02 | 0.02 | 0.02 | 0.02 | 0.02 | 0.02 |
| thiotaurine | 0.05 | 0.05 | 0.05 | 0.05 | 0.05 | 0.05 | 0.05 |
| N-acetyl-2-methylthiazolidine-2,4-dicarboxylic acid 2-ethyl ester | 1.00 | 1.00 | 0.50 | 0.50 | 0.50 | | |
| N-acetyl-2-methylthiazolidine-2,4-dicarboxylic acid | | | | | | | |
| kojic add | | | | | | | |
| arbutin | | | | | | | |
| chamomilla recutita extract | | | | | | | |
| rcinol | | | | | | | |
| GSH | | | | | | | |
| tranexamic acid | | | | | | | |
| 4-methoxy salicylic acid | | | | | | | |
| safflower seed extract | 0.50 | | | | | | |
| ascorbic acid 2-glucoside | | 0.20 | | | | | |
| oligosaccharide | | | 1.00 | | | | |
| ellagic acid | | | | 0.05 | | 0.05 | |
| hydroquinone | | | | | 0.01 | | 0.01 |
| ammonium N-acetyl-2-methylthiazolidine-2,4-dicarboxylic acid 2-ethyl ester | | | | | | 0.50 | |
| diammonium N-acetyl-2-methylthiazolidine-2,4-dicarboxylic acid | | | | | | | 0.20 |
| extract *1 | 0.10 | 0.10 | 0.10 | 0.10 | 0.10 | 0.10 | 0.10 |
| methylparaben | q.s. | q.s. | q.s. | q.s. | q.s. | q.s. | q.s. |
| phenoxyethanol | q.s. | q.s. | q.s. | q.s. | q.s. | q.s. | q.s. |
| trisodium edetate | q.s. | q.s. | q.s. | q.s. | q.s. | q.s. | q.s. |

TABLE 9-continued

| sunscreen cosmetic (in wt %, total amount 100) | | | | | | | |
|---|---|---|---|---|---|---|---|
| butylethylpropanediol | 0.50 | 0.50 | 0.50 | 0.50 | 0.50 | 0.50 | 0.50 |
| 10% arginine aqueous solution | q.s. | q.s. | q.s. | q.s. | q.s. | q.s. | q.s. |
| purified water | balance | balance | balance | balance | balance | balance | balance |
| flavor | q.s. | q.s. | q.s. | q.s. | q.s. | q.s. | q.s. |

TABLE 10

| lotion (in wt %, total amount 100) | | | | | | | | | | | | |
|---|---|---|---|---|---|---|---|---|---|---|---|---|
| component | Form. Ex. 95 | Form. Ex. 96 | Form. Ex. 97 | Form. Ex. 98 | Form. Ex. 99 | Form. Ex. 100 | Form. Ex. 101 | Form. Ex. 102 | Form. Ex. 103 | Form. Ex. 104 | Form. Ex. 105 | Form. Ex. 106 |
| glycerol | 2.00 | 2.00 | 2.00 | 2.00 | 2.00 | 2.00 | 2.00 | 2.00 | 2.00 | 2.00 | 2.00 | 2.00 |
| diglycerol | 2.00 | 2.00 | 2.00 | 2.00 | 2.00 | 2.00 | 2.00 | 2.00 | 2.00 | 2.00 | 2.00 | 2.00 |
| BG | 2.00 | 2.00 | 2.00 | 2.00 | 2.00 | 2.00 | 2.00 | 2.00 | 2.00 | 2.00 | 2.00 | 2.00 |
| DPG | 2.00 | 2.00 | 2.00 | 2.00 | 2.00 | 2.00 | 2.00 | 2.00 | 2.00 | 2.00 | 2.00 | 2.00 |
| PEG-400 | 0.50 | 0.50 | 0.50 | 0.50 | 0.50 | 0.50 | 0.50 | 0.50 | 0.50 | 0.50 | 0.50 | 0.50 |
| jojoba oil | 0.50 | 0.50 | 0.50 | 0.50 | 0.50 | 0.50 | 0.50 | 0.50 | 0.50 | 0.50 | 0.50 | 0.50 |
| di(phytosteryl/octyldodecyl)-lauroyl glutamate | 0.20 | 0.20 | 0.20 | 0.20 | 0.20 | 0.20 | 0.20 | 0.20 | 0.20 | 0.20 | 0.20 | 0.20 |
| di(octyldodecyl/phytosteryl/behenyl)lauroyl glutamate | 0.20 | 0.20 | 0.20 | 0.20 | 0.20 | 0.20 | 0.20 | 0.20 | 0.20 | 0.20 | 0.20 | 0.20 |
| (phytosteryl/decyltetradecyl)-myristoyl methyl β alaninate | 0.20 | 0.20 | 0.20 | 0.20 | 0.20 | 0.20 | 0.20 | 0.20 | 0.20 | 0.20 | 0.20 | 0.20 |
| isopropyl lauroyl sarcosinate | 0.20 | 0.20 | 0.20 | 0.20 | 0.20 | 0.20 | 0.20 | 0.20 | 0.20 | 0.20 | 0.20 | 0.20 |
| PPG-6 decyltetradeceth-30 | 1.00 | 1.00 | 1.00 | 1.00 | 1.00 | 1.00 | 1.00 | 1.00 | 1.00 | 1.00 | 1.00 | 1.00 |
| PEG-40 hydrogenated castor oil | 2.00 | 2.00 | 2.00 | 2.00 | 2.00 | 2.00 | 2.00 | 2.00 | 2.00 | 2.00 | 2.00 | 2.00 |
| pyroglutamate isostearate | | | | | | | | | | | | |
| (acrylic acid/alkyl acrylate (C10-30)) copolymer | 0.01 | 0.01 | 0.01 | 0.01 | 0.01 | 0.01 | 0.01 | 0.01 | 0.01 | 0.01 | 0.01 | 0.01 |
| carboxyvinyl polymer | 0.01 | 0.01 | 0.01 | 0.01 | 0.01 | 0.01 | 0.01 | 0.01 | 0.01 | 0.01 | 0.01 | 0.01 |
| hydroxypropylmethylcellulose | 0.10 | 0.10 | 0.10 | 0.10 | 0.10 | 0.10 | 0.10 | 0.10 | 0.10 | 0.10 | 0.10 | 0.10 |
| xanthan gum | 0.10 | 0.10 | 0.10 | 0.10 | 0.10 | 0.10 | 0.10 | 0.10 | 0.10 | 0.10 | 0.10 | 0.10 |
| arginine | 0.50 | 0.05 | 0.05 | 0.05 | 0.05 | 0.05 | 0.05 | 0.05 | 0.05 | 0.05 | 0.05 | 0.05 |
| glutamic acid | 0.05 | 0.05 | 0.05 | 0.05 | 0.05 | 0.05 | 0.05 | 0.05 | 0.05 | 0.05 | 0.05 | 0.05 |
| aspartic acid | 0.05 | 0.05 | 0.05 | 0.05 | 0.05 | 0.05 | 0.05 | 0.05 | 0.05 | 0.05 | 0.05 | 0.05 |
| valine | 0.05 | 0.05 | 0.05 | 0.05 | 0.05 | 0.05 | 0.05 | 0.05 | 0.05 | 0.05 | 0.05 | 0.05 |
| leucine | 0.05 | 0.05 | 0.05 | 0.05 | 0.05 | 0.05 | 0.05 | 0.05 | 0.05 | 0.05 | 0.05 | 0.05 |
| isoleucine | 0.05 | 0.05 | 0.05 | 0.05 | 0.05 | 0.05 | 0.05 | 0.05 | 0.05 | 0.05 | 0.05 | 0.05 |
| serine | 0.05 | 0.05 | 0.05 | 0.05 | 0.05 | 0.05 | 0.05 | 0.05 | 0.05 | 0.05 | 0.05 | 0.05 |
| glycine | 0.05 | 0.05 | 0.05 | 0.05 | 0.05 | 0.05 | 0.05 | 0.05 | 0.05 | 0.05 | 0.05 | 0.05 |
| alanine | 0.05 | 0.05 | 0.05 | 0.05 | 0.05 | 0.05 | 0.05 | 0.05 | 0.05 | 0.05 | 0.05 | 0.05 |
| proline | 0.05 | 0.05 | 0.05 | 0.05 | 0.05 | 0.05 | 0.05 | 0.05 | 0.05 | 0.05 | 0.05 | 0.05 |
| threonine | 0.05 | 0.05 | 0.05 | 0.05 | 0.05 | 0.05 | 0.05 | 0.05 | 0.05 | 0.05 | 0.05 | 0.05 |
| lysin | 0.05 | 0.50 | 0.05 | 0.05 | 0.05 | 0.05 | 0.05 | 0.05 | 0.05 | 0.05 | 0.05 | 0.05 |
| histidine | 0.05 | 0.05 | 0.50 | 0.50 | 0.50 | 0.50 | 0.50 | 0.50 | 0.50 | 0.50 | 0.50 | 0.50 |
| phenylalanine | 0.05 | 0.05 | 0.05 | 0.05 | 0.05 | 0.05 | 0.05 | 0.05 | 0.05 | 0.05 | 0.05 | 0.05 |
| tryptophan | 0.05 | 0.05 | 0.05 | 0.05 | 0.05 | 0.05 | 0.05 | 0.05 | 0.05 | 0.05 | 0.05 | 0.05 |
| tyrosine | 0.05 | 0.05 | 0.05 | 0.05 | 0.05 | 0.05 | 0.05 | 0.05 | 0.05 | 0.05 | 0.05 | 0.05 |
| acetylglutamine | 0.05 | 0.05 | 0.05 | 0.05 | 0.05 | 0.05 | 0.05 | 0.05 | 0.05 | 0.05 | 0.05 | 0.05 |
| asparagine | 0.05 | 0.05 | 0.05 | 0.05 | 0.05 | 0.05 | 0.05 | 0.05 | 0.05 | 0.05 | 0.05 | 0.05 |
| acetylcysteine | 0.05 | 0.05 | 0.05 | 0.05 | 0.05 | 0.05 | 0.05 | 0.05 | 0.05 | 0.05 | 0.05 | 0.05 |
| methionine | 0.05 | 0.05 | 0.05 | 0.05 | 0.05 | 0.05 | 0.05 | 0.05 | 0.05 | 0.05 | 0.05 | 0.05 |
| sodium pyrrolidone carboxylate | 0.05 | 0.05 | 0.05 | 0.05 | 0.05 | 0.05 | 0.05 | 0.05 | 0.05 | 0.05 | 0.05 | 0.05 |
| zinc pyrrolidone carboxylate | 0.05 | 0.05 | 0.05 | 0.05 | 0.05 | 0.05 | 0.05 | 0.05 | 0.05 | 0.05 | 0.05 | 0.05 |
| sodium polyaspartate | 0.05 | 0.05 | 0.05 | 0.05 | 0.05 | 0.05 | 0.05 | 0.05 | 0.05 | 0.05 | 0.05 | 0.05 |
| glutamyllysine | 2.00 | 2.00 | 2.00 | 2.00 | 2.00 | 2.00 | 2.00 | 2.00 | 2.00 | 2.00 | 2.00 | 2.00 |
| pyridoxylserine | 0.05 | 0.05 | 0.05 | 0.05 | 0.05 | 0.05 | 0.05 | 0.05 | 0.05 | 0.05 | 0.05 | 0.05 |
| pyrrolidone carboxylic acid salt of cocoyl arginine ethyl | 0.05 | 0.05 | 0.05 | 0.05 | 0.05 | 0.05 | 0.05 | 0.05 | 0.05 | 0.05 | 0.05 | 0.05 |
| taurine | 0.05 | 0.05 | 0.05 | 0.05 | 0.05 | 0.05 | 0.05 | 0.05 | 0.05 | 0.05 | 0.05 | 0.05 |
| carnosine | 0.05 | 0.05 | 0.05 | 0.05 | 0.05 | 0.05 | 0.05 | 0.05 | 0.05 | 0.05 | 0.05 | 0.05 |
| citrulline | 0.05 | 0.05 | 0.05 | 0.05 | 0.05 | 0.05 | 0.05 | 0.05 | 0.05 | 0.05 | 0.05 | 0.05 |
| ornithine | 0.05 | 0.05 | 0.05 | 0.05 | 0.05 | 0.05 | 0.05 | 0.05 | 0.05 | 0.05 | 0.05 | 0.05 |
| betaine | 0.05 | 0.05 | 0.05 | 0.05 | 0.05 | 0.05 | 0.05 | 0.05 | 0.05 | 0.05 | 0.05 | 0.05 |
| N-acetyl-2-methylthiazolidine-2,4-dicarboxylic acid 2-ethyl ester | | | | | | | 0.50 | 0.50 | 1.00 | 1.00 | | |
| N-acetyl-2-methylthiazolidine-2,4-dicarboxylic acid | 0.50 | 1.00 | 1.00 | 1.00 | 1.50 | 1.50 | | | | | | |
| glycyrrhizic acid 2K | 0.10 | 0.10 | 0.10 | 0.10 | 0.10 | 0.10 | 0.10 | 0.10 | 0.10 | 0.10 | 0.10 | 0.10 |
| kojic acid | 1.00 | | | | | | | | | | | |
| arbutin | | 1.00 | | | | | | | | | | |
| *chamomilla recutita* extract | | | 0.10 | | | | | | | | | |
| rcinol | | | | 0.50 | | | | | | | | |
| GSH | | | | | 0.50 | | | | | | | |

TABLE 10-continued lotion (in wt %, total amount 100)

| component | Form. Ex. 95 | Form. Ex. 96 | Form. Ex. 97 | Form. Ex. 98 | Form. Ex. 99 | Form. Ex. 100 | Form. Ex. 101 | Form. Ex. 102 | Form. Ex. 103 | Form. Ex. 104 | Form. Ex. 105 | Form. Ex. 106 |
|---|---|---|---|---|---|---|---|---|---|---|---|---|
| tranexamic acid | | | | | | 0.50 | | | | | | |
| 4-methoxy salicylic acid | | | | | | | 1.00 | | | | | |
| safflower seed extract | | | | | | | | 1.00 | | | | |
| magnesium ascorbic acid phosphate | | | | | | | | | | 0.10 | | 0.10 |
| oligosaccharide | | | | | | | | | | | 2.00 | | 2.00 |
| ammonium N-acetyl-2-methylthiazolidine-2,4-dicarboxylic acid 2-ethyl ester | | | | | | | | | | | 1.50 | |
| diammonium N-acetyl-2-methylthiazolidine-2,4-dicarboxylic acid | | | | | | | | | | | | 1.50 |
| astaxanthin | 0.10 | 0.10 | 0.10 | 0.10 | 0.10 | 0.10 | 0.10 | 0.10 | 0.10 | 0.10 | 0.10 | 0.10 |
| panthenol | 0.10 | 0.10 | 0.10 | 0.10 | 0.10 | 0.10 | 0.10 | 0.10 | 0.10 | 0.10 | 0.10 | 0.10 |
| niacinamide | 0.10 | 0.10 | 0.10 | 0.10 | 0.10 | 0.10 | 0.10 | 0.10 | 0.10 | 0.10 | 0.10 | 0.10 |
| pyridoxine hydrochloride | 0.10 | 0.10 | 0.10 | 0.10 | 0.10 | 0.10 | 0.10 | 0.10 | 0.10 | 0.10 | 0.10 | 0.10 |
| retinol | 0.10 | 0.10 | 0.10 | 0.10 | 0.10 | 0.10 | 0.10 | 0.10 | 0.10 | 0.10 | 0.10 | 0.10 |
| carotene | 0.10 | 0.10 | 0.10 | 0.10 | 0.10 | 0.10 | 0.10 | 0.10 | 0.10 | 0.10 | 0.10 | 0.10 |
| riboflavin | 0.10 | 0.10 | 0.10 | 0.10 | 0.10 | 0.10 | 0.10 | 0.10 | 0.10 | 0.10 | 0.10 | 0.10 |
| tocopherol | 0.10 | 0.10 | 0.10 | | 0.10 | | 0.10 | 0.10 | 0.10 | | 0.10 | |
| tocopherol acetate | | | | 0.10 | | 0.10 | | | | 0.10 | | 0.10 |
| ubiquinone | 0.10 | 0.10 | 0.10 | 0.10 | 0.10 | 0.10 | 0.10 | 0.10 | 0.10 | 0.10 | 0.10 | 0.10 |
| sodium hyaluronate | 0.10 | 0.10 | 0.10 | 0.10 | 0.10 | 0.10 | 0.10 | 0.10 | 0.10 | 0.10 | 0.10 | 0.10 |
| water-soluble collagen | 0.10 | 0.10 | 0.10 | 0.10 | 0.10 | 0.10 | 0.10 | 0.10 | 0.10 | 0.10 | 0.10 | 0.10 |
| sodium chondroitin sulfate | 0.10 | 0.10 | 0.10 | 0.10 | 0.10 | 0.10 | 0.10 | 0.10 | 0.10 | 0.10 | 0.10 | 0.10 |
| *lactobacillus*/milk ferment filtrate | 3.00 | 3.00 | 3.00 | 3.00 | 3.00 | 3.00 | 3.00 | 3.00 | 3.00 | 3.00 | 3.00 | 3.00 |
| whey | 1.00 | 1.00 | 1.00 | 1.00 | 1.00 | 1.00 | 1.00 | 1.00 | 1.00 | 1.00 | 1.00 | 1.00 |
| yogurt extract | 1.00 | 1.00 | 1.00 | 1.00 | 1.00 | 1.00 | 1.00 | 1.00 | 1.00 | 1.00 | 1.00 | 1.00 |
| hydrolyzed sodium caseinate | 0.10 | 0.10 | 0.10 | 0.10 | 0.10 | 0.10 | 0.10 | 0.10 | 0.10 | 0.10 | 0.10 | 0.10 |
| fermented soybean extract | 0.10 | 0.10 | 0.10 | 0.10 | 0.10 | 0.10 | 0.10 | 0.10 | 0.10 | 0.10 | 0.10 | 0.10 |
| extract *1 | 0.10 | 0.10 | 0.10 | 0.10 | 0.10 | 0.10 | 0.10 | 0.10 | 0.10 | 0.10 | 0.10 | 0.10 |
| benzalkonium chloride | 0.10 | 0.10 | 0.10 | 0.10 | 0.10 | 0.10 | 0.10 | 0.10 | 0.10 | 0.10 | 0.10 | 0.10 |
| triclosan | 0.10 | 0.10 | 0.10 | 0.10 | 0.10 | 0.10 | 0.10 | 0.10 | 0.10 | 0.10 | 0.10 | 0.10 |
| salicylic acid | 0.10 | 0.10 | 0.10 | 0.10 | 0.10 | 0.10 | 0.10 | 0.10 | 0.10 | 0.10 | 0.10 | 0.10 |
| citric acid | 0.10 | 0.10 | 0.10 | 0.10 | 0.10 | 0.10 | 0.10 | 0.10 | 0.10 | 0.10 | 0.10 | 0.10 |
| bisabolol | 0.10 | 0.10 | 0.10 | 0.10 | 0.10 | 0.10 | 0.10 | 0.10 | 0.10 | 0.10 | 0.10 | 0.10 |
| EDTA-2Na | 0.10 | 0.10 | 0.10 | 0.10 | 0.10 | 0.10 | 0.10 | 0.10 | 0.10 | 0.10 | 0.10 | 0.10 |
| phenoxyethanol | 0.30 | 0.30 | 0.30 | 0.30 | 0.30 | 0.30 | 0.30 | 0.30 | 0.30 | 0.30 | 0.30 | 0.30 |
| ethanol | 1.00 | 1.00 | 1.00 | 1.00 | 1.00 | 1.00 | 1.00 | 1.00 | 1.00 | 1.00 | 1.00 | 1.00 |
| potassium hydroxide | q.s. | q.s. | q.s. | q.s. | q.s. | q.s. | q.s. | q.s. | q.s. | q.s. | q.s. | q.s. |
| flavor | q.s. | q.s. | q.s. | q.s. | q.s. | q.s. | q.s. | q.s. | q.s. | q.s. | q.s. | q.s. |
| purified water | balance | balance | balance | balance | balance | balance | balance | balance | balance | balance | balance | balance |

TABLE 11 lotion (in wt %, total amount 100)

| component | Form. Ex. 107 | Form. Ex. 108 | Form. Ex. 109 | Form. Ex. 110 | Form. Ex. 111 | Form. Ex. 112 | Form. Ex 113 | Form. Ex. 114 | Form. Ex. 115 | Form. Ex. 116 | Form. Ex. 117 | Form. Ex. 118 |
|---|---|---|---|---|---|---|---|---|---|---|---|---|
| ethanol | 10.00 | 10.00 | 10.00 | 10.00 | 10.00 | 10.00 | 10.00 | 10.00 | 10.00 | 10.00 | 10.00 | 10.00 |
| DPG | 1.00 | 1.00 | 1.00 | 1.00 | 1.00 | 1.00 | 1.00 | 1.00 | 1.00 | 1.00 | 1.00 | 1.00 |
| BG | 0.60 | 0.60 | 0.60 | 0.60 | 0.60 | 0.60 | 0.60 | 0.60 | 0.60 | 0.60 | 0.60 | 0.60 |
| PEG-20 | 1.00 | 1.00 | 1.00 | 1.00 | 1.00 | 1.00 | 1.00 | 1.00 | 1.00 | 1.00 | 1.00 | 1.00 |
| polyoxyethylene methyl glucoside | 1.00 | 1.00 | 1.00 | 1.00 | 1.00 | 1.00 | 1.00 | 1.00 | 1.00 | 1.00 | 1.00 | 1.00 |
| isostearic acid | 0.20 | 0.20 | 0.20 | 0.20 | 0.20 | 0.20 | 0.20 | 0.20 | 0.20 | 0.20 | 0.20 | 0.20 |
| triethylhexanoin | 0.30 | 0.30 | 0.30 | 0.30 | 0.30 | 0.30 | 0.30 | 0.30 | 0.30 | 0.30 | 0.30 | 0.30 |
| polyoxyethylene (30) phytosterol | 0.09 | 0.09 | 0.09 | 0.09 | 0.09 | 0.09 | 0.09 | 0.09 | 0.09 | 0.09 | 0.09 | 0.09 |
| sorbitan sesqui-isostearate | 0.03 | 0.03 | 0.03 | 0.03 | 0.03 | 0.03 | 0.03 | 0.03 | 0.03 | 0.03 | 0.03 | 0.03 |
| citric acid | 0.05 | 0.05 | 0.05 | 0.05 | 0.05 | 0.05 | 0.05 | 0.05 | 0.05 | 0.05 | 0.05 | 0.05 |
| sodium citrate | 0.20 | 0.20 | 0.20 | 0.20 | 0.20 | 0.20 | 0.20 | 0.20 | 0.20 | 0.20 | 0.20 | 0.20 |
| potassium hydroxide | 0.40 | 0.40 | 0.40 | 0.40 | 0.40 | 0.40 | 0.40 | 0.40 | 0.40 | 0.40 | 0.40 | 0.40 |
| glycyrrhizic acid 2K | 0.10 | 0.10 | 0.10 | 0.10 | 0.10 | 0.10 | 0.10 | 0.10 | 0.10 | 0.10 | 0.10 | 0.10 |
| arginine hydrochloride | 0.10 | 0.10 | 0.10 | 0.10 | 0.10 | 0.10 | 0.10 | 0.10 | 0.10 | 0.10 | 0.10 | 0.10 |
| kojic acid | 1.00 | | | | | | | | | | | |
| arbutin | | 1.00 | | | | | | | | | | |
| *chamomilla recutita* extract | | | 0.10 | | | | | | | | | |
| rcinol | | | | 0.50 | | | | | | | | |
| GSH | | | | | 0.50 | | | | | | | |
| tranexamic acid | | | | | | 0.50 | | | | | | |
| 4-methoxy salicylic acid | | | | | | | 1.00 | | 1.00 | | | |

TABLE 11-continued lotion (in wt %, total amount 100)

| component | Form. Ex. 107 | Form. Ex. 108 | Form. Ex. 109 | Form. Ex. 110 | Form. Ex. 111 | Form. Ex. 112 | Form. Ex 113 | Form. Ex. 114 | Form. Ex. 115 | Form. Ex. 116 | Form. Ex. 117 | Form. Ex. 118 |
|---|---|---|---|---|---|---|---|---|---|---|---|---|
| safflower seed extract | | | | | | | | 1.00 | | 1.00 | | |
| N-acetyl-2-methylthiazolidine-2,4-dicarboxylic acid 2-ethyl ester calcium salt | | | | | | | | | 1.00 | | | |
| N-acetyl-2-methylthiazolidine-2,4-dicarboxylic acid calcium salt | | | | | | | | | | 2.00 | | |
| ellagic acid | | | | | | | | | | | 0.10 | |
| hydroquinone | | | | | | | | | | | | 0.50 |
| N-acetyl-2-methylthiazolidine-2,4-dicarboxylic acid | | | | | | | 0.50 | 0.50 | | | 1.50 | 1.50 |
| N-acetyl-2-methylthiazolidine-2,4-dicarboxylic acid 2-ethyl ester | 0.50 | 1.00 | 1.00 | 1.00 | 1.50 | 1.50 | | | | | | |
| extract *1 | 0.10 | 0.10 | 0.10 | 0.10 | 0.10 | 0.10 | 0.10 | 0.10 | 0.10 | 0.10 | 0.10 | 0.10 |
| trisodium edetate | 0.05 | 0.05 | 0.05 | 0.05 | 0.05 | 0.05 | 0.05 | 0.05 | 0.05 | 0.05 | 0.05 | 0.05 |
| 2-ethylhexyl paramethoxycinnamate | 0.01 | 0.01 | 0.01 | 0.01 | 0.01 | 0.01 | 0.01 | 0.01 | 0.01 | 0.01 | 0.01 | 0.01 |
| dibutylhydroxytoluene | q.s. | q.s. | q.s. | q.s. | q.s. | q.s. | q.s. | q.s. | q.s. | q.s. | q.s. | q.s. |
| methylparaben | q.s. | q.s. | q.s. | q.s. | q.s. | q.s. | q.s. | q.s. | q.s. | q.s. | q.s. | q.s. |
| potassium hydroxide | q.s. | q.s. | q.s. | q.s. | q.s. | q.s. | q.s. | q.s. | q.s. | q.s. | q.s. | q.s. |
| deep ocean water | 3.00 | 3.00 | 3.00 | 3.00 | 3.00 | 3.00 | 3.00 | 3.00 | 3.00 | 3.00 | 3.00 | 3.00 |
| purified water | balance | balance | balance | balance | balance | balance | balance | balance | balance | balance | balance | balance |
| flavor | q.s. | q.s. | q.s. | q.s. | q.s. | q.s. | q.s. | q.s. | q.s. | q.s. | q.s. | q.s. |

TABLE 12 foaming facial cleanser (in wt %, total amount 100)

| component | Form. Ex. 119 | Form. Ex. 120 | Form. Ex. 121 | Form. Ex. 122 | Form. Ex. 123 | Form. Ex. 124 | Form. Ex. 125 |
|---|---|---|---|---|---|---|---|
| sodium cocoyl glycinate | 2.15 | | | | 2.15 | | |
| TEA cocoyl glutamate | | 10.00 | | | | 10.00 | |
| sodium cocoyl alaninate | | | 5.80 | | | | 5.80 |
| TEA cocoyl alaninate | | | | 9.00 | | | |
| lauramidopropyl hydroxysultaine | | | | 1.00 | | | |
| sodium lauroamphoacetate | 3.00 | | 4.80 | | 3.00 | | 4.80 |
| cocamide DEA | | 2.00 | | | | 2.00 | |
| BG | 5.00 | 5.00 | 7.00 | 5.00 | 5.00 | 5.00 | 7.00 |
| glycerol | 3.00 | | 3.00 | | 3.00 | | 3.00 |
| Polyquaternium-39 | 0.10 | | 0.10 | | 0.10 | | 0.10 |
| N-acetyl-2-methylthiazolidine-2,4-dicarboxylic acid 2-ethyl ester | 1.00 | 1.00 | 1.00 | 2.00 | 2.00 | 2.00 | |
| N-acetyl-2-methytlhiazolidine-2,4-dicarboxylic acid | | | | | | | |
| kojic acid | 0.50 | | | | | | |
| arbutin | | 0.50 | | | | | |
| chamomilla recutita extract | | | 0.10 | | | | |
| rcinol | | | | 0.20 | | | |
| GSH | | | | | 0.50 | | 0.50 |
| tranexamic acid | | | | | | 1.00 | |
| N-acetyl-2-methylthiazolidine-2,4-dicarboxylic acid 2-ethyl ester calcium salt | | | | | | | 1.00 |
| N-acetyl-2-methylthiazolidine-2,4-dicarboxylic acid calcium salt | | | | | | | |
| ascorbic acid 2-glucoside | | | | | | | |
| oligosaccharide | | | | | | | |
| ellagic acid | | | | | | | |
| hydroquinone | | | | | | | |
| saxifraga sarmentosa extract | | | | | | | |
| cetyl ascorbyl ether | | | | | | | |
| PEG-40 hydrogenated castor oil | | 2.00 | | | | 2.00 | |
| pyroglutamate isostearate | | | | | | | |
| sodium pyrrolidone carboxylate | | 0.50 | | 0.50 | | 0.50 | |
| extract *1 | 0.10 | 0.10 | 0.10 | 0.10 | 0.10 | 0.10 | 0.10 |
| citric acid | | | 0.05 | 0.25 | | | 0.05 |
| sodium hydroxide | q.s. | q.s. | q.s. | q.s. | q.s. | q.s. | |
| methylparaben | 0.20 | 0.20 | 0.20 | 0.20 | 0.20 | 0.20 | 0.20 |
| sodium benzoate | | 0.20 | | | | 0.20 | |
| EDTA-2Na | 0.01 | | 0.01 | 0.01 | 0.01 | | 0.01 |
| purified water | balance | balance | balance | balance | balance | balance | balance |

TABLE 12-continued foaming facial cleanser (in wt %, total amount 100)

| component | Form. Ex. 126 | Form. Ex. 127 | Form. Ex. 128 | Form. Ex. 129 | Form. Ex. 130 | Form. Ex. 131 | Form. Ex. 132 |
|---|---|---|---|---|---|---|---|
| sodium cocoyl glycinate | | 2.15 | | | | 2.15 | |
| TEA cocoyl glutamate | | | 10.00 | | | | 10.00 |
| sodium cocoyl alaninate | | | | 5.80 | | | |
| TEA cocoyl alaninate | 9.00 | | | | 9.00 | | |
| lauramidopropyl hydroxysultaine | 1.00 | | | | 1.00 | | |
| sodium lauroamphoacetate | | 3.00 | 2.00 | 4.80 | | 3.00 | 2.00 |
| cocamide DEA | | | 2.00 | | | | 2.00 |
| BG | 5.00 | 5.00 | 5.00 | 7.00 | 5.00 | 5.00 | 5.00 |
| glycerol | | 3.00 | | 3.00 | | 3.00 | |
| Polyquaternium-39 | | 0.10 | | 0.10 | | 0.10 | |
| N-acetyl-2-methylthiazolidine-2,4-dicarboxylic acid 2-ethyl ester | | | | | | | |
| N-acetyl-2-methytlhiazolidine-2,4-dicarboxylic acid | | 1.00 | 1.00 | 2.00 | 2.00 | 2.00 | 2.00 |
| kojic acid | | | | | | | |
| arbutin | | | | | | | |
| chamomilla recutita extract | | | | | | | |
| rcinol | | | | | | | |
| GSH | | | | | | | |
| tranexamic acid | 1.00 | | | | | | |
| N-acetyl-2-methylthiazolidine-2,4-dicarboxylic acid 2-ethyl ester calcium salt | | | | | | | |
| N-acetyl-2-methylthiazolidine-2,4-dicarboxylic acid calcium salt | 2.00 | | | | | | |
| ascorbic acid 2-glucoside | | 0.20 | | | | | |
| oligosaccharide | | | 1.00 | | | | |
| ellagic acid | | | | 0.05 | | | |
| hydroquinone | | | | | 0.01 | | |
| saxifraga sarmentosa extract | | | | | | 4.00 | |
| cetyl ascorbyl ether | | | | | | | 0.10 |
| PEG-40 hydrogenated castor oil pyroglutamate isostearate | | | 2.00 | | | | 2.00 |
| sodium pyrrolidone carboxylate | 0.50 | | 0.50 | | 0.50 | | 0.50 |
| extract *1 | 0.10 | 0.10 | 0.10 | 0.10 | 0.10 | 0.10 | 0.10 |
| citric acid | 0.25 | | | 0.05 | 0.25 | | |
| sodium hydroxide | q.s. | q.s. | q.s. | q.s. | q.s. | q.s. | q.s. |
| methylparaben | 0.20 | 0.20 | 0.20 | 0.20 | 0.20 | 0.20 | 0.20 |
| sodium benzoate | | | 0.20 | | | | 0.20 |
| EDTA-2Na | 0.01 | 0.01 | | 0.01 | 0.01 | 0.01 | |
| purified water | balance | balance | balance | balance | balance | balance | balance |

TABLE 13 cleansing foam (in wt %, total amount 100)

| component | Form. Ex. 133 | Form. Ex. 134 | Form. Ex. 135 | Form. Ex. 136 | Form. Ex. 137 | Form. Ex. 138 | Form. Ex. 139 |
|---|---|---|---|---|---|---|---|
| sodium N-acyl glutamate | 20.00 | 20.00 | 20.00 | 20.00 | 20.00 | 20.00 | 20.00 |
| Glycerol | 10.00 | 10.00 | 10.00 | 10.00 | 10.00 | 10.00 | 10.00 |
| di(octyldodecyl/phytosteryl/behenyl)-lauroyl glutamate | 0.01 | 0.01 | 0.01 | 0.01 | 0.01 | 0.01 | 0.01 |
| di(cholesteryl/behenyl/octyldodecyl)-lauroyl glutamate | 0.01 | 0.01 | 0.01 | 0.01 | 0.01 | 0.01 | 0.01 |
| PEG-8 | 15.00 | 15.00 | 15.00 | 15.00 | 15.00 | 15.00 | 15.00 |
| DPG | 10.00 | 10.00 | 10.00 | 10.00 | 10.00 | 10.00 | 10.00 |
| acylmethyltaurine | 5.00 | 5.00 | 5.00 | 5.00 | 5.00 | 5.00 | 5.00 |
| POE/POP block polymer | 5.00 | 5.00 | 5.00 | 5.00 | 5.00 | 5.00 | 5.00 |
| POE (15) oleyl alcohol ether | 3.00 | 3.00 | 3.00 | 3.00 | 3.00 | 3.00 | 3.00 |
| lanolin derivative | 2.00 | 2.00 | 2.00 | 2.00 | 2.00 | 2.00 | 2.00 |
| N-acetyl-2-methylthiazolidine-2,4-dicarboxylic acid 2-ethyl ester | | | | | | | |
| N-acetyl-2-methylthiazolidine-2,4-dicarboxylic acid | 1.00 | 1.00 | 1.00 | 1.00 | | | 2.00 |
| kojic acid | 0.50 | | | | | | |
| arbutin | | 0.50 | | | | | |

TABLE 13-continued cleansing foam (in wt %, total amount 100)

| component | | | | | | | |
|---|---|---|---|---|---|---|---|
| chamomilla recutita extract | | 0.10 | | 0.10 | | | |
| rcinol | | | 0.20 | | 0.20 | | |
| N-acetyl-2-methylthiazolidine-2,4-dicarboxylic acid 2-ethyl ester silver salt | | | | 1.00 | | | |
| N-acetyl-2-methylthiazolidine-2,4-dicarboxylic acid silver salt | | | | | 2.00 | | |
| 4-methoxy salicylic acid | | | | | | 1.0e0 | |
| safflower seed extract | | | | | | | |
| ascorbic acid 2-glucoside | | | | | | | |
| oligosaccharide | | | | | | | |
| ellagic acid | | | | | | | |
| hydroquinone | | | | | | | |
| saxifraga sarmentosa extract | | | | | | | |
| cetyl ascorbyl ether | | | | | | | |
| arginine | 0.70 | 0.70 | 0.70 | 0.70 | 0.70 | 0.70 | 0.70 |
| EDTA-2Na | 0.05 | 0.05 | 0.05 | 0.05 | 0.05 | 0.05 | 0.05 |
| leucine | 0.01 | 0.01 | 0.01 | 0.01 | 0.01 | 0.01 | 0.01 |
| isoleucine | 0.01 | 0.01 | 0.01 | 0.01 | 0.01 | 0.01 | 0.01 |
| valine | 0.01 | 0.01 | 0.01 | 0.01 | 0.01 | 0.01 | 0.01 |
| phenylalanine | 0.01 | 0.01 | 0.01 | 0.01 | 0.01 | 0.01 | 0.01 |
| tryptophan | 0.01 | 0.01 | 0.01 | 0.01 | 0.01 | 0.01 | 0.01 |
| aspartic acid | 0.01 | 0.01 | 0.01 | 0.01 | 0.01 | 0.01 | 0.01 |
| sodium glutamate | 0.01 | 0.01 | 0.01 | 0.01 | 0.01 | 0.01 | 0.01 |
| lysine hydrochloride | 0.01 | 0.01 | 0.01 | 0.01 | 0.01 | 0.01 | 0.01 |
| arginine | 0.01 | 0.01 | 0.01 | 0.01 | 0.01 | 0.01 | 0.01 |
| threonine | 0.01 | 0.01 | 0.01 | 0.01 | 0.01 | 0.01 | 0.01 |
| alanine | 0.01 | 0.01 | 0.01 | 0.01 | 0.01 | 0.01 | 0.01 |
| proline | 0.01 | 0.01 | 0.01 | 0.01 | 0.01 | 0.01 | 0.01 |
| serine | 0.01 | 0.01 | 0.01 | 0.01 | 0.01 | 0.01 | 0.01 |
| glycine | 0.01 | 0.01 | 0.01 | 0.01 | 0.01 | 0.01 | 0.01 |
| acetylglutamine | 0.01 | 0.01 | 0.01 | 0.01 | 0.01 | 0.01 | 0.01 |
| histidine | 0.01 | 0.01 | 0.01 | 0.01 | 0.01 | 0.01 | 0.01 |
| pyridoxylserine | 0.01 | 0.01 | 0.01 | 0.01 | 0.01 | 0.01 | 0.01 |
| carnosine | 0.01 | 0.01 | 0.01 | 0.01 | 0.01 | 0.01 | 0.01 |
| acetylmethionine | 0.01 | 0.01 | 0.01 | 0.01 | 0.01 | 0.01 | 0.01 |
| extract *1 | 0.10 | 0.10 | 0.10 | 0.10 | 0.10 | 0.10 | 0.10 |
| zinc pyrrolidone carboxylate | 0.01 | 0.01 | 0.01 | 0.01 | 0.01 | 0.01 | 0.01 |
| sodium pyrrolidone carboxylate | 0.001 | 0.001 | 0.001 | 0.001 | 0.001 | 0.001 | 0.001 |
| pyrrolidonecarboxylic acid salt of cocoyl arginine ethyl | 0.01 | 0.01 | 0.01 | 0.01 | 0.01 | 0.01 | 0.01 |
| methylparaben | 0.25 | 0.25 | 0.25 | 0.25 | 0.25 | 0.25 | 0.25 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

| component | Form. Ex. 140 | Form. Ex. 141 | Form. Ex. 142 | Form. Ex. 143 | Form. Ex. 144 | Form. Ex. 145 | Form. Ex. 146 |
|---|---|---|---|---|---|---|---|
| sodium N-acyl glutamate | 20.00 | 20.00 | 20.00 | 20.00 | 20.00 | 20.00 | 20.00 |
| Glycerol | 10.00 | 10.00 | 10.00 | 10.00 | 10.00 | 10.00 | 10.00 |
| di(octyldodecyl/phytosteryl/behenyl)-lauroyl glutamate | 0.01 | 0.01 | 0.01 | 0.01 | 0.01 | 0.01 | 0.01 |
| di(cholesteryl/behenyl/octyldodecyl)-lauroyl glutamate | 0.01 | 0.01 | 0.01 | 0.01 | 0.01 | 0.01 | 0.01 |
| PEG-8 | 15.00 | 15.00 | 15.00 | 15.00 | 15.00 | 15.00 | 15.00 |
| DPG | 10.00 | 10.00 | 10.00 | 10.00 | 10.00 | 10.00 | 10.00 |
| acylmethyltaurine | 5.00 | 5.00 | 5.00 | 5.00 | 5.00 | 5.00 | 5.00 |
| POE/POP block polymer | 5.00 | 5.00 | 5.00 | 5.00 | 5.00 | 5.00 | 5.00 |
| POE (15) oleyl alcohol ether | 3.00 | 3.00 | 3.00 | 3.00 | 3.00 | 3.00 | 3.00 |
| lanolin derivative | 2.00 | 2.00 | 2.00 | 2.00 | 2.00 | 2.00 | 2.00 |
| N-acetyl-2-methylthiazolidine-2,4-dicarboxylic acid 2-ethyl ester | 1.00 | 1.00 | 1.00 | 1.00 | 1.00 | 2.00 | 2.00 |
| N-acetyl-2-methylthiazolidine-2,4-dicarboxylic acid | | | | | | | |
| kojic acid | | | | | | | |
| arbutin | | | | | | | |
| chamomilla recutita extract | | | | | | | |
| rcinol | | | | | | | |
| N-acetyl-2-methylthiazolidine-2,4-dicarboxylic acid 2-ethyl ester silver salt | | | | | | | |
| N-acetyl-2-methylthiazolidine-2,4-dicarboxylic acid silver salt | | | | | | | |
| 4-methoxy salicylic acid | | | | | | | |
| safflower seed extract | 0.50 | | | | | | |
| ascorbic acid 2-glucoside | | 0.20 | | | | | |
| oligosaccharide | | | 1.00 | | | | |

TABLE 13-continued

| cleansing foam (in wt %, total amount 100) | | | | | | | |
|---|---|---|---|---|---|---|---|
| ellagic acid | | | 0.05 | | | | |
| hydroquinone | | | | 0.01 | | | |
| *saxifraga sarmentosa* extract | | | | | 4.00 | | |
| cetyl ascorbyl ether | | | | | | | 0.10 |
| arginine | 0.70 | 0.70 | 0.70 | 0.70 | 0.70 | 0.70 | 0.70 |
| EDTA-2Na | 0.05 | 0.05 | 0.05 | 0.05 | 0.05 | 0.05 | 0.05 |
| leucine | 0.01 | 0.01 | 0.01 | 0.01 | 0.01 | 0.01 | 0.01 |
| isoleucine | 0.01 | 0.01 | 0.01 | 0.01 | 0.01 | 0.01 | 0.01 |
| valine | 0.01 | 0.01 | 0.01 | 0.01 | 0.01 | 0.01 | 0.01 |
| phenylalanine | 0.01 | 0.01 | 0.01 | 0.01 | 0.01 | 0.01 | 0.01 |
| tryptophan | 0.01 | 0.01 | 0.01 | 0.01 | 0.01 | 0.01 | 0.01 |
| aspartic acid | 0.01 | 0.01 | 0.01 | 0.01 | 0.01 | 0.01 | 0.01 |
| sodium glutamate | 0.01 | 0.01 | 0.01 | 0.01 | 0.01 | 0.01 | 0.01 |
| lysine hydrochloride | 0.01 | 0.01 | 0.01 | 0.01 | 0.01 | 0.01 | 0.01 |
| arginine | 0.01 | 0.01 | 0.01 | 0.01 | 0.01 | 0.01 | 0.01 |
| threonine | 0.01 | 0.01 | 0.01 | 0.01 | 0.01 | 0.01 | 0.01 |
| alanine | 0.01 | 0.01 | 0.01 | 0.01 | 0.01 | 0.01 | 0.01 |
| proline | 0.01 | 0.01 | 0.01 | 0.01 | 0.01 | 0.01 | 0.01 |
| serine | 0.01 | 0.01 | 0.01 | 0.01 | 0.01 | 0.01 | 0.01 |
| glycine | 0.01 | 0.01 | 0.01 | 0.01 | 0.01 | 0.01 | 0.01 |
| acetylglutamine | 0.01 | 0.01 | 0.01 | 0.01 | 0.01 | 0.01 | 0.01 |
| histidine | 0.01 | 0.01 | 0.01 | 0.01 | 0.01 | 0.01 | 0.01 |
| pyridoxylserine | 0.01 | 0.01 | 0.01 | 0.01 | 0.01 | 0.01 | 0.01 |
| carnosine | 0.01 | 0.01 | 0.01 | 0.01 | 0.01 | 0.01 | 0.01 |
| acetylmethionine | 0.01 | 0.01 | 0.01 | 0.01 | 0.01 | 0.01 | 0.01 |
| extract *1 | 0.10 | 0.10 | 0.10 | 0.10 | 0.10 | 0.10 | 0.10 |
| zinc pyrrolidone carboxylate | 0.01 | 0.01 | 0.01 | 0.01 | 0.01 | 0.01 | 0.01 |
| sodium pyrrolidone carboxylate | 0.001 | 0.001 | 0.001 | 0.001 | 0.001 | 0.001 | 0.001 |
| pyrrolidonecarboxylic acid salt of cocoyl arginine ethyl | 0.01 | 0.01 | 0.01 | 0.01 | 0.01 | 0.01 | 0.01 |
| methylparaben | 0.25 | 0.25 | 0.25 | 0.25 | 0.25 | 0.25 | 0.25 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

TABLE 14

| gelly facial mask (in wt %, total amount 100) | | | | | | | |
|---|---|---|---|---|---|---|---|
| component | Form. Ex. 147 | Form. Ex. 148 | Form. Ex. 149 | Form. Ex. 150 | Form. Ex. 151 | Form. Ex. 152 | Form. Ex. 153 |
| PEG-30 | 5.00 | 5.00 | 5.00 | 5.00 | 5.00 | 5.00 | 5.00 |
| di(octyldodecyl/phytosteryl/behenyl)-lauroyl glutamate | 0.01 | 0.01 | 0.01 | 0.01 | 0.01 | 0.01 | 0.01 |
| di(cholesteryl/behenyl/octyldodecyl)-lauroyl glutamate | 0.01 | 0.01 | 0.01 | 0.01 | 0.01 | 0.01 | 0.01 |
| DPG | 5.00 | 5.00 | 5.00 | 5.00 | 5.00 | 5.00 | 5.00 |
| sorbitol | 5.00 | 5.00 | 5.00 | 5.00 | 5.00 | 5.00 | 5.00 |
| carboxyvinyl polymer | 1.00 | 1.00 | 1.00 | 1.00 | 1.00 | 1.00 | 1.00 |
| xanthan gum | 0.50 | 0.50 | 0.50 | 0.50 | 0.50 | 0.50 | 0.50 |
| potassium hydroxide | 0.50 | 0.50 | 0.50 | 0.50 | 0.50 | 0.50 | 0.50 |
| POE lauryl alcohol ether | 1.00 | 1.00 | 1.00 | 1.00 | 1.00 | 1.00 | 1.00 |
| ethanol | 5.00 | 5.00 | 5.00 | 5.00 | 5.00 | 5.00 | 5.00 |
| N-acetyl-2-methylthiazolidine-2,4-dicarboxylic acid 2-ethyl ester | 1.00 | 1.00 | | | 2.00 | 2.00 | 3.00 |
| N-acetyl-2-methylthiazolidine-2,4-dicarboxylic acid | | | | | | | |
| kojic acid | 2.00 | | 2.00 | | | | |
| arbutin | | 2.00 | | 5.00 | | | |
| sodium N-acetyl-2-methylthiazolidine-2,4-dicarboxylic acid 2-ethyl ester | | | 3.00 | | | | |
| disodium N-acetyl-2-methylthiazolidine-2,4-dicarboxylic acid | | | | 4.00 | | | |
| GSH | | | | | 1.00 | | |
| tranexamic acid | | | | | | 1.00 | |
| 4-methoxy salicylic acid | | | | | | | 2.00 |
| safflower seed extract | | | | | | | |
| ascorbic acid 2-glucoside | | | | | | | |
| oligosaccharide | | | | | | | |
| ellagic acid | | | | | | | |
| hydroquinone | | | | | | | |

TABLE 14-continued

| gelly facial mask (in wt %, total amount 100) | | | | | | | |
|---|---|---|---|---|---|---|---|
| *saxifraga sarmentosa* extract | | | | | | | |
| cetyl ascorbyl ether | | | | | | | |
| methylparaben | 0.20 | 0.20 | 0.20 | 0.20 | 0.20 | 0.20 | 0.20 |
| leucine | 0.01 | 0.01 | 0.01 | 0.01 | 0.01 | 0.01 | 0.01 |
| isoleucine | 0.01 | 0.01 | 0.01 | 0.01 | 0.01 | 0.01 | 0.01 |
| valine | 0.01 | 0.01 | 0.01 | 0.01 | 0.01 | 0.01 | 0.01 |
| phenylalanine | 0.01 | 0.01 | 0.01 | 0.01 | 0.01 | 0.01 | 0.01 |
| tryptophan | 0.01 | 0.01 | 0.01 | 0.01 | 0.01 | 0.01 | 0.01 |
| aspartic acid | 0.01 | 0.01 | 0.01 | 0.01 | 0.01 | 0.01 | 0.01 |
| sodium glutamate | 0.01 | 0.01 | 0.01 | 0.01 | 0.01 | 0.01 | 0.01 |
| lysine hydrochloride | 0.01 | 0.01 | 0.01 | 0.01 | 0.01 | 0.01 | 0.01 |
| arginine | 0.01 | 0.01 | 0.01 | 0.01 | 0.01 | 0.01 | 0.01 |
| threonine | 0.01 | 0.01 | 0.01 | 0.01 | 0.01 | 0.01 | 0.01 |
| alanine | 0.01 | 0.01 | 0.01 | 0.01 | 0.01 | 0.01 | 0.01 |
| proline | 0.01 | 0.01 | 0.01 | 0.01 | 0.01 | 0.01 | 0.01 |
| serine | 0.01 | 0.01 | 0.01 | 0.01 | 0.01 | 0.01 | 0.01 |
| glycine | 0.01 | 0.01 | 0.01 | 0.01 | 0.01 | 0.01 | 0.01 |
| acetylglutamine | 0.01 | 0.01 | 0.01 | 0.01 | 0.01 | 0.01 | 0.01 |
| histidine | 0.01 | 0.01 | 0.01 | 0.01 | 0.01 | 0.01 | 0.01 |
| pyridoxylserine | 0.01 | 0.01 | 0.01 | 0.01 | 0.01 | 0.01 | 0.01 |
| carnosine | 0.01 | 0.01 | 0.01 | 0.01 | 0.01 | 0.01 | 0.01 |
| acetylmethionine | 0.01 | 0.01 | 0.01 | 0.01 | 0.01 | 0.01 | 0.01 |
| acetylcysteine | | | | | | | 0.01 |
| extract *1 | 0.10 | 0.10 | 0.10 | 0.10 | 0.10 | 0.10 | 0.10 |
| zinc pyrrolidone carboxylate | 0.01 | 0.01 | 0.01 | 0.01 | 0.01 | 0.01 | 0.01 |
| sodium pyrrolidone carboxylate | 0.001 | 0.001 | 0.001 | 0.001 | 0.001 | 0.001 | 0.001 |
| pyrrolidonecarboxylic acid salt of cocoyl arginine ethyl | 0.01 | 0.01 | 0.01 | 0.01 | 0.01 | 0.01 | 0.01 |
| EDTA-2Na | 0.05 | 0.05 | 0.05 | 0.05 | 0.05 | 0.05 | 0.05 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

| component | Form. Ex. 154 | Form. Ex. 155 | Form. Ex. 156 | Form. Ex. 157 | Form. Ex. 158 | Form. Ex. 159 | Form. Ex. 160 |
|---|---|---|---|---|---|---|---|
| PEG-30 | 5.00 | 5.00 | 5.00 | 5.00 | 5.00 | 5.00 | 5.00 |
| di(octyldodecyl/phytosteryl/behenyl)-lauroyl glutamate | 0.01 | 0.01 | 0.01 | 0.01 | 0.01 | 0.01 | 0.01 |
| di(cholesteryl/behenyl/octyldodecyl)-lauroyl glutamate | 0.01 | 0.01 | 0.01 | 0.01 | 0.01 | 0.01 | 0.01 |
| DPG | 5.00 | 5.00 | 5.00 | 5.00 | 5.00 | 5.00 | 5.00 |
| sorbitol | 5.00 | 5.00 | 5.00 | 5.00 | 5.00 | 5.00 | 5.00 |
| carboxyvinyl polymer | 1.00 | 1.00 | 1.00 | 1.00 | 1.00 | 1.00 | 1.00 |
| xanthan gum | 0.50 | 0.50 | 0.50 | 0.50 | 0.50 | 0.50 | 0.50 |
| potassium hydroxide | 0.50 | 0.50 | 0.50 | 0.50 | 0.50 | 0.50 | 0.50 |
| POE lauryl alcohol ether | 1.00 | 1.00 | 1.00 | 1.00 | 1.00 | 1.00 | 1.00 |
| ethanol | 5.00 | 5.00 | 5.00 | 5.00 | 5.00 | 5.00 | 5.00 |
| N-acetyl-2-methylthiazolidine-2,4-dicarboxylic acid 2-ethyl ester | | | | | | | |
| N-acetyl-2-methylthiazolidine-2,4-dicarboxylic acid | 1.00 | 1.00 | 1.00 | 2.00 | 2.00 | 2.00 | 3.00 |
| kojic acid | | | | | | | |
| arbutin | | | | | | | |
| sodium N-acetyl-2-methylthiazolidine-2,4-dicarboxylic acid 2-ethyl ester | | | | | | | |
| disodium N-acetyl-2-methylthiazolidine-2,4-dicarboxylic acid | | | | | | | |
| GSH | | | | | | | |
| tranexamic acid | | | | | | | |
| 4-methoxy salicylic acid | | | | | | | |
| safflower seed extract | 2.00 | | | | | | |
| ascorbic acid 2-glucoside | | 0.20 | | | | | |
| oligosaccharide | | | 4.00 | | | | |
| ellagic acid | | | | 0.2 | | | |
| hydroquinone | | | | | 1 | | |
| *saxifraga sarmentosa* extract | | | | | | 2 | |
| cetyl ascorbyl ether | | | | | | | 1 |
| methylparaben | 0.20 | 0.20 | 0.20 | 0.20 | 0.20 | 0.20 | 0.20 |
| leucine | 0.01 | 0.01 | 0.01 | 0.01 | 0.01 | 0.01 | 0.01 |
| isoleucine | 0.01 | 0.01 | 0.01 | 0.01 | 0.01 | 0.01 | 0.01 |
| valine | 0.01 | 0.01 | 0.01 | 0.01 | 0.01 | 0.01 | 0.01 |
| phenylalanine | 0.01 | 0.01 | 0.01 | 0.01 | 0.01 | 0.01 | 0.01 |
| tryptophan | 0.01 | 0.01 | 0.01 | 0.01 | 0.01 | 0.01 | 0.01 |
| aspartic acid | 0.01 | 0.01 | 0.01 | 0.01 | 0.01 | 0.01 | 0.01 |

TABLE 14-continued gelly facial mask (in wt %, total amount 100)

| | | | | | | | |
|---|---|---|---|---|---|---|---|
| sodium glutamate | 0.01 | 0.01 | 0.01 | 0.01 | 0.01 | 0.01 | 0.01 |
| lysine hydrochloride | 0.01 | 0.01 | 0.01 | 0.01 | 0.01 | 0.01 | 0.01 |
| arginine | 0.01 | 0.01 | 0.01 | 0.01 | 0.01 | 0.01 | 0.01 |
| threonine | 0.01 | 0.01 | 0.01 | 0.01 | 0.01 | 0.01 | 0.01 |
| alanine | 0.01 | 0.01 | 0.01 | 0.01 | 0.01 | 0.01 | 0.01 |
| proline | 0.01 | 0.01 | 0.01 | 0.01 | 0.01 | 0.01 | 0.01 |
| serine | 0.01 | 0.01 | 0.01 | 0.01 | 0.01 | 0.01 | 0.01 |
| glycine | 0.01 | 0.01 | 0.01 | 0.01 | 0.01 | 0.01 | 0.01 |
| acetylglutamine | 0.01 | 0.01 | 0.01 | 0.01 | 0.01 | 0.01 | 0.01 |
| histidine | 0.01 | 0.01 | 0.01 | 0.01 | 0.01 | 0.01 | 0.01 |
| pyridoxylserine | 0.01 | 0.01 | 0.01 | 0.01 | 0.01 | 0.01 | 0.01 |
| carnosine | 0.01 | 0.01 | 0.01 | 0.01 | 0.01 | 0.01 | 0.01 |
| acetylmethionine | 0.01 | 0.01 | 0.01 | 0.01 | 0.01 | 0.01 | 0.01 |
| acetylcysteine | | | | | | | 0.10 |
| extract *1 | 0.10 | 0.10 | 0.10 | 0.10 | 0.10 | 0.10 | 0.10 |
| zinc pyrrolidone carboxylate | 0.01 | 0.01 | 0.01 | 0.01 | 0.01 | 0.01 | 0.01 |
| sodium pyrrolidone carboxylate | 0.001 | 0.001 | 0.001 | 0.001 | 0.001 | 0.001 | 0.001 |
| pyrrolidonecarboxylic acid salt of cocoyl arginine ethyl | 0.01 | 0.01 | 0.01 | 0.01 | 0.01 | 0.01 | 0.01 |
| EDTA-2Na | 0.05 | 0.05 | 0.05 | 0.05 | 0.05 | 0.05 | 0.05 |
| 10% arginine aqueous solution | q.s. | q.s. | q.s. | q.s. | q.s. | q.s. | q.s. |
| flavor | q.s. | q.s. | q.s. | q.s. | q.s. | q.s. | q.s. |
| purified water | balance | balance | balance | balance | balance | balance | balance |

TABLE 15

O/W type foundation (in wt %, total amount 100)

| Component | Form. Ex. 161 | Form. Ex. 162 | Form. Ex. 163 | Form. Ex. 164 | Form. Ex. 165 | Form. Ex. 166 | Form. Ex. 167 |
|---|---|---|---|---|---|---|---|
| talc | 3.00 | 3.00 | 3.00 | 3.00 | 3.00 | 3.00 | 3.00 |
| titanium oxide | 5.00 | 5.00 | 5.00 | 5.00 | 5.00 | 5.00 | 5.00 |
| ferric oxide red | 0.50 | 0.50 | 0.50 | 0.50 | 0.50 | 0.50 | 0.50 |
| yellow iron oxide | 1.40 | 1.40 | 1.40 | 1.40 | 1.40 | 1.40 | 1.40 |
| black iron oxide | 0.10 | 0.10 | 0.10 | 0.10 | 0.10 | 0.10 | 0.10 |
| bentonite | 0.50 | 0.50 | 0.50 | 0.50 | 0.50 | 0.50 | 0.50 |
| Polysorbate 60 | 0.90 | 0.90 | 0.90 | 0.90 | 0.90 | 0.90 | 0.90 |
| triethanolamine | 1.00 | 1.00 | 1.00 | 1.00 | 1.00 | 1.00 | 1.00 |
| PG | 10.00 | 10.00 | 10.00 | 10.00 | 10.00 | 10.00 | 10.00 |
| 4-t-butyl-4'-methoxydibenzoylmethane | | | 0.20 | 0.20 | 0.10 | | |
| octyl triazone | | | | | 0.10 | 0.20 | 0.20 |
| N-acetyl-2-methylthiazolidine-2,4-dicarboxylic acid 2-ethyl ester | | | 2.00 | 2.00 | 3.00 | 3.00 | 3.00 |
| N-acetyl-2-methylthiazolidine-2,4-dicarboxylic acid | | | | | | | |
| potassium N-acetyl-2-methylthiazolidine-2,4-dicarboxylic acid 2-ethyl ester | 2.00 | | | | | | |
| dipotassium N-acetyl-2-methylthiazolidine-2,4-dicarboxylic acid | | 2.00 | | | | | |
| *chamomilla recutita* extract | 1.00 | | 1.00 | | | | |
| rcinol | | 0.50 | | 0.50 | | | |
| GSH | | | | | 1.00 | | |
| tranexamic acid | | | | | | 1.00 | |
| 4-methoxy salicylic acid | | | | | | | 1.00 |
| safflower seed extract | | | | | | | |
| ascorbic acid 2-glucoside | | | | | | | |
| oligosaccharide | | | | | | | |
| ellagic acid | | | | | | | |
| hydroquinone | | | | | | | |
| *saxifraga sarmentosa* extract | | | | | | | |
| cetyl ascorbyl ether | | | | | | | |
| isoleucine | 0.01 | 0.01 | 0.01 | 0.01 | 0.01 | 0.01 | 0.01 |
| valine | 0.01 | 0.01 | 0.01 | 0.01 | 0.01 | 0.01 | 0.01 |
| phenylalanine | 0.01 | 0.01 | 0.01 | 0.01 | 0.01 | 0.01 | 0.01 |
| tryptophan | 0.01 | 0.01 | 0.01 | 0.01 | 0.01 | 0.01 | 0.01 |
| aspartic acid | 0.01 | 0.01 | 0.01 | 0.01 | 0.01 | 0.01 | 0.01 |
| sodium glutamate | 0.01 | 0.01 | 0.01 | 0.01 | 0.01 | 0.01 | 0.01 |
| lysine hydrochloride | 0.01 | 0.01 | 0.01 | 0.01 | 0.01 | 0.01 | 0.01 |

TABLE 15-continued

| O/W type foundation (in wt %, total amount 100) | | | | | | | |
|---|---|---|---|---|---|---|---|
| arginine | 0.01 | 0.01 | 0.01 | 0.01 | 0.01 | 0.01 | 0.01 |
| threonine | 0.01 | 0.01 | 0.01 | 0.01 | 0.01 | 0.01 | 0.01 |
| alanine | 0.01 | 0.01 | 0.01 | 0.01 | 0.01 | 0.01 | 0.01 |
| proline | 0.01 | 0.01 | 0.01 | 0.01 | 0.01 | 0.01 | 0.01 |
| serine | 0.01 | 0.01 | 0.01 | 0.01 | 0.01 | 0.01 | 0.01 |
| glycine | 0.01 | 0.01 | 0.01 | 0.01 | 0.01 | 0.01 | 0.01 |
| acetylglutamine | 0.01 | 0.01 | 0.01 | 0.01 | 0.01 | 0.01 | 0.01 |
| histidine | 0.01 | 0.01 | 0.01 | 0.01 | 0.01 | 0.01 | 0.01 |
| pyridoxylserine | 0.01 | 0.01 | 0.01 | 0.01 | 0.01 | 0.01 | 0.01 |
| carnosine | 0.01 | 0.01 | 0.01 | 0.01 | 0.01 | 0.01 | 0.01 |
| acetylmethionine | 0.01 | 0.01 | 0.01 | 0.01 | 0.01 | 0.01 | 0.01 |
| acetylcysteine | 0.01 | 0.01 | 0.01 | 0.01 | 0.01 | 0.01 | 0.01 |
| extract *1 | 0.10 | 0.10 | 0.10 | 0.10 | 0.10 | 0.10 | 0.10 |
| zinc pyrrolidone carboxylate | 0.01 | 0.01 | 0.01 | 0.01 | 0.01 | 0.01 | 0.01 |
| sodium pyrrolidone carboxylate | 0.00 | 0.00 | 0.00 | 0.00 | 0.00 | 0.00 | 0.00 |
| pyrrolidonecarboxylic acid salt of cocoyl arginine ethyl | 0.01 | 0.01 | 0.01 | 0.01 | 0.01 | 0.01 | 0.01 |
| stearic acid | 2.20 | 2.20 | 2.20 | 2.20 | 2.20 | 2.20 | 2.20 |
| isohexadecyl alcohol | 7.00 | 7.00 | 7.00 | 7.00 | 7.00 | 7.00 | 7.00 |
| glyceryl stearate | 2.00 | 2.00 | 2.00 | 2.00 | 2.00 | | |
| glyceryl stearate | | | | | | 2.00 | 2.00 |
| liquid lanolin | 2.00 | 2.00 | 2.00 | 2.00 | 2.00 | 2.00 | 2.00 |
| di(octyldodecyl/phytosteryl/behenyl)-lauroyl glutamate | 0.01 | 0.01 | 0.01 | 0.01 | 0.01 | 0.01 | 0.01 |
| di(cholesteryl/behenyl/octyldodecyl)-lauroyl glutamate | 0.01 | 0.01 | 0.01 | 0.01 | 0.01 | 0.01 | 0.01 |
| liquid paraffin | 8.00 | 8.00 | 8.00 | 8.00 | 8.00 | 8.00 | 8.00 |
| 10% arginine aqueous solution | q.s. | q.s. | q.s. | q.s. | q.s. | q.s. | q.s. |
| methylparaben | 0.20 | 0.20 | 0.20 | 0.20 | 0.20 | 0.20 | 0.20 |
| flavor | q.s. | q.s. | q.s. | q.s. | q.s. | q.s. | q.s. |
| purified water | balance | balance | balance | balance | balance | balance | balance |

| Component | Form. Ex. 168 | Form. Ex. 169 | Form. Ex. 170 | Form. Ex. 171 | Form. Ex. 172 | Form. Ex. 173 | Form. Ex. 174 |
|---|---|---|---|---|---|---|---|
| talc | 3.00 | 3.00 | 3.00 | 3.00 | 3.00 | 3.00 | 3.00 |
| titanium oxide | 5.00 | 5.00 | 5.00 | 5.00 | 5.00 | 5.00 | 5.00 |
| ferric oxide red | 0.50 | 0.50 | 0.50 | 0.50 | 0.50 | 0.50 | 0.50 |
| yellow iron oxide | 1.40 | 1.40 | 1.40 | 1.40 | 1.40 | 1.40 | 1.40 |
| black iron oxide | 0.10 | 0.10 | 0.10 | 0.10 | 0.10 | 0.10 | 0.10 |
| bentonite | 0.50 | 0.50 | 0.50 | 0.50 | 0.50 | 0.50 | 0.50 |
| Polysorbate 60 | 0.90 | 0.90 | 0.90 | 0.90 | 0.90 | 0.90 | 0.90 |
| triethanolamine | 1.00 | 1.00 | 1.00 | 1.00 | 1.00 | 1.00 | 1.00 |
| PG | 10.00 | 10.00 | 10.00 | 10.00 | 10.00 | 10.00 | 10.00 |
| 4-t-butyl-4'-methoxydibenzoylmethane | | | 0.20 | 0.20 | 0.10 | | |
| octyl triazone | | | | | 0.10 | 0.20 | 0.20 |
| N-acetyl-2-methylthiazolidine-2,4-dicarboxylic acid 2-ethyl ester | | | | | | | |
| N-acetyl-2-methylthiazolidine-2,4-dicarboxylic acid | 1.00 | 1.00 | 2.00 | 2.00 | 3.00 | 3.00 | 3.00 |
| potassium N-acetyl-2-methylthiazolidine-2,4-dicarboxylic acid 2-ethyl ester | | | | | | | |
| dipotassium N-acetyl-2-methylthiazolidine-2,4-dicarboxylic acid | | | | | | | |
| chamomilla recutita extract | | | | | | | |
| rcinol | | | | | | | |
| GSH | | | | | | | |
| tranexamic acid | | | | | | | |
| 4-methoxy salicylic acid | | | | | | | |
| safflower seed extract | 0.20 | | | | | | |
| ascorbic acid 2-glucoside | | 1.00 | | | | | |
| oligosaccharide | | | 2.00 | | | | |
| ellagic acid | | | | 0.10 | | | |
| hydroquinone | | | | | 0.10 | | |
| saxifraga sarmentosa extract | | | | | | 2.00 | |
| cetyl ascorbyl ether | | | | | | | 0.20 |
| isoleucine | 0.01 | 0.01 | 0.01 | 0.01 | 0.01 | 0.01 | 0.01 |
| valine | 0.01 | 0.01 | 0.01 | 0.01 | 0.01 | 0.01 | 0.01 |
| phenylalanine | 0.01 | 0.01 | 0.01 | 0.01 | 0.01 | 0.01 | 0.01 |
| tryptophan | 0.01 | 0.01 | 0.01 | 0.01 | 0.01 | 0.01 | 0.01 |
| aspartic acid | 0.01 | 0.01 | 0.01 | 0.01 | 0.01 | 0.01 | 0.01 |
| sodium glutamate | 0.01 | 0.01 | 0.01 | 0.01 | 0.01 | 0.01 | 0.01 |
| lysine hydrochloride | 0.01 | 0.01 | 0.01 | 0.01 | 0.01 | 0.01 | 0.01 |

TABLE 15-continued

| O/W type foundation (in wt %, total amount 100) | | | | | | | |
|---|---|---|---|---|---|---|---|
| arginine | 0.01 | 0.01 | 0.01 | 0.01 | 0.01 | 0.01 | 0.01 |
| threonine | 0.01 | 0.01 | 0.01 | 0.01 | 0.01 | 0.01 | 0.01 |
| alanine | 0.01 | 0.01 | 0.01 | 0.01 | 0.01 | 0.01 | 0.01 |
| proline | 0.01 | 0.01 | 0.01 | 0.01 | 0.01 | 0.01 | 0.01 |
| serine | 0.01 | 0.01 | 0.01 | 0.01 | 0.01 | 0.01 | 0.01 |
| glycine | 0.01 | 0.01 | 0.01 | 0.01 | 0.01 | 0.01 | 0.01 |
| acetylglutamine | 0.01 | 0.01 | 0.01 | 0.01 | 0.01 | 0.01 | 0.01 |
| histidine | 0.01 | 0.01 | 0.01 | 0.01 | 0.01 | 0.01 | 0.01 |
| pyridoxylserine | 0.01 | 0.01 | 0.01 | 0.01 | 0.01 | 0.01 | 0.01 |
| carnosine | 0.01 | 0.01 | 0.01 | 0.01 | 0.01 | 0.01 | 0.01 |
| acetylmethionine | 0.01 | 0.01 | 0.01 | 0.01 | 0.01 | 0.01 | 0.01 |
| acetylcysteine | 0.01 | 0.01 | 0.01 | 0.01 | 0.01 | 0.01 | 0.01 |
| extract *1 | 0.10 | 0.10 | 0.10 | 0.10 | 0.10 | 0.10 | 0.10 |
| zinc pyrrolidone carboxylate | 0.01 | 0.01 | 0.01 | 0.01 | 0.01 | 0.01 | 0.01 |
| sodium pyrrolidone carboxylate | 0.00 | 0.00 | 0.00 | 0.00 | 0.00 | 0.00 | 0.00 |
| pyrrolidonecarboxylic acid salt of cocoyl arginine ethyl | 0.01 | 0.01 | 0.01 | 0.01 | 0.01 | 0.01 | 0.01 |
| stearic acid | 2.20 | 2.20 | 2.20 | 2.20 | 2.20 | 2.20 | 2.20 |
| isohexadecyl alcohol | 7.00 | 7.00 | 7.00 | 7.00 | 7.00 | 7.00 | 7.00 |
| glyceryl stearate | 2.00 | 2.00 | 2.00 | 2.00 | 2.00 | | |
| glyceryl stearate | | | | | | 2.00 | 2.00 |
| liquid lanolin | 2.00 | 2.00 | 2.00 | 2.00 | 2.00 | 2.00 | 2.00 |
| di(octyldodecyl/phytosteryl/behenyl)-lauroyl glutamate | 0.01 | 0.01 | 0.01 | 0.01 | 0.01 | 0.01 | 0.01 |
| di(cholesteryl/behenyl/octyldodecyl)-lauroyl glutamate | 0.01 | 0.01 | 0.01 | 0.01 | 0.01 | 0.01 | 0.01 |
| liquid paraffin | 8.00 | 8.00 | 8.00 | 8.00 | 8.00 | 8.00 | 8.00 |
| 10% arginine aqueous solution | q.s. | q.s. | q.s. | q.s. | q.s. | q.s. | q.s. |
| methylparaben | 0.20 | 0.20 | 0.20 | 0.20 | 0.20 | 0.20 | 0.20 |
| flavor | q.s. | q.s. | q.s. | q.s. | q.s. | q.s. | q.s. |
| purified water | balance | balance | balance | balance | balance | balance | balance |

TABLE 16

| lipstick (in wt %, total amount 100) | | | | | | |
|---|---|---|---|---|---|---|
| Component | Form. Ex. 175 | Form. Ex. 176 | Form. Ex. 177 | Form. Ex. 178 | Form. Ex. 179 | Form. Ex. 180 |
| candelilla wax | 8.00 | 8.00 | 8.00 | 8.00 | 8.00 | 8.00 |
| paraffin | 6.00 | 6.00 | 6.00 | 6.00 | 6.00 | 6.00 |
| beeswax | 3.00 | 3.00 | 3.00 | 3.00 | 3.00 | 3.00 |
| carnauba wax | 2.00 | 2.00 | 2.00 | 2.00 | 2.00 | 2.00 |
| lanolin | 7.17 | 7.17 | 7.17 | 7.17 | 7.17 | 7.17 |
| castor oil | 13.30 | 13.80 | 14.20 | 13.30 | 13.80 | 14.20 |
| cetyl ethylhexanoate | 13.03 | 13.03 | 13.03 | 13.03 | 13.03 | 13.03 |
| ethylhexyl palmitate | 10.32 | 10.32 | 10.32 | 10.32 | 10.32 | 10.32 |
| hydrogenated polyisobutene | 5.00 | 5.00 | 5.00 | 5.00 | 5.00 | 5.00 |
| Red 202 | 1.05 | 1.05 | 1.05 | 1.05 | 1.05 | 1.05 |
| Yellow 4 | 0.90 | 0.90 | 0.90 | 0.90 | 0.90 | 0.90 |
| Blue 1 | 0.04 | 0.04 | 0.04 | 0.04 | 0.04 | 0.04 |
| titanium oxide | 1.60 | 1.60 | 1.60 | 1.60 | 1.60 | 1.60 |
| diisostearyl malate | 3.59 | 3.59 | 3.59 | 3.59 | 3.59 | 3.59 |
| mica, titanium oxide | 1.00 | 1.00 | 1.00 | 1.00 | 1.00 | 1.00 |
| mica | 1.00 | 1.00 | 1.00 | 1.00 | 1.00 | 1.00 |
| N-acetyl-2-methylthiazolidine-2,4-dicarboxylic acid 2-ethyl ester | 2.00 | 2.00 | 2.00 | | | |
| N-acetyl-2-methylthiazolidine-2,4-dicarboxylic acid | | | | 2.00 | 2.00 | 2.00 |
| linoleic acid | 1.00 | | 1.00 | | | |
| cetyl ascorbyl ether | | 0.50 | | | 0.50 | |
| rcinol | | | | 0.10 | | 0.10 |
| bis(N-lauroyl-L-glutamate/N-lauroyl-sarcosinate) dimer dilinoleyl | 20.00 | 20.00 | 20.00 | 20.00 | 20.00 | 20.00 |

*1: Any of extracts 1 to 94 in Table 17-1 to Table 17-3 can be used.

TABLE 17

| | raw material name | |
|---|---|---|
| extract 1 | angelica actiloba | plant extract (crude drug) |
| extract 2 | spruce | |
| extract 3 | chili pepper | |
| extract 4 | persicae semen | |
| extract 5 | cnidium officinale | |
| extract 6 | amur cork | |
| extract 7 | birch | |
| extract 8 | common sorrel | |
| extract 9 | sophora angustifolia | |
| extract 10 | peony root | |
| extract 11 | asiasarum root | |
| extract 12 | pyracantha fortuneana | |
| extract 13 | swertia herba | |
| extract 14 | aurantii nobilis pericarpium | |
| extract 15 | clove | |
| extract 16 | glehnia littoralis | |
| extract 17 | loofah | |
| extract 18 | saxifraga sarmentosa | |
| extract 19 | artemisia | |
| extract 20 | aloe | |

TABLE 17-continued

| raw material name | | |
|---|---|---|
| extract 21 | watercress | |
| extract 22 | burnet | |
| extract 23 | aesculus hippocastanum bark | |
| extract 24 | polygonum bistorta | |
| extract 25 | scutellaria baicalensis | |
| extract 26 | polygonum cuspidatum | |
| extract 27 | safflower | |
| extract 28 | safflower seed | |
| extract 29 | elder | |
| extract 30 | magnolia | |
| extract 31 | daisy | |
| extract 32 | rose fruit | |
| extract 33 | persimmon tannin | plant extract |
| extract 34 | ginkgo biloba leaf | (crude drug) |
| extract 35 | black currant | |
| extract 36 | black tea | |
| extract 37 | green tea | |
| extract 38 | oolong tea | |
| extract 39 | tamarindus indica | |
| extract 40 | aspalathus linearis | |
| extract 41 | mulberry bark | |
| extract 42 | magnolia bark | |
| extract 43 | oil-soluble glycyrrhiza | |
| extract 44 | linseed | |
| extract 45 | peony root | |
| extract 46 | calamus | |
| extract 47 | phellodendron bark | |
| extract 48 | peach leaves | |
| extract 49 | lavender | |
| extract 50 | peppermint | |
| extract 51 | salvia officinalis(sage) | |
| extract 52 | anise | |
| extract 53 | rose | |
| extract 54 | lemon | |
| extract 55 | orange | |
| extract 56 | orange juice | |
| extract 57 | grapefruit | |
| extract 58 | citrus junos | |
| extract 59 | raspberry | |
| extract 60 | acerola | |
| extract 61 | apricot | |
| extract 62 | syzygium jambos | |
| extract 63 | rosa eglanteria | |
| extract 64 | thyme | |
| extract 65 | malva sylvestris | |
| extract 66 | arnica montana | plant extract |
| extract 67 | dioscorea composita | (crude drug) |
| extract 68 | achillea sibirica | |
| extract 69 | gardenia florida | |
| extract 70 | lily | |
| extract 71 | gentian | |
| extract 72 | sawara cypress | |
| extract 73 | purple bergenia | |
| extract 74 | wheat germ | |
| extract 75 | birch | |
| extract 76 | chlorella | seaweed extract |
| extract 77 | enteromorpha | (green algae) |
| extract 78 | chlamydomonas | |
| extract 79 | tangle weed | (brown algae) |
| extract 80 | undaria pinnatifida | |
| extract 81 | fucus vesiculosus | (brown algae) |
| extract 82 | cyrtymenia sparsa | (red algae) |
| extract 83 | ptilophora subcostata | |
| extract 84 | gigartina tenella | |
| extract 85 | aphanothece sacrum | (blue algae) |
| extract 86 | nostoc verrucosum | |
| extract 87 | nitellopsis obtusa | (charophytes) |
| extract 88 | chromulina rosanoffii | (yellow algae) |
| extract 89 | placenta | other extracts |
| extract 90 | milk serum | |
| extract 91 | yeast | |
| extract 92 | soy milk | |
| extract 93 | rice bran | |
| extract 94 | royal jelly | |

In the above-mentioned Formulation Examples, BG is 1,3-butyleneglycol, PG is propyleneglycol, DPG is dipropyleneglycol, PEG is polyethylene glycol, and PPG is polypropyleneglycol.

INDUSTRIAL APPLICABILITY

It has been clarified that the cosmetic agent of the present invention is superior in the stability and safety, and has a whitening effect. Therefore, a cosmetic agent having a higher effect and more resistant to skin trouble than conventional whitening cosmetic agents can be provided. In addition, the melanin production suppressive agent of the present invention suppresses production of melanin and is effective for, for example, a whitening action or prophylaxis, improvement or treatment of pigmented spots.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cosmetic agent, comprising:
   (A) at least one cysteine compound represented by formula (I) or a salt thereof:

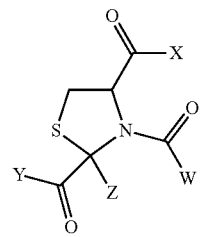

(I)

wherein
   X and Y are each independently $OR^1$ or $NHR^2$ wherein $R^1$ and $R^2$ are each independently a hydrogen atom or a $C_{1-22}$ alkyl group;
   Z is a hydrogen atom or a $C_{1-22}$ alkyl group; and
   W is a $C_{1-22}$ alkyl group, a $C_{1-22}$ alkoxy group or a $C_{1-22}$ alkylamino group; and
   (B) at least one whitening agent,
   wherein:
   (A) said at least one cysteine compound or a salt thereof is one or more members selected from the group consisting of N-acetyl-2-methylthiazolidine-2,4-dicarboxylic acid, a salt of N-acetyl-2-methylthiazolidine-2,4-dicarboxylic acid, N-acetyl-2-methylthiazolidine-2,4-dicarboxylic acid 2-ethyl ester, and a salt of N-acetyl-2-methylthiazolidine-2,4-dicarboxylic acid 2-ethyl ester; and
   (B) said at least one whitening agent is one or more members selected from the group consisting of arbutin, cetyl ascorbyl ether, kojic acid, 4-methoxy salicylic acid, chamomilla recutita extract, ellagic acid, linoleic acid, glutathione, tranexamic acid, 4-n-butylresorcinol, and 4-hexylresorcinol.

2. The cosmetic agent according to claim 1, wherein (B) said at least one whitening agent is one or more members selected from the group consisting of arbutin, kojic acid, 4-methoxy salicylic acid, chamomilla recutita extract, glutathione, and tranexamic acid.

3. The cosmetic agent according to claim 1, wherein (B) said at least one whitening agent is one or more members selected from the group consisting of arbutin, kojic acid, chamomilla recutita extract, tranexamic acid.

4. The cosmetic agent according to claim 1, wherein (A) said at least one cysteine compound or a salt thereof is N-acetyl-2-methylthiazolidine-2,4-dicarboxylic acid 2-ethyl ester or a salt thereof, and (B) said at least one whitening agent is kojic acid.

5. The cosmetic agent according to claim 1, wherein (A) said at least one cysteine compound or a salt thereof is N-acetyl-2-methylthiazolidine-2,4-dicarboxylic acid 2-ethyl ester or a salt thereof, and (B) said at least one whitening agent is tranexamic acid.

6. The cosmetic agent according to claim 1, wherein (A) said at least one cysteine compound or a salt thereof is N-acetyl-2-methylthiazolidine-2,4-dicarboxylic acid 2-ethyl ester or a salt thereof, and (B) said at least one whitening agent is a chamomilla recutita extract.

7. The cosmetic agent according to claim 1, wherein (A) said at least one cysteine compound or a salt thereof is N-acetyl-2-methylthiazolidine-2,4-dicarboxylic acid 2-ethyl ester or a salt thereof, and (B) said at least one whitening agent is arbutin.

8. The cosmetic agent according to claim 1, wherein (A) said at least one cysteine compound or a salt thereof and (B) said at least one whitening agent are present in a mass ratio of (A)/(B)=1/20-5000/1 (g/g).

9. The cosmetic agent according to claim 1, wherein (A) said at least one cysteine compound represented by formula (I) is one or more members selected from the group consisting of a (2R,4S)-form, a (2S,4R)-form, and a mixture thereof.

10. The cosmetic agent according to claim 1, wherein (A) said at least one cysteine compound represented by formula (I) is a (2S,4R)-form.

11. A melanin production suppressive agent, comprising:
(A) at least one cysteine compound represented by formula (I) or a salt thereof:

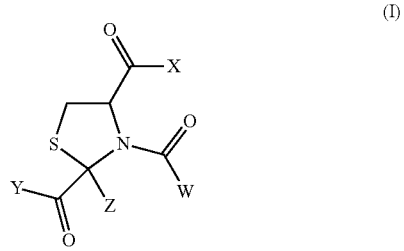

(I)

wherein
X and Y are each independently $OR^1$ or $NHR^2$ wherein $R^1$ and $R^2$ are each independently a hydrogen atom or a $C_{1-22}$ alkyl group;
Z is a hydrogen atom or a $C_{1-22}$ alkyl group; and
W is a $C_{1-22}$ alkyl group, a $C_{1-22}$ alkoxy group or a $C_{1-22}$ alkylamino group; and
(B) at least one whitening agent
wherein:
(A) said at least one cysteine compound or a salt thereof is one or more members selected from the group consisting of N-acetyl-2-methylthiazolidine-2,4-dicarboxylic acid, a salt of N-acetyl-2-methylthiazolidine-2,4-dicarboxylic acid, N-acetyl-2-methylthiazolidine-2,4-dicarboxylic acid 2-ethyl ester, and a salt of N-acetyl-2-methylthiazolidine-2,4-dicarboxylic acid 2-ethyl ester; and
(B) said at least one whitening agent is one or more members selected from the group consisting of arbutin, cetyl ascorbyl ether, kojic acid, 4-methoxy salicylic acid, chamomilla recutita extract, ellagic acid, linoleic acid, glutathione, tranexamic acid, 4-n-butylresorcinol, and 4-hexylresorcinol.

12. The melanin production suppressive agent according to claim 11, wherein (B) said at least one whitening agent is one or more members selected from the group consisting of arbutin, kojic acid, 4-methoxy salicylic acid, chamomilla recutita extract, glutathione, and tranexamic acid.

13. The melanin production suppressive agent according to claim 11, wherein (A) said at least one cysteine compound represented by formula (I) is one or more members selected from the group consisting of a (2R,4S)-form, a (2S,4R)-form, and a mixture thereof.

14. The melanin production suppressive agent according to claim 11, wherein (A) said at least one cysteine derivative represented by formula (I) is a (2S,4R)-form.

15. A method of suppressing melanin production, comprising administering to a subject in need thereof an effective amount of a cosmetic agent according to claim 1.

16. A method according to claim 15, wherein said administering is topical administering.

17. A method of whitening skin, comprising administering to a subject in need thereof an effective amount of a cosmetic agent according to claim 1.

18. A method according to claim 17, wherein said administering is topical administering.

19. A method of suppressing melanin production, comprising administering to a subject in need thereof an effective amount of a cosmetic agent according to claim 2.

20. A method according to claim 19, wherein said administering is topical administering.

21. A method of whitening skin, comprising administering to a subject in need thereof an effective amount of a cosmetic agent according to claim 2.

22. A method according to claim 21, wherein said administering is topical administering.

* * * * *